US008906610B2

(12) United States Patent
Brodie et al.

(10) Patent No.: US 8,906,610 B2
(45) Date of Patent: *Dec. 9, 2014

(54) USING PHYLOGENETIC PROBES FOR QUANTIFICATION OF STABLE ISOTOPE LABELING AND MICROBIAL COMMUNITY ANALYSIS

(75) Inventors: Eoin L. Brodie, Piedmont, CA (US); Todd Z. DeSantis, Livermore, CA (US); Ulas Karaoz, Berkeley, CA (US); Gary L. Andersen, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/023,538

(22) Filed: Feb. 8, 2011

(65) Prior Publication Data

US 2011/0212850 A1   Sep. 1, 2011

Related U.S. Application Data

(60) Provisional application No. 61/302,535, filed on Feb. 8, 2010, provisional application No. 61/302,827, filed on Feb. 9, 2010.

(51) Int. Cl.
| | | |
|---|---|---|
| *C12Q 1/68* | (2006.01) | |
| *C12Q 1/04* | (2006.01) | |
| *C12Q 1/16* | (2006.01) | |
| *G01N 33/68* | (2006.01) | |

(52) U.S. Cl.
CPC .......... *G01N 33/6848* (2013.01); *C12Q 1/6837* (2013.01)
USPC ............ 435/6.1; 435/6.11; 435/6.15; 435/34; 435/35

(58) Field of Classification Search
None
See application file for complete search history.

(56) References Cited

U.S. PATENT DOCUMENTS

| | | |
|---|---|---|
| 7,015,471 B2 | 3/2006 | Franzen et al. |
| 2004/0058380 A1 | 3/2004 | Levon et al. |
| 2004/0086423 A1* | 5/2004 | Wohlstadter et al. ........... 422/52 |
| 2004/0180369 A1 | 9/2004 | Franzen et al. |
| 2005/0244414 A1 | 11/2005 | Mundy et al. |
| 2006/0147969 A1 | 7/2006 | Kuimelis et al. |
| 2008/0076128 A1 | 3/2008 | Hah et al. |
| 2008/0182758 A1 | 7/2008 | Ugolin et al. |
| 2009/0137426 A1 | 5/2009 | Jung et al. |
| 2009/0203549 A1 | 8/2009 | Hoeprich |
| 2009/0291858 A1 | 11/2009 | Andersen et al. |

FOREIGN PATENT DOCUMENTS

| | | |
|---|---|---|
| WO | 00/65099 A1 | 11/2000 |
| WO | 2006/054297 A2 | 5/2006 |
| WO | 2006/078356 A1 | 7/2006 |
| WO | 2006/114420 A1 | 11/2006 |
| WO | 2007/050501 A2 | 5/2007 |
| WO | 2008/028206 A2 | 3/2008 |
| WO | 2009/100201 A2 | 8/2009 |

OTHER PUBLICATIONS

Hesselsoe et al., Isotope array analysis of Rhodocyclales uncovers functional redundancy and versatility in an activated sludge; The ISME Journal, vol. 3, pp. 1349-1364, 2009.*
Li et al., Simultaneous analysis of microbial identity and function using NanoSIMS; Environmental Microbiology, vol. 10, No. 3, pp. 580-588, 2008.*
Godin et al., Simultaneous measurement of 13C- and 15N-isotopic enrichments of threonine by mass spectrometry; Rapid Communications in Mass Spectrometry, vol. 23, pp. 1109-1115, 2009.*
Adamczyk, J. et al. (Nov. 2003). "The Isotope Array, A New Tool that Employs Substrate-Mediated Labeling of rRNA for Determination of Microbial Community Structure and Function," Applied and Environmental Microbiology 69 (11):6875-6887.
Addison, S. L. et al. (2010). "Stable Isotope Probing: Technical Considerations when Resolving 15N-Labeled RNA in Gradients," Journal of Microbiological Methods 80:70-75.
Ammerman, J. W. et al. (Mar. 15, 1985). "Bacterial 5'-Nucleotidase in Aquatic Ecosystems: A Novel Mechanism of Phosphorous Regeneration," Science 227:1338-1340.
Behrens, S. et al. (May 2008). "Linking Microbial Phylogeny to Metabolic Activity at the Single-Cell Level by Using Enhanced Element Labeling-Catalyzed Reporter Deposition Fluorescence in Situ Hybridization (EL-FISH) and NanoSIMS," Applied and Environment Microbiology 74(1):3143-3150.
Boschker, H. T. S. et al. (Apr. 23, 1998). "Direct Linking of Microbial Populations to Specific Biogeochemical Processes by 13C-Labelling of Biomarkers," Nature 392:801-805.
Brodie, E. L. et al. (Sep. 2006). "Application of a High-Density Oligonucleotide Microarray Approach to Study Bacterial Population Dynamics During Uranium Reduction and Reoxidation," Applied and Environmental Microbiology 72(9):6288-6298.
Cline, M. S. et al. (2007). "Integration of Biological Networks and Gene Expression Data Using Cytoscape," Nature Protocols 2(10):2366-2382.
DeFlaun, M. F. et al. (May 21, 1987). "Distribution and Molecular Weight of Dissolved DNA in Subtropical Estuarine and Oceanic Environments," Marine Ecology-Progress Series 38:65-73.
DeLong, E. F. et al. (Jan. 27, 2006). "Community Genomics Among Stratified Microbial Assemblages in the Ocean's Interior," Science 311:496-503.
DeSantis, T. Z. et al. (Jul. 2006). "Greengenes, A Chimera-Checked 16S rRNA Gene Database and Workbench Compatible with ARB," Applied and Environmental Microbiology 72(7):5069-5072.
Doolittle, W. F. et al. (2009). "On the Origin of Prokaryotic Species," Genome Research 19:744-756.

(Continued)

*Primary Examiner* — Jennifer Dunston
*Assistant Examiner* — Addison D Ault
(74) *Attorney, Agent, or Firm* — Michelle Chew Wong; Lawrence Berkeley National Laboratory

(57) ABSTRACT

Herein is described methods for a high-sensitivity means to measure the incorporation of stable isotope labeled substrates into RNA following stable isotope probing experiments (SIP). RNA is hybridized to a set of probes such as phylogenetic microarrays and isotope incorporation is quantified such as by secondary ion mass spectrometer imaging (Nano-SIMS).

43 Claims, 17 Drawing Sheets

(56) References Cited

OTHER PUBLICATIONS

Dugdale, R. C. et al. (2007). "The Role of Ammonium and Nitrate in Spring Bloom Development in San Francisco Bay," Estuarine, Coastal and Shelf Science 73:17-29.

Dumont, M. G. et al. (Jun. 2005). "Stable Isotope Probing: Linking Microbial Identity to Function," Nature Reviews Microbiology 3:499-504.

Evens, R. et al. (1988). "A Seasonal Comparison of the Dissolved Free Amino Acid Levels in Estuarine and English Channel Waters," The Science of the Total Environment 76:69-78.

Falkowski, P. et al. (Oct. 13, 2000). "The Global Carbon Cycle: A Test of Our Knowledge of Earth as a System," Science 290:291-296.

Fernandez-Reiriz, M. J. et al. (1989). "Biomass Production and Variation in the Biochemical Profile (Total Protein, Carbohydrates, RNA, Lipids and Fatty Acids) of Seven Species of Marine Microalgae," Aquaculture 83:17-37.

Fuhrman, J. A. et al. (Jun. 1980). "Bacterioplankton Secondary Production Estimates for Coastal Waters of British Columbia, Canada, Antarctica, and California," Applied and Environmental Microbiology 39(6):1085-1095.

Giovannoni, S. J. et al. (Sep. 15, 2005). "Molecular Diversity and Ecology of Microbial Plankton," Nature 437:343-348.

Goldman, J. C. et al. (1991). "Ammonium Regeneration and Carbon Utilization by Marine Bacteria Grown on Mixed Substrates," Marine Biology 109:369-378.

Hanson, R. B. et al. (1980). "Glucose Exchanges in a Salt Marsh-Estuary: Biological Activity and Chemical Measurements," Limnology and Oceanography 25(4):633-642.

Hunt, D. E. et al. (May 23, 2008). "Resource Partitioning and Sympatric Differentiation Among Closely Related Bacterioplankton," Science 320:1081-1085.

Kirchman, D. et al. (Mar. 1985). "Leucine Incorporation and its Potential as a Measure of Protein Synthesis by Bacteria in Natural Aquatic Systems," Applied and Environmental Microbiology 49(3):599-607.

Lauro, F. M. et al. (Sep. 15, 2009). "The Genomic Basis of Trophic Strategy in Marine Bacteria," Proceedings of the National Academy of Sciences of the United States of America 106(37):15527-15533.

Lennon, J. T. (May 2007). "Diversity and Metabolism of Marine Bacteria Cultivated on Dissolved DNA," Applied and Environmental Microbiology 73(9):2799-2805.

Ludwig, W. et al. (2004). "ARB: A Software Environment for Sequence Data," Nucleic Acids Research 32 (4):1363-1371.

Manefield, M. et al. (Nov. 2002). "RNA Stable Isotope Probing, A Novel Means of Linking Microbial Community Function to Phylogeny," Applied and Environmental Microbiology 68(11):5367-5373.

Martinez, J. et al. (Jun. 27, 1996). "Variability in Ectohydrolytic Enzyme Activities of Pelagic Marine Bacteria and its Significance for Substrate Processing in the Sea," Aquatic Microbial Ecology 10:223-230.

Murrell, J. C. et al. eds. (Dec. 2010). Stable Isotope Probing and Related Technologies. ASM Press: Washington D.C. (Table of Contents only, 4 pages).

Neufeld, J. D. et al. (2007). "Who Eats What, Where and When? Isotope-Labelling Experiments are Coming of Age," The ISME Journal 1:103-110.

Ouverney, C. C. et al. (Apr. 1999). "Combined Microautoradiography-16S rRNA Probe Technique for Determination of Radioisotope Uptake by Specific Microbial Cell Types in Situ," Applied and Environmental Microbiology 65 (4):1746-1752.

Pomeroy, L. R. et al. (2007). "The Microbial Loop," Oceanography 20(2):28-33.

Poretsky, R. S. et al. (2010). "Transporter Genes Expressed by Coastal Bacterioplankton in Response to Dissolved Organic Carbon," Environmental Microbiology 12(3):616-627.

Radajewski, S. et al. (Feb. 10, 2000). "Stable-Isotope Probing as a Tool in Microbial Ecology," Nature 403:646-649.

Rappe, M. S. et al. (1997). "Phylogenetic Diversity of Marine Coastal Picoplankton 16S rRNA Genes Cloned from the Continental Shelf Off Cape Hatteras, North Carolina," Limnology and Oceanography 42(5):811-826.

Rappe, M. S. et al. (Aug. 8, 2002). "Cultivation of the Ubiquitous SAR11 Marine Bacterioplankton Clade," Nature 418:630-633.

Singh-Gasson, S. et al. (Oct. 1999). "Maskless Fabrication of Light-Directed Oligonucleotide Microarrays Using a Digital Micromirror Array," Nature Biotechnology 17:974-978.

Stauffer, T. B. et al. (Dec. 1970). "Dissolved Fatty Acids in the James River Estuary, Virginia, and Adjacent Ocean Waters," Chesapeake Science 11(4):216-220.

Suttle, C. A. et al. (1990). "Rapid Ammonium Cycling and Concentration-Dependent Partitioning of Ammonium and Phosphate: Implications for Carbon Transfer in Planktonic Communities," Limnology and Oceanography 35 (2):424-433.

Uhlik, O. et al. (2009). "DNA-Based Stable Isotope Probing: A Link Between Community Structure and Function," Science of the Total Environment 407:3611-3619.

U.S. Office Action mailed on Oct. 26, 2012, for U.S. Appl. No. 13/023,468, filed Feb. 8, 2011, 12 pages.

U.S. Office Action mailed on Aug. 31, 2012, for U.S. Appl. No. 13/023,468, filed Feb. 8, 2011, 5 pages.

Cole, K., et al., Direct labeling of RNA with multiple biotins allows sensitive expression profiling acute leukemia class predictor genes, Nucleic Acids Research 2004, 32: e86.

Curtis, T., et al., Estimating prokaryotic diversity and its limits. PNAS 2002, 99: 10494-10499.

DeSantis, TZ, et al., Comprehensive aligned sequence construction for automated design of effective probes (cascade-p) using 16S rDNA, Bioinformatics 2003, 19: 1461-1468.

Marxer, C.G., et al., Supported membrane composition analysis by secondary ion mass spectrometry with high lateral resolution, Biophysical Journal 2005, 88: 2965-2975.

Gans, J., et al., Computational improvements reveal great bacterial diversity and high metal toxicity in soil, Science 2005, 309: 1387-1390.

Ghosal, S., et al., Analysis of bacterial spore permeability to water and ions using nano-secondary ion mass spectrometry (NanoSIMS), 232nd American Chemical Society National Meeting, Boston MA Aug. 19-23, 2007.

Gilbert, D., NewsOnLine newsletter, Lawrence Livermore National Laboratory Mar. 16, 2007.

Goodfellow, M., et al., Roots of bacterial systematic, In: Handbook of new bacterial systematic, 1993, pp. 2-54.

Hallegot, P. et al., In-Situ Imaging Mass Spectrometry Analysis of Melanin Granules in the Human Hair Shaft, Journal of Investigative Dermatology, 2004, vol. 122, pp. 381-386.

Hillion, F., et al., A new high performance SIMS instrument: The cameca "Nanosims 50", Secondary Ion Mass Spectrometry SIMS IX, 1993, pp. 254-257.

Horner-Devine, M., et al., An ecological perspective on bacterial biodiversity, Proceedings of the Royal Society of London—Series B: Biological Sciences 2004, 271: 113-122.

Hu, P., et al., Whole-genome transcriptional analysis of heavy metal stresses in *Caulobactor crescentus*, Journal of Bacteriology 2005, 187: 8437-8449.

Jeffries, TW, et al., Genome sequence of the lignocelluloses-bioconverting and xylose-fermenting yeast *Pichia stipitis*, Nature Biotechnology 2007, 25: 319-326.

Kleinfeld, MA, et al., Transport of 13C-oleate in adipocytes measured using multi-imaging mass spectrometry, Journal of the American Society for Mass Spectrometry 2004, 15: 1572-1580.

Klug, MJ, et al., Response of microbial communities to changing environmental conditions: Chemical and physiological approaches, In: Trends in microbial ecology, Spanish Society for Microbiology 1993, pp. 371-374.

Kraft, ML, et al., Phase separation of lipid membranes analyzed with high-resolution secondary mass ion spectrometry, Science 2006, 313: 1948-1951.

Kraft, ML, et al., Quantitative analysis of supported membrane composition using the NanoSIMS, Applied Surface Science 2006, 252: 6950-6956.

(56) References Cited

OTHER PUBLICATIONS

Kuypers, MM, et al., The future of single-cell environmental microbiology, Environmental Microbiology 2007, 9: 6-7.

Lehner, A., et al., Oligonucleotide microarray for identification of entrerococcus species, FEMS Microbiology Letters 2005, 246: 133-142.

Lin, LH, et al., Long-Term Sustainability of a High-Energy, Low-Diversity Crustal Biome, Science 2006, 314: 479-482.

Loy, A, et al., 16S rRNA Gene-Based Oligonucleotide Microarray for Environmental Monitoring of the Betaproteobacterial Order "Rhodocyclales", Appl. Environ. Microbiol. 2005, 71: 1373-1386.

MacGregor, BJ, et al., Isolation of small sub-unit rRNA for stable isotopic characterization, Environmental Microbiology 2002, 4: 451-464.

McMahon, G., et al. Quantitative imaging of cells with multi-isotope imaging mass spectrometry (MIMS)—nanoautography with stable isotope tracers, Appl. Surface Science 2006, 252: 6895-6906.

Moreau, JW, et al., Extracellular Proteins Limit the Dispersal of Biogenic Nanoparticles, Science 2007, 316: 1600-1603.

Moreau, JW, et al., Submicron-scale isotopic variations within biogene ZnS record the mechanism and kinetics of extracellular metal-sulfide biomineralization, presented at the Goldschmidt Conference, Melbourne Australia, Aug. 27, 2006 in Geochimica et Cosmochimica Acta 2006, 70: A428.

Nannipieri, P., et al., Microbial diversity and soil functions, Eur. Soil Sci. 2003, 54: 655-670.

Nardi, JB, et al., Communities of microbes that inhabit the changing hindgut landscape of a subsocial beetle, Arthropod Structure and Development 2006, 35: 57-68.

Nguyen, N.H. et al., *Metschnikowia noctiluminum* sp. nov., *Metschnikowia corniflorae* sp. nov., and *Candida chrysomelidarum* sp. nov., isolated from green lacewings and beetles, Mycological Research, 2006, 110: 346-356.

Orphan, JV, et al., Methane-consuming archaea revealed by directly coupled isotopic and phylogenetic analysis, Science 2001, 293: 484-487.

Peteranderl, R., et al., Measure of carbon and nitrogen stable isotope ratios in cultured cells, Journal of the American Society for Mass Spectrometry 2004, 15: 478-485.

Pett-Ridge, J., et al., Redox fluctuation structures in microbial communities in a wet tropical soil, Appl. Environ. Microbiol. 2005, 71: 6998-7007.

Pett-Ridge, J., et al., NanoSIMS analyses of molybdenum indicate nitrogenase activity and help solve a N and C fixation puzzle in a marine cyanobacterium, American Geophysical Union Fall Meeting 2006, San Francisco.

Phelps, TJ, et al. Comparison between geochemical and biological estimates of subsurface microbial activities, Microbial Ecology 1994, V28: 335-349.

Popa, R., et al., Carbon and nitrogen fixation and mobilization in and between individual cells of *Anabaena oscillarioides*, ISME 2007, 1: 1-7.

Radajewski, S. et al., Identification of active methylotroph populations in an acidic forest soil by stable-isotope probing, Microbiology 2002, 148: 2331-2342.

Radajewski, S., et al., Stable-isotope probing of nucleic acids: a window to the function of uncultured microorganisms, Current Opinion in Biotechnology 2004, 14: 296-302.

Rhee, SK, et al., Detection of Genes Involved in Biodegradation and Biotransformation in Microbial Communities by Using 50-Mer Oligonucleotide Microarrays, Applied and Environmental Microbiology 2004, 70: 4303-4317.

Romer, W., et al., Sub-cellular localization of a 15N-labelled peptide vector using NanoSIMS imaging, Applied Surface Science 2006, 252: 6925-6930.

Rosello-Mora, R., et al., The species concept for prokaryotes, FEMS Microbiology Reviews 2001, 25: 39-67.

Schubert, C., Can biofuels finally take center stage?, Nature Biotechnology 2006, 24: 777-784.

Small, JD, et al., Direct detection of 16S rRNA in soil extracts by using oligonucleotide microarrays, Applied and Environmental Microbiology 2001, 67: 4708-4716.

Smyth, C., et al., Auto-associative multivariate regression trees for cluster analysis. Chemometrics and Intelligent Laboratory Systems 2006, 80: 120-129.

Stadermann, FJ, et al., Sub-micron isotopic measurements with the Cameca NanoSIMS, 30th Lunar and Planetary Science Conference, Houston TX 1999.

Suh, S., et al., Wood ingestion by passalid beetles in the presence of xylose-fermenting gut yeasts, Molecular Ecology 2003, 12: 3137-3145.

Suh, S., et al., Expansion of the *Candida tanzawaensis* yeast clade: 16 novel *Candida* species from basidiocarp-feeding beetles, International Journal of Systematics and Evolutionary Microbiology 2004, 54: 2409-2429.

Torsvik, V., et al., High diversity in DNA of soil bacteria, Applied and Environmental Microbiology 1990, 56: 782-787.

Torsvik, V., et al., Microbial diversity and function in soil: from genes to ecosystems, Current Opinion in Microbiology 2002, 5: 240-245.

van Belkum, A., et al., Nonisotopic labeling of DNA by newly developed hapten-containing platinum compounds, Biotechniques 1994, 16: 148-153.

van der Laan, MJ, et al., A new algorithm for hybrid hierarchical clustering visualization and the bootstrap, Journal of Statistical Planning and Inference 2003, 117: pp. 275-303.

Wainwright, M., et al., Studies of bacteria-like particles sampled from the stratosphere, Acorobiologia 2004, 20: 1-10.

Wan, JM, et al., Reoxidation of bioreduced uranium under reducing conditions, Environmental Science & Technology 2005, 39: 6162-6169.

Weber, PK, et al., Chemical imaging of biological materials by NanoSIMS, 31st FACSS Meeting, Portland OR, Oct. 3-7, 2004.

Weber, PK, et al., High resolution trace element and isotopic imaging of microbial systems by NanoSims, American Geophysical Union Fall Meeting, San Francisco CA, Dec. 5-9, 2005.

Wellington, EM, et al., Resolving functional diversity in relation to microbial community structure in soil: exploiting genomics and stable isotopic probing, Current Opinion in Microbiology 2003, 6: 295-301.

White, RH, The difficult road from sequence to function, J. Bacteriol. 2006, 188: 3431-3432.

Whitman, W.B. et al., Perspective: Prokaryotes: The Unseen Majority, Proc. Natl. Acad. Sci. USA, Jun. 1998, vol. 95: pp. 6578-6583.

Zhang, N. et al., Microorganisms in the gut of beetles: evidence from molecular cloning, Journal of Invertebrate Pathology 2003, 84: 226-233.

Cupples, AM, et al., DNA buoyant density shifts during 15N-DNA stable isotope probing, Microbiol. Research 2006, 162: 328-334.

Pett-Ridge, J., et al., Microarrays + NanoSIMS: Linking microbial identity and function—LDRD quadchart ER project, Jun. 5, 2006.

Pett-Ridge, J. et al., Microarrays + NanoSIMS: Linking microbial identity and function—LDRD quadchart presentation, Mar. 10, 2006.

Profiling Microbial Identity and Activity: Novel Applications of NanoSIMS and High Density Microarrays—Doe Gtl grant proposal, Mar. 20, 2007.

Pett-Ridge, J., et al., Microarrays + NanoSIMS: Linking microbial identity and function—GtL workshop poster 2007, Feb. 20, 2007.

Pett-Ridge, J., et al., Microarrays + NanoSIMS: Linking microbial identity and function—Gordon Conference poster 2007, Jul. 19, 2007.

Pett-Ridge, J., et al., Microarrays + NanoSIMS: Linking microbial identity and function—ASM poster 2008, Jun. 9, 2008.

Hoeprich, P. et al., Synthesis of DNA Microarrays on Indium—Tin Oxide Surfaces Functionalized with Organophosphonate Monolayers and Organosilanes Enable Analysis by Secondary Ion Mass Spectrometry—ITO array surface peer-review paper.

Loy, A. et al. probeBase—an online resource for rRNA-targeted oligonucleotide probes: new features 2007, Nucleic Acids Research 2007, 35: doi: 10.1093/nar/gkl856, D800-D804.

Suh, S.O. et al. The beetle gut: a hyperdiverse source of novel yeasts, Mycolog. Res. 2005, vol. 109, pp. 261-265.

(56) References Cited

OTHER PUBLICATIONS

Moses, S. et al., Detection of DNA hybridization on indium tim oxide surfaces, Science Direct, Sensors and Actuators B 125 (2007), pp. 574-580.
Bao, P. et al. High Sensitivity Detection of DNA Hybridization on Microarrays Using Resonance Light Scattering, Anal. Chem. 2002, vol. 74, pp. 1792-1797.
Brown, P.O. et al., Exploring the new world of the genome with DNA microarrays, Nature Genetics Supplement, Jan. 1999, vol. 21, pp. 33-37.
Brewer, S.H. et al., Formation of Thiolate and Phosphonate Adlayers on Indium—Tin Oxide: Optical and Electronic Characterization, Langmuir, 2002, vol. 18, pp. 6857-6865.
Keena, M.A., A pourable artificial diet for rearing *Anoplophora glabripennis* (Coleoptera: Cerambycidae) and methods to optimize larval survival and synchronize development. Ann. Entomol. Soc. Am. 2005, vol. 98, pp. 536-547.
Chen, Y. et al., DNA stable isotope probing, Stable isotope probing and related technologies, ASM Press, Washington D.C., 2010.
Finzi, J.A. et al., Chapter 4: Temporal segregation of CO2 and N2 Fixation in Trichodesmium IMS-101 using Nanometer-Resolution Secondary Ion Mass Spectrometry (NanoSIMS), Aug. 2007.
National Research Council of the National Academies. 2006. Review of the Department of Energy's Genomics: GTL Program. The National Academies Press, Washington D.C.
Orphan, V.J. et al., Multiple archeal groups mediate methane oxidation in anoxic seep sediments, PNAS, 2002, vol. 99, pp. 7663-7668.
Flanagan, J.L. et al., Loss of Bacterial Diversity during Antibiotic Treatment of Intubated Patients Colonized with *Pseudomonas aeruginosa*, Journal of Clinical Microbiology, Jun. 2007, vol. 45, No. 6, pp. 1954-1962.
Reiman, D.A. The human body as microbial observatory, Nature Genetics, 2002, vol. 30, pp. 131-133.
Brinig, M. et al., Prevalence of bacteria of division TM7 in human subgingival plaque and their association with disease, Applied and Environmental Microbiology, 2003, 69(3), pp. 1687-1694.
Ouverney, C.C. et al., Single-Cell Enumeration of an Uncultivated TM7 Subgroup in the Human Subgingival Crevice, Applied and Environmental Microbiology, Oct. 2003, vol. 69, No. 10, pp. 6294-6298.
Non-Final Office Action issued for U.S. Appl. No. 12/366,476 in the name of Lawrence Livermore National Security, LLC, mail date: Apr. 23, 2012.
Non-Final Office Action issued for U.S. Appl. No. 12/366,476 in the name of Lawrence Livermore National Security, LLC, mail date: Nov. 15, 2011.
Restriction Requirement issued for U.S. Appl. No. 12/366,476 in the name of Lawrence Livermore National Security, LLC, mail date: Sep. 23, 2011.
Blackwell, M., et al., Fungi in the hidden environment: the gut of beetles, 2007, pp. 357-370, In: British Mycological Symposia: Fungi in the environment. Ed. Geoffrey Gadd. Cambridge Univ. Press.
Mayali, X. et al., Isotopic analysis of RNA microarrays shows microbial resource use profiles decoupled from phylogeny—Chip-SIP proof of concept peer-review paper (Published as Mayali, X. et al. "High-throughput isotopic analysis of RNA microarrays to quantify microbial resource use." The ISME Journal, 1-12, Dec. 8, 2011).
Mayali, X. et al., Chip-SIP for simultaneous analysis of 15N and 13C substrate incorporation by microbial taxa—Chip-SIP methodology peer-review paper (Published as Mayali, X. et al. "High-throughput isotopic analysis of RNA microarrays to quantify microbial resource use." The ISME Journal, 1-12, Dec. 8, 2011).
Mayali, X. et al. High-throughput isotopic analysis of RNA microarrays to quantify microbial resource use. The ISME Journal, 1-12, Dec. 8, 2011.
Definition of "system" retrieved from Oxford Dictionaries Online (http://www.oxforddictionaries.com/definition/system?view=uk) on Dec. 16, 2010.
International Search Report for PCT/US2009/033193 filed on Feb. 5, 2009 in the name of Lawrence Livermore National Security, LLC.
Written Opinion for PCT/US2009/033193 filed on Feb. 5, 2009 in the name of Lawrence Livermore National Security, LLC.
Brodie, E., et al., Urban aerosols harbor diverse and dynamic bacterial populations, PNAS 2007, 104: 299-304.
DeSantis, T., et al., High-density universal 16S rRNA microarray analysis reveals broader diversity than typical clone library when sampling the environment, Microbial Ecology 2007, 53: 371-383.
Lechene, C., et al., High-resolution quantitative imaging of mammalian and bacterial cells using stable isotope mass spectrometry, Journal of Biology 2006, 5: 20-49.
Stadermann, R., et al., Nanosims: the next generation ion probe for the microanalysis of extraterrestrial material, Meteoritics & Planetary Science 1999, 34: A111.
Gardner, T.J., et al. Systems for Orthogonal Self-Assembly of Electroactive Monolayers Onau and Ito: An Approach to Molecular Electronics, Journal of the American Chemical Society 1995, 117: 6927-6933.
Brodie, E., et al. Profiling Microbial Identity and Activity: Novel Applications of NanoSIMS and High Density Microarrays. Feb. 13, 2008.
G.H. McGall et al. "The Efficiency of Light-Directed Synthesis of DNA Arrays on Glass Substrates," J. Amer. Che. Soc. 1997, 119: 5081-5090.
M.A. Schena et al. "Quantitative Monitoring of Gene Expression Patterns with a Complementary DNA Microarray," Science, 1995, 270: 467-470.
M. Curreli et al. "Selective Functionalization of In2O3 Nanowire Mat Devices for Biosensing Applications," JACS 2005, 127: 6922-6923.
S. Koh et al. "Phenylphosphonic Acid Functionalization of Indium Tin Oxide: Surface Chemistry and Work Functions," J. Amer. Che. Soc. 2006, 22:6249-6255.
E. Moore et al. "Surface characterization of indium—tin oxide thin electrode films for use as a conducting substrate in DNA sensor development," Thin Solid Films, 2006, xx:xxx-xxx.
Y. Zhou et al. "Potentiometric Sensing of Chemical Warfare Agents: Surface Imprinted Polymer Integrated with an Indium Tin Oxide Electrode," Anal. Chem. 2004, 76:2689-2693.
S.H. Park et al. "A spatially resolved nucleic acid biochip based on a gradient of density of immobilized probe oligonucleotide," Analytica Chimica Acta, 2006, 564:133-140.
N.D. Popovich et al. "Electrochemical sensor for detection of unmodified nucleic acids," Talanta, 2002, 56:821-828.
Overview of Genechip Technology (retrieved on Jan. 14, 2009). Retrieved from the internet: http://www.ohsu.edu/gmsr/amc/amc_technology.html.
GeneChip Overview Flowchart (retrieved on Jan. 14, 2009). Retrieved from the internet: http://www.ohsu.edu/gmsr/amc/tech_images/chip_overview_pic.html.
Aoyagi, S., An orientation analysis method for protein immobilized on quantum dot particles, Applied Surface Science 2009, 256: 995-997.
Barison, S., et al., An investigation of cobalt oxide based nanocrystalline thin films by secondary ion mass spectrometry, Rapid Communications in Mass Spectrometry 2001, 15: 1621-1624.
Chia, W., et al., Improved optical transmittance and crystal characteristics of ZnS:TbOF thin film on Bi4Ti3O12/indium tin oxide/glass substrate by using a SiO2 buffer layer, Japanese Journal of applied Physics Part 1—Regular Papers Brief Communications & Review Papers 2006, 47: 5847-5852.
Chiou, B., et al., Effect of reactive ion etching and post-etching annealing on the electrical characteristics of indium—tin oxide silicon junctions. Journal of Materials Science—Materials in Electronics 1998, 9: 151-157.
Choi, N., et al., Novel surface modification of indium—tin—oxide films using ion implantation for organic light-emitting diodes, Japanese Journal of Applied Physics Part 1—Regular Papers Short Notes & Review Papers 2004, 43: 5516-5519.
Christensen, J., et al., Analysis of thin layers and interfaces in ITO/a-Si: H/c-Si heterojunction solar cell structures by secondary ion mass spectrometry, Thin Solid Films 2006, 511: 93-97.
Decker, F., et al., Li+ distribution into V2O5 films resulting from electrochemical intercalation reactions, Journal of the Brazilian Chemical Society 2008, 19: 667-671.

(56) References Cited

OTHER PUBLICATIONS

Jeong, J., et al., Electrostatic bonding of silicon-to-ITO coated #7059 glass using Li-doped oxide interlayer, Journal of the Korean Physical Society 1998, 33: S406-S410.

Lee, H., et al., Creating advanced multifunctional biosensors with surface enzymatic transformations, Langmuir 2006, 22: 5241-5250.

Lee, H., et al., Surface enzymes kinetics for biopolymer microarrays: a combination of Langmuir and Michaelis-Menten concepts, Langmuir 2005, 21: 4050-4057.

Kim, T., et al., The effect of buffer layer on the structural and electrical-properties of (BaSr)TiO3 thin films . . . , Journal of Applied Physics 1994, 76: 4316-4322.

Kim, T., et al., Influences of indium tin oxide layer on the properties of RF magnetron-sputtered (BaSr)TiO3 thin-films on indium tin oxide-coated glass substrate, Japanese Journal of Applied Physics Part 1—Regular Papers Short Notes & Review Papers 1993, 32: 2837-2841.

Lee, J., et al., Effect of barrier layers on the properties of indium tin oxide thin films on soda lime glass substrate, Thin Solid Films 2009, 517: 4074-4077.

Sauer, G., et al., Characterization of polymeric light-emitting-diodes by sims depth profiling analysis, Fresenius Journal of Analytical Chemistry 1995, 353: 642-646.

Shah, S., et al., Micropatterning of proteins and mammalian cells on indium tin oxide, ACS Applied Materials & Interfaces 2009, 1: 2592-2601.

Shah, S.S. et al., Exercising spatiotemporal control of cell attachment with optically transparent microelectrodes, Langmiur 2008, vol. 24, pp. 6837-6844.

Song, J., et al., Application of nano-cluster ion beam to surface smothering, etching, and ultra-shallow junction formation, Journal of the Korean Physical Society 2003, 42: S606-S610.

Sun, Y., et al., Label-free detection of biomolecules on microarrays using surface-colloid interaction, Analytical Biochemistry 2007, 361: 244-252.

Tang, C., et al., Adsorption and electrically stimulated desorption of triblock copolymer poly(propylene sulfideblethylene glycol) (PPS-PEG) from indium tin oxide (ITO) surface, Surface Science 2006, 600: 1510-1517.

Vaidya, A., et al., DNA attachment chemistry at the flexible silicone elastomer surface: Toward disposable microarrays, Langmuir 2004, 20: 11100-11107.

Wu, K. et al., Effects of ITO thin films on microstructural and photocatalytic properties of layered TiO2/ ITO films prepared via an extended deposition period, Applied Catalysis B-Environmental 2009, vol. 92, pp. 357-366.

Zhang, K., et al., Indium tin oxide films prepared by radio frequency magnetron sputtering method at a low processing temperature, Thin Solid Films 2000, vol. 376, pp. 255-263.

Wagner, M., et al., Linking microbial community structure with function: fluorescence in situ hybridization-microautoradiography and isotope arrays, Current Opinions in Biotechnology 2006, 17: 83-91.

Anderson, BJ, et al., Secondary ion mass spectrometry with a 50 nm spatial resolution applied to neural tissue. 2006 Neuroscience Meeting Planner, Atlanta: Society for Neuroscience 2006.

Boschker, H. et al., The contribution of macrophyte-derived organic matter to microbial biomass in salt-marsh sediments: stable carbon isotope analysis of microbial biomarkers, Limnology and Oceanography 1998, vol. 44(2), pp. 309-319.

Boschker, H., et al., Stable isotopes and biomarkers in microbial ecology, FEMS Microbiology Ecology 2002, 40: 85-95.

Brodie, E., et al., Bacterial community dynamics across a floristic gradient in a temperate upland grassland ecosystem, Microbial Ecology 2002, 44: 260-270.

Brodie, E., et al., Spatial characterization of the prokaryotic community structure in passalid beetle gut using a high-density 16S rRna PhyloChip, ASM General Meeting 2007b, Orlando, FL.

Breznak, J.,et al., Role of microorganisms in the digestion of lignocellulouse by termites, Annual Review of Entomology 1994, 39: 453-487.

Bryant, MP, et al., Growth of *Desulfovibrio* in lactate or ethanol media low in sulfate in association with H2-utilizing methanogenic bacteria, Appl. Environ. Microbiol. 1977, 33: 1162-1169.

Buckley, D., et al., Stable Isotope Probing with 15N Achieved by Disentangling the Effects of Genome G+C Content and Isotope Enrichment on DNA Density, Appl. Environ. Microbiol., May 2007a, vol. 73, No. 10, pp. 3189-3195.

Buckley, D., et al., Stable isotope probing with 15N2 reveals novel non-cultivated diazotrophs in soil, Appl. Environ. Microbiol., 2007b.

* cited by examiner

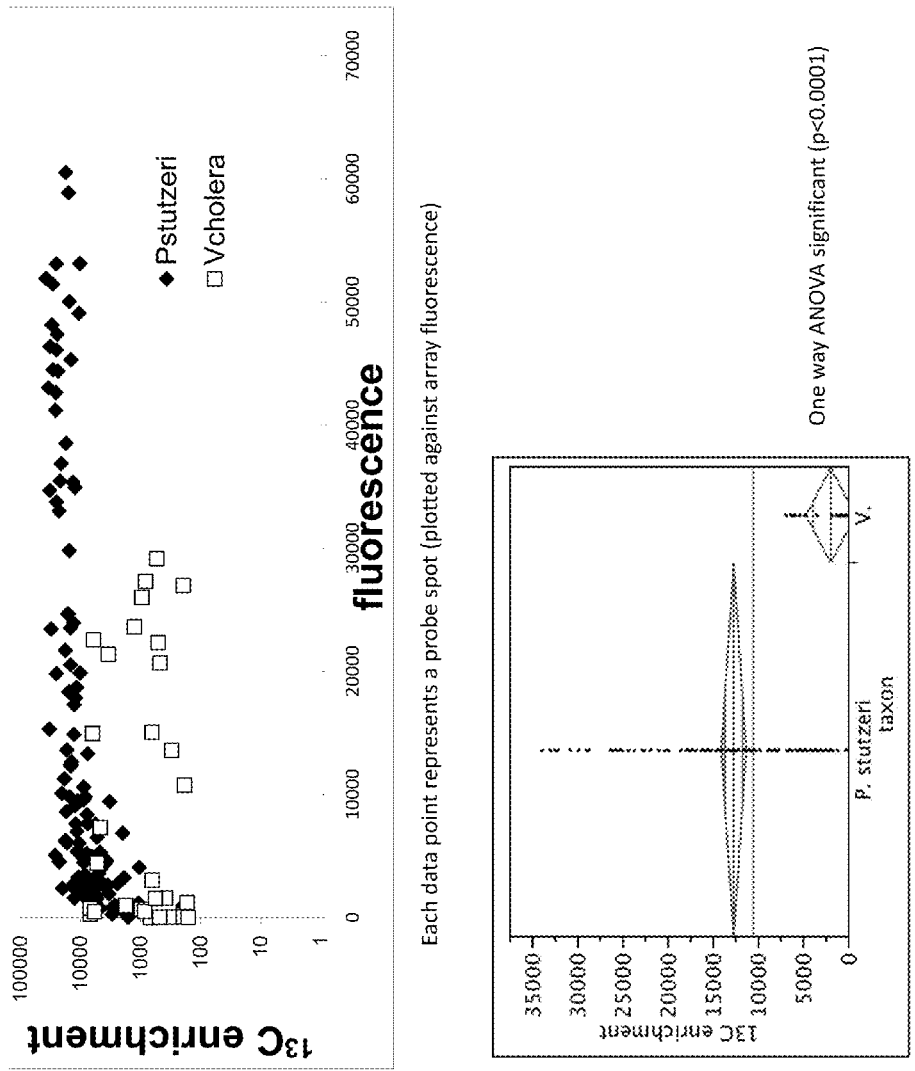

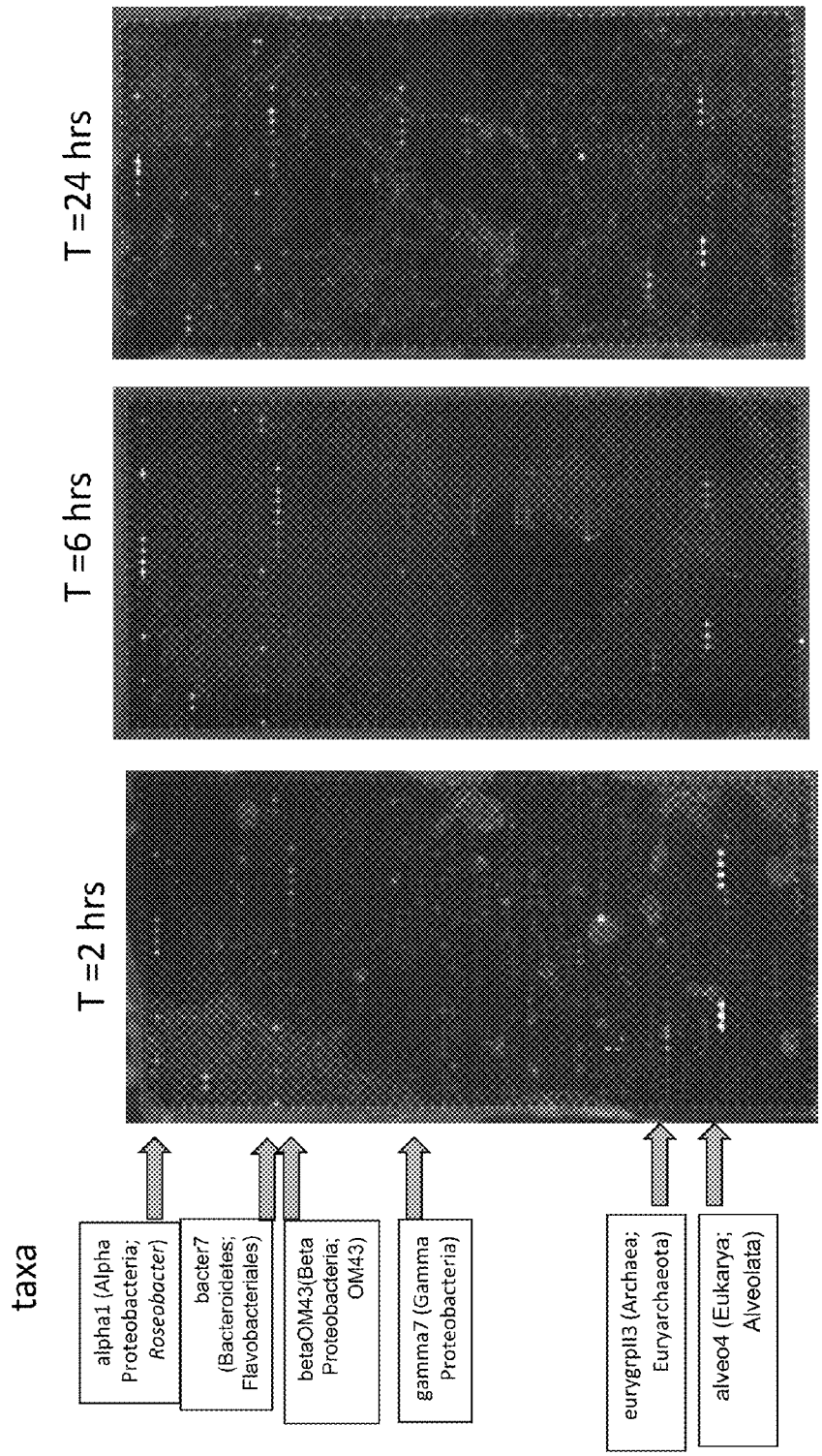

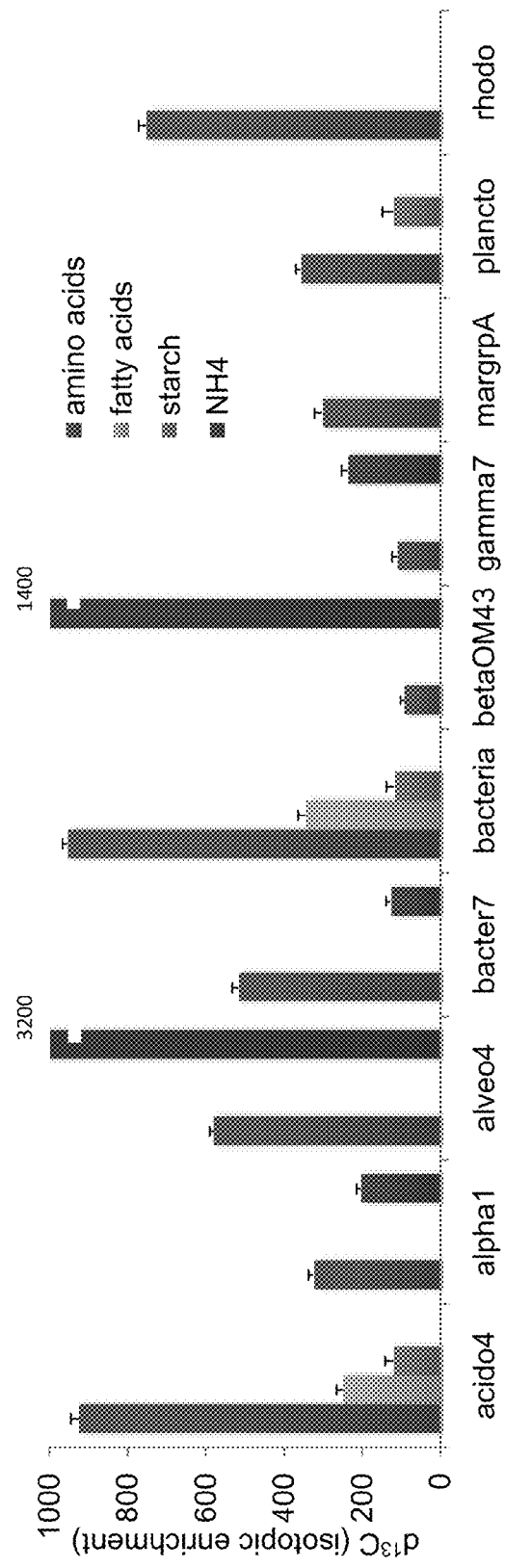

USING PHYLOGENETIC PROBES FOR QUANTIFICATION OF STABLE ISOTOPE LABELING AND MICROBIAL COMMUNITY ANALYSIS

CROSS-REFERENCE TO RELATED APPLICATIONS

This application claims priority to U.S. Provisional Patent Application No. 61/302,535, filed on Feb. 8, 2010 and to U.S. Provisional Patent Application No. 61/302,827 filed on Feb. 9, 2010, both of which are hereby incorporated by reference. This application is related to concurrently filed U.S. patent application Ser. No. 13/023,468, filed on Feb. 8, 2011, entitled "Devices, Methods and Systems for Targeted Detection," which claims priority to these same U.S. Provisional Patent applications and is hereby incorporated by reference in its entirety.

STATEMENT OF GOVERNMENTAL SUPPORT

This invention was made in part by the US DOE Office of Biological and Environmental Research Genomic Sciences research program and the LLNL Laboratory Directed Research and Development (LDRD) program with government support under Contract No. DE-AC02-05CH11231 and under Contract DE-AC52-07NA27344 awarded by the U.S. Department of Energy. The government has certain rights in the invention.

REFERENCE TO SEQUENCE LISTING AND TABLES

This application hereby incorporates the attached sequence listing in computer readable form and the attached Table 1 showing the sequences SEQ ID NOS:1-2805.

BACKGROUND OF THE INVENTION

1. Field of the Invention

The present invention relates to methods of using probes and microarrays to measure multiple different stable isotopes in nucleic acids and identification and analysis of microbial communities.

2. Related Art

Identification of microorganisms responsible for specific metabolic processes remains a major challenge in environmental microbiology, one that requires the integration of multiple techniques.

Nucleic acid stable isotope probing (SIP) techniques (5, 6) are currently the most widely used means to directly connect specific substrate utilization to microbial identity, a grand challenge in the field of microbial ecology (7). For traditional SIP, natural microbial communities are incubated in the presence of a substrate enriched in a rare stable isotope (either $^{13}C$ or $^{15}N$). The organisms, including their nucleic acids, incorporate the substrate and become isotopically enriched over time. Ultracentrifugation is used to separate isotopically enriched nucleic acids from lighter, unenriched nucleic acids for molecular analysis. In the past decade, these approaches have generated many advances in the understanding of microbial bioremediation, plant-microbe interactions and food web dynamics (8), yet they remain hindered by logistical drawbacks (9). These issues are intensified when working with density-gradient centrifugation of RNA, where the focus is on active organisms that are not necessarily replicating. Most notably, traditional DNA- and RNA-SIP isotope exposure risks fertilization effects by requiring high substrate concentrations in order to meet the sensitivity threshold of density gradient separation (in many systems>20% $^{13}C$ DNA) (10) and is extremely difficult to perform with $^{15}N$ labeled substrates (>40% $^{15}N$ DNA required) (11). Other disadvantages include long exposure times (risking community cross-feeding), low-throughput (1-2 weeks lab processing time per sample batch), and incomplete quantification. Though related culture-independent approaches also have ideal qualities such as high sensitivity or in situ resolution (e.g. $^{13}C$-PLFA (12); EL FISH (13), FISH MAR (14), isotope arrays (15)), none combines high throughput, sensitivity, taxonomic resolution, and quantitative estimates of multiple stable isotope ($^{15}N$ and $^{13}C$) incorporation.

BRIEF SUMMARY OF THE INVENTION

The present invention provides a method for quantification of stable isotope labeling using phylogenetic probes.

In another aspect, the present invention comprises community analysis using such phylogenetic probes.

The methods described have the ability to track the update of carbon, nitrogen and oxygen in ribonucleic acids and providing insight into how microorganisms metabolize these elements. The methods as described can track the uptake of carbon and nitrogen simultaneously and also be applied to oxygen. There is no other known method that can track the uptake of carbon and nitrogen simultaneously.

A method for determination of stable isotope incorporation in a organism or a community of organisms comprising the steps of: (a) supplying an organism or said community of organisms with a stable isotope labeled substrate for a defined period of time; (b) extracting RNA from the organisms; (c) fragmenting said RNA; (d) labeling a fraction the fragmented RNA with a detectable label; (e) hybridizing the labeled RNA to a set of oligonucleotide probes; (f) detecting hybridization signal strength of labeled RNA hybridized to any of the oligonucleotide probes and identifying and selecting the hybridized oligonucleotide probes as a responsive set of probes; (g) hybridizing a fraction of unlabeled RNA to a second set of oligonucleotide probes comprising the responsive set of probes; (h) detecting the unlabeled RNA hybridized to the responsive set of probes to determine the stable isotope incorporation into the organism using spectrometry or spectroscopy.

In one embodiment, the organism is a bacterium, archaea, fungi, plant, arthropod, or nematode, or other eukaryote. In a specific embodiment, the organism is a bacterium.

In one embodiment, the stable-isotope labeled substrate is $^3H$, $^{13}C$ $^{15}N$, and/or $^{18}O$.

Extraction of RNA can be carried out by physical and/or chemical cell lysis and affinity column purification. Fragmentation is generally carried out by using either enzymes or chemicals or heat or a combination of these. A fraction or aliquot of the RNA is then labeled with a fluorescent molecule or a non-fluorescent molecule. Fragmentation and labeling can occur in some embodiments concurrently.

In one embodiment, the set of oligonucleotide probes comprising an array of oligonucleotide probes attached to a substrate such as a microarray or chip. The labeled fragmented RNA can then be added to a hybridization solution and the hybridization solution contacted to the array of oligonucleotide probes to allow the labeled RNA to hybridize to the probes.

In one embodiment, the set of oligonucleotide probes comprising 16S rRNA phylogenetic oligonucleotide probes. The set of 16S rRNA phylogenetic probes further comprising probes from the 16S rRNA gene, 23S rRNA gene, 5S rRNA gene, 5.8S rRNA gene, 12S rRNA gene, 18S rRNA gene, 28S rRNA gene, gyrB gene, rpoB gene, fusA gene, recA gene, cox1 gene, nif13 gene, RNA molecules derived therefrom, or a combination thereof.

The array with the hybridized labeled RNA is imaged with a fluorescence scanner and fluorescence intensity measured for each probe feature and the detection of hybridization signal strength provides a determination of the genes present in a organism or genes and/or organisms present in the community of organisms. The detection of hybridization signal strength also provides a means for normalization of the isotope signals detected.

In one embodiment, the probes that hybridized to the labeled RNA are synthesized onto a second array of oligonucleotide probes comprising down-selected probes or responsive probes. The unlabeled RNA is hybridized to the second array hybridized unlabeled RNA are imaged with a with a secondary ion mass spectrometer and isotope ratios are measured for each probe feature.

The presently described methods provide high throughput, sensitivity, taxonomic resolution, and quantitative estimates of multiple stable isotope ($^{15}$N and $^{13}$C) incorporation. In one embodiment, microbial identity and function are connected by isolating rRNA from individual taxa through hybridization to phylogenetic probes. In one embodiment, the probes are displayed on a substrate surface, such as a custom glass microarray. After hybridization, these probe features are then analyzed for isotope enrichment. In some embodiments, the probes are analyzed using analysis techniques including but not limited to, spectrometry, spectroscopy, and quantitative secondary ion mass spectrometry imaging.

Direct NanoSIMS analysis is made possible by implementing a new surface chemistry for synthesis of DNA on conductive material. With this approach, thousands of unique phylogenetic probes assaying hundreds of taxa can be quickly analyzed from a single sample.

The present methods may be used in applications such as the evaluation of how certain organisms metabolize cellulose and what enzymes they use to do this; evaluation of what organisms have the ability to degrade pollutants in an environmental sample such as oil using water samples from the recent Gulf oil spill; or a study of carbon sequestration.

BRIEF DESCRIPTION OF THE DRAWINGS

FIG. 1: (A) fluorescence image and (B) NanoSIMS isotopic enrichment image montage of a microarray hybridized with RNA from a single bacterial strain (*Pseudomonas stutzeri*) grown on $^{13}$C glucose.

FIG. 4B shows a graph of the fluorescence intensity and $^{13}$C enrichment for *Pseudomonas stutzeri* grown on 100% $^{13}$C glucose, *Vibrio cholera* grown on 20% $^{13}$C glucose (images are not shown). A graph on the bottom panel shows one-way ANOVA analysis which demonstrates that the method is semi-quantitative because one taxa is more enriched than the other.

FIG. 5. San Francisco Bay water collected at Berkeley pier, incubated with 200 uM $^{15}$N ammonium for 24 hours. FIG. 5A shows array images of a marine microbes array designed using ARB (Ludwig, W., Strunk, O., Westram, R., Richter, L., Meier, H., Yadhukumar et al. 2004. Nucl. Acids Res. 32:1363-1371); each row represents a different taxon.

FIG. 6 is a graph showing the $^{13}$C enrichment in various taxa after incubation. San Francisco Bay water collected at Berkeley pier, incubated with 50 μM $^{13}$C amino acids (98% $^{13}$C), 30 μM fatty acids (98% $^{13}$C), and 10 mg L-1 starch (10% $^{13}$C) for 12 hours. Additional probes for larger phylogenetic groups (bacteria, Rhodobacteriacea, Planctomycetes, Marine Group A) designed using ARB.

DETAILED DESCRIPTION

Initial experiments utilized a single bacterial strain (*Pseudomonas stutzeri*) grown on $^{13}C$ glucose as the sole carbon source to determine the feasibility of successful hybridization of extracted RNA on the microarray surface, and detection of $^{13}C$ from the hybridized RNA. FIG. 1 shows images of arrays of hybridization of extracted RNA from a single bacterial species (*Pseudomonas stutzeri*) grown on $^{13}C$-glucose as the sole carbon source. Each spot (and data point) represents a distinct probe specific for *Pseudomonas*. The results show fluorescence (a measure of how much RNA is hybridized) and $^{13}C$ enrichment are positively correlated, demonstrating successful detection of labeled RNA with the Phylochip probe array.

Figure 3:
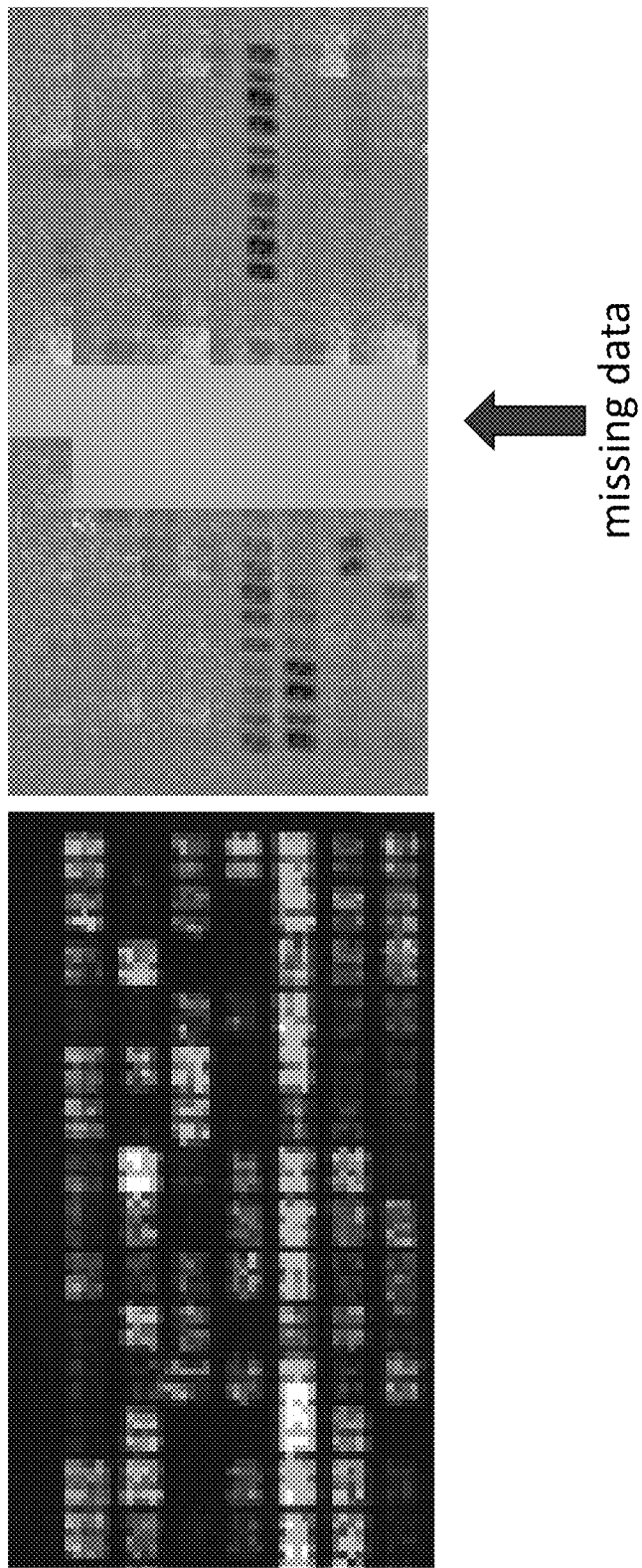
FIG. 3 shows two array images of RNA enriched with 0.5% $^{13}$C successfully detected by phylogenetic probes.

Referring now to FIG. 3, the limits of prior detection methods of isotopic enrichment are not seen using the present probes and using such analysis methods as nanoSIMS (nanoscale secondary ion mass spectrometry). Traditional SIP (Stable Isotope Probing) requires approximately 10 atom % isotopic enrichment for detection (Radajewski S, Ineson P, Parekh N R & Murrell J C 2000. *Nature* 403: 646-649). We have successfully detected hybridized RNA from *Pseudomonas stutzeri* grown in 0.5 atom % $^{13}C$ glucose. RNA enriched with 0.5% $^{13}C$ successfully detected.

Figure 4A:
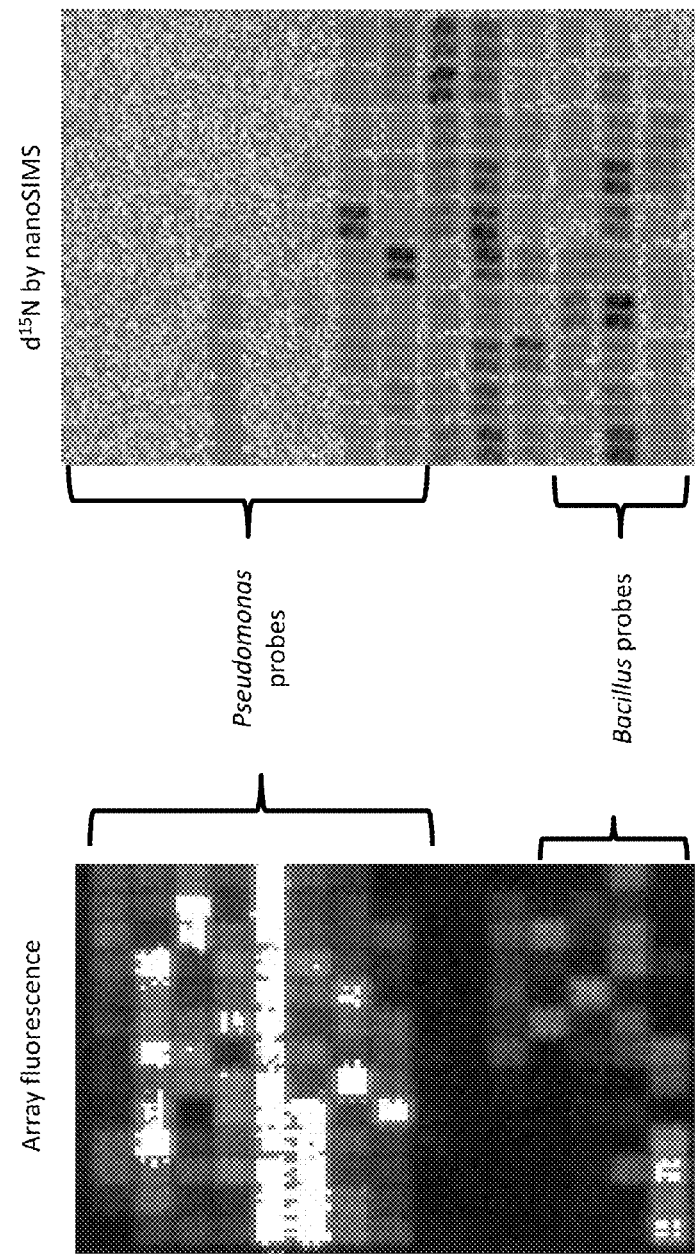
FIG. 4A shows two array images of *Pseudomonas stutzeri* grown on 25% $^{15}$N ammonium, *Bacillus cereus* grown on natural abundance ammonium; RNA extracted, mixed in equal concentrations, hybridized on array with phylogenetic probes.

FIG. 4 shows results of experiments with artificial mixed communities. Before testing the method in the environment, we mixed RNA from different bacterial strains grown on different levels of $^{13}C$ or $^{15}N$ to determine cross-hybridization potential. An experiment was carried out with a simple two-member community: *Pseudomonas stutzeri* grown on 25% $^{15}N$ ammonium, *Bacillus cereus* grown on natural abundance ammonium; RNA extracted, mixed in equal concentrations, hybridized on array featuring Phylochip probes. Experiment 2: *Pseudomonas stutzeri* grown on 100% $^{13}C$ glucose, *Vibrio cholera* grown on 20% $^{13}C$ glucose (images are not shown). The results of these two experiments shows that unlabeled taxa do not show isotopic signal in NanoSIMS, and that the present method can potentially be semi-quantitative (e.g. one taxon is more enriched than another).

Figure 5B:
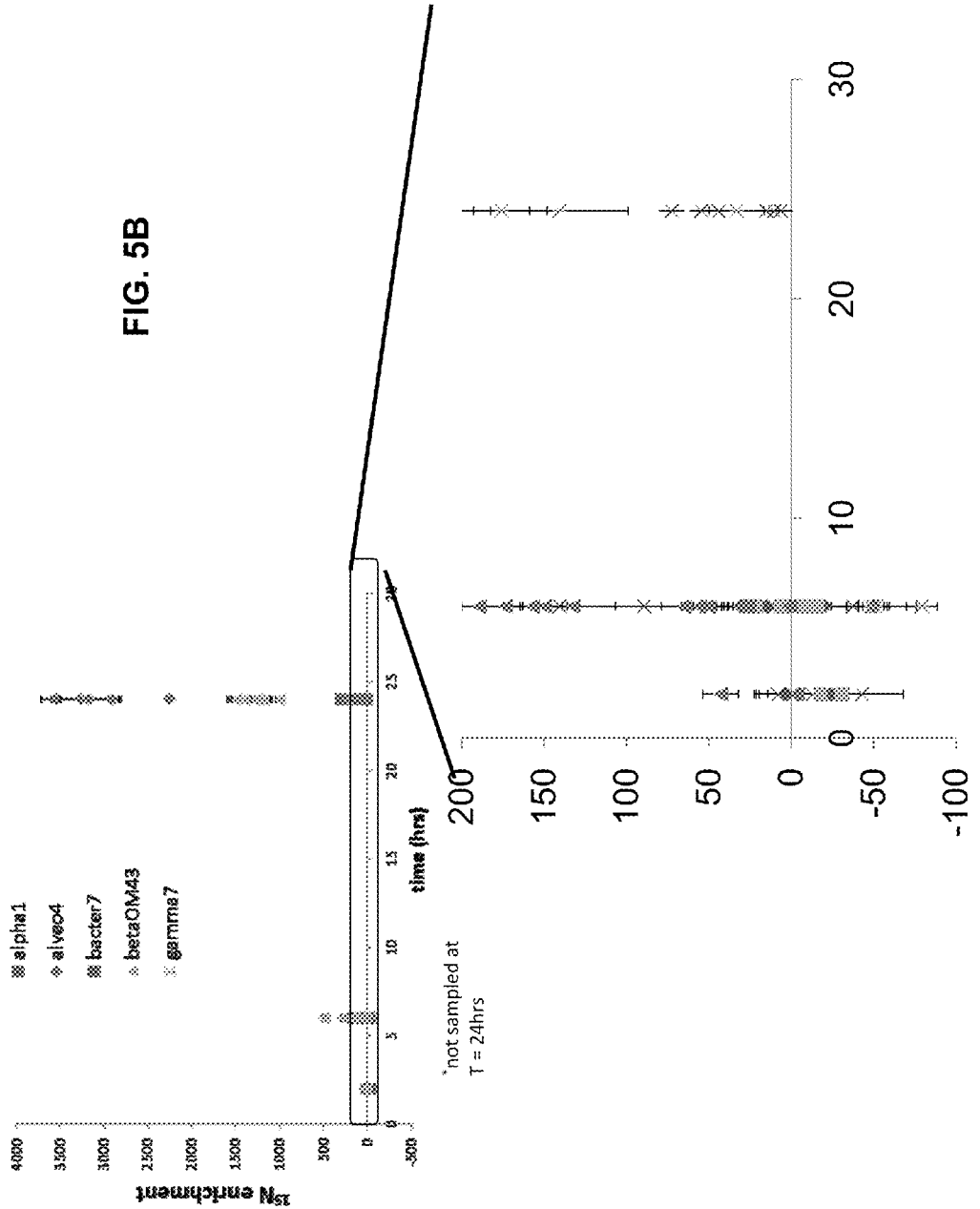
FIG. 5B is a graph showing the $^{15}$N enrichment in various taxa over time.

FIG. 5 shows the first trial of method with natural microbial communities: To apply the method to the environment, we designed a 16S rRNA and 18S rRNA microarray for common marine microbial taxa (bacteria, archaea, and protists) targeting specific phylotypes (approximately at the genus level). Estuarine samples were incubated in the presence of $^{15}N$ ammonium and sampled over time. Application of the present method using the phylogenetic probes to samples collected in San Francisco Bay water collected at Berkeley pier, incubated with 200 uM $^{15}N$ ammonium for 24 hours. Marine microbes array designed using ARB (Ludwig, W., Strunk, O., Westram, R., Richter, L., Meier, H., Yadhukumar et al. 2004. Nucl. Acids Res. 32:1363-1371); each row represents a different taxon. FIGS. 5A and 5B show that different taxa incorporate ammonia at different rates. The microarray probes are found in the accompanying Sequence Listing and identified as SEQ ID NOS:1-2805.

Little is known about organic carbon incorporation patterns in marine and estuarine environments, partly because the dominant organisms are uncultured and cannot be directly interrogated in the laboratory. We used the Chip-SIP method to test whether different taxa incorporate amino acids, fatty acids, and starch for their carbon growth requirements.

FIG. 6 shows the use of Chip-SIP method to identify organic matter utilization in estuarine microbial communities in San Francisco Bay water collected at Berkeley pier. The samples were incubated with 50 μM $^{13}C$ amino acids (98% $^{13}C$), 30 μM fatty acids (98% $^{13}C$), and 10 mg L-1 starch (10% $^{13}C$) for 12 hours. Additional probes for larger phylogenetic groups (bacteria, Rhodobacteriacea, Planctomycetes, Marine Group A) were designed using ARB. As shown in FIG. 6, different microbial taxa incorporated different substrates in situ. All tested substrates were incorporated by some bacteria. One taxon (acido4) appeared to be a generalist, while all other taxa demonstrated some degree of specificity in the substrates that were incorporated into biomass.

Thus, in one embodiment, the present invention provides methods for quantification of stable isotope labeling to observe and measure resource partitioning in microbial communities using phylogenetic probes. In one embodiment, the phylogenetic probes can be designed. In another embodiment, phylogenetic probes previously designed and provided in the previous applications hereby incorporated by reference can be used.

In one embodiment, such a method involves labeling microbial nucleic acids with stable isotope-labeled substrates (e.g., $^{13}C$-amino acids, cellulose or $^{15}NH_4$). Current methods for stable-isotope probing require large quantities of label to be incorporated into nucleic acids prior to density gradient separation (e.g. refs. Radajewski S, Meson P, Parekh N R & Murrell J C 2000. *Nature* 403: 646-649; Manefield M., Whiteley, A. S., Griffiths, R. I. and Bailey, M. J. 2002. *Appl. Environ. Microbiol.* 68:5367-73), however the necessary quantities of labeled substrate often impose a significant disturbance on system energy and metabolite flux. The presently described approach is to capture ribosomal RNA using sequence specific probes targeting 16S rRNA (Brodie, E. L., T. Z. DeSantis, D. C. Joyner, S. M. Baek, J. T. Larsen, G. L. Andersen, T. C. Hazen, P. M. Richardson, D. J. Herman, T. K. Tokunaga, J. M. M. Wan, and M. K. Firestone. 2006. *Appl. Environ. Microbiol.* 72:6288-6298), and the captured RNA is then analyzed for isotope ratios. Microarrays represent the highest-throughput approach for RNA capture; combining this with analysis methods allows isotope ratios to be determined for potentially hundreds of species within complex communities.

In some embodiments, the methods provides for a method comprising steps as the following described process. An organism or multiple organisms, such as a community of organisms, are supplied with a stable-isotope (e.g., $^{3}H$, $^{13}C$, $^{15}N$, $^{18}O$) labeled substrate for a defined period of time. RNA is extracted from the organisms or community organisms using any number of established procedures as is known in the art.

The organism RNA is fragmented using known fragmentation methods including use of enzymes, chemicals or heat or a combination of these. A first fraction or aliquot of fragmented RNA is labeled with a fluorescent molecule or a non-fluorescently labeled molecule such as biotin. This can occur concurrently with fragmentation in some embodiments.

The labeled fraction of fragmented RNA is added to a hybridization solution and hybridized to a microarray slide. Weakly bound RNA can be removed from the microarray surface by washing in solutions of varying stringency. The RNA that is hybridized to the probes are then imaged to detect hybridization signal strength and thereby quantify the labeled RNA to determine the community organism composition and also to correct and normalize the isotope signals in the RNA bound to each probe.

Currently the organism composition and normalization of isotope signal occurs on a different device than the fluorescent detection of hybridization signal strength and measurement of isotope ratio or isotope incorporation. In such a case, the fluorescent detection provides a subset of responsive probes that correlate to the presence of a specific gene and/or an organism in the sample or the community. After this detection, the organisms are identified and a down-selected probe analysis is carried out. New probes to identify an organism can be designed, or the same probes from the larger set of oligonucleotide probes can be used. For example, in some instances, sequence information generated from reverse-transcribed RNA (cDNA) from the same samples is used to select unique regions for probe design. The down-selected set of new or responsive probes is then synthesized and arrayed onto a separate substrate. A reserved fraction of RNA is then hybridized to the down-selected set of probes and imaged whereby the determination of the isotope incorporation into the organism using spectrometry or spectroscopy.

If a separate device to determine the isotope incorporation into the organism is not required, then a separate set of down-selected probes does not need to be made, but the determination made directly on the RNA hybridized to the larger set of probes.

These steps are meant to provide a basic process and one having skill the art should understand that optimizations and variations to the method are contemplated.

Examples of organisms that can be used in the present methods include but are not limited to, prokaryotic and eukaryotic organisms such as bacteria, archaea, fungi, plants, arthropods, nematodes, avians, mammals, and other eukaryotes, or viruses and phage. In one embodiment, the organism, multiple organisms or a community of organisms is bacteria, archaea, fungi, plants, arthropods, or nematodes. For larger organisms, a cell or tissue sample may be obtained and the RNA extracted from the sample.

The RNA extracted from the organisms may be the total RNA including ribosomal, messenger, and transfer RNA or it may be a subset of the total RNA.

The organisms are supplied with amino acids, cellulose or other labeled substrate containing a stable-isotope. Examples of such stable isotopes include but are limited to $^3H$, $^{13}C$, $^{15}N$, and/or $^{18}O$. Examples of such labeled substrate include $^{13}C$-amino acids, cellulose or $^{15}NH_4$ labeled substrate.

The organisms are supplied the labeled substrate for a defined period of time, such as for several minutes, hours or days. In one embodiment, a microbial community is supplied a labeled substrate for a period of 12, 18, or 24 hours.

Extraction of RNA from the organisms are generally carried out using methods known in the art. Examples of RNA extraction methods for microbial communities are provided in the Examples. In one embodiment, physical and/or chemical cell lysis and affinity column purification is used to extract RNA from the organisms or the cell or tissue sample from the organisms.

Fragmentation of the RNA is often carried out using enzymes, chemicals or heat or any combination of these. A fraction or aliquot of the fragmented RNA is labeled with a fluorescent label for suitable detection or with a label having a known binding partner to which a detectable label can be attached. In another embodiment, the fragmented RNA is labeled with a fluorescent molecule such as Alexafluor 546. In some embodiments, the fragmented RNA is labeled with biotin to which a fluorescently labeled streptavidin can be bound.

After labeling a fraction of the RNA, hybridization of the fragmented labeled RNA to a set of oligonucleotide probes is carried out. The set of oligonucleotide probes is typically attached to a solid planar substrate or on a microarray slide. However, it is contemplated that the probes may be attached to spheres, or other beads or other types of substrates. The substrates often made of materials including but not limited to, silicon, glass, metals or semiconductor materials, polymers and plastics. The substrates may be coated with other metals or materials for specific properties. In one embodiment, the substrate is coated with indium tin oxide (ITO) to provide a conductive surface for NanoSIMS analysis. The oligonucleotide probes may be present in other analysis systems, including but not limited to bead or solution multiplex reaction platforms, or across multiple platforms, for example, Affymetrix GeneChip® Arrays, Illumina BeadChip® Arrays, Luminex xMAP® Technology, Agilent Two-Channel Arrays, MAGIChips (Analysis systems of Gel-immobilized Compounds) or the NanoString nCounter Analysis System. The Affymetrix (Santa Clara, Calif., USA) platform DNA arrays can have the oligonucleotide probes (approximately 25 mer) synthesized directly on the glass surface by a photolithography method at an approximate density of 10,000 molecules per $\mu m^2$ (Chee et al., Science (1996) 274:610-614). Spotted DNA arrays use oligonucleotides that are synthesized individually at a predefined concentration and are applied to a chemically activated glass surface.

The oligonucleotide probes are probes generally of lengths that range from a few nucleotides to hundreds of bases in length, but are typically from about 10 mer to 50 mer, about 15 mer to 40 mer, or about 20 mer to about 30 mer in length.

In one embodiment, the oligonucleotide probes is a set of phylogenetic probes. In another embodiment, the phylogenetic probes comprising 16S rRNA phylogenetic probes. In one embodiment, the set of 16S rRNA phylogenetic probes further comprising probes from the 16S rRNA gene, 23S rRNA gene, 5S rRNA gene, 5.8S rRNA gene, 12S rRNA gene, 18S rRNA gene, 28S rRNA gene, gyrB gene, rpoB gene, fusA gene, recA gene, cox1 gene, nif13 gene, RNA molecules derived therefrom, or a combination thereof.

Features of phylogenetic microarrays of the invention include the use of multiple oligonucleotide probes for every known category of prokaryotic organisms for high-confidence detection, and the pairing of at least one mismatch probe for every perfectly matched probe to minimize the effect of nonspecific hybridization. In some embodiments, each perfect match probe corresponds to 1, 2, 3, 4, 5, 6, 7, 8, 9, 10, 11, 12, 13, 14, 15, 16, 17, 18, 19, 20, or more mismatch probes. These and other features, alone or in combination as described herein, make arrays of the invention extremely sensitive, allowing identification of very low levels of microorganisms.

Methods to design and select suitable probes and arrays for Chip-SIP analysis are described in detail in co-pending U.S. patent application Ser. No. 12/474,204, filed on May 28, 2009 published as US-2009-0291858-A1, and co-pending international application having application number PCT/US2010/

040106, filed on Jun. 25, 2010, both of which are incorporated by reference in their entirety for all purposes.

In one embodiment, the 16s rRNA phylogenetic probes are provided on a microarray chip, such as the G2 Phylochip or the G3 Phylochip available from Phylotech, Inc. (Second Genome, Inc., San Francisco, Calif.) and Affymetrix (Santa Clara, Calif.).

Again, the RNA that is hybridized to the probes are then imaged to detect hybridization signal strength and thereby quantify the labeled RNA to determine the community organism composition and also to correct and normalize the isotope signals in the RNA bound to each probe.

In one embodiment, for analysis for microbial composition and normalization of isotope signals, microarrays hybridized with fluorescent/biotin labeled RNA are imaged with a fluorescence scanner and fluorescence intensity measured for each probe feature or "spot". Arrays can be scanned using any suitable scanning device. Non-limiting examples of conventional microarray scanners include GeneChip Scanner 3000 or GeneArray Scanner, (Affymetrix, Santa Clara, Calif.); and ProScan Array (Perkin Elmer, Boston, Mass.); and can be equipped with lasers having resolutions of 10 pm or finer. The scanned image displays can be captured as a pixel image, saved, and analyzed by quantifying the pixel density (intensity) of each spot on the array using image quantification software (e.g., GeneChip Analysis system Analysis Suite, version 5.1 Affymetrix, Santa Clara, Calif.; and ImaGene 6.0, Biodiscovery Inc. Los Angeles, Calif., USA). For each probe, an individual signal value can be obtained through imaging parsing and conversion to xy-coordinates. Intensity summaries for each feature can be created and variance estimations among the pixels comprising a feature can be calculated.

With flow cytometry based detection systems, a representative fraction of microparticles in each sublot of microparticles can be examined. The individual sublots, also known as subsets, can be prepared so that microparticles within a sublot are relatively homogeneous, but differ in at least one distinguishing characteristic from microparticles in any other sublot. Therefore, the sublot to which a microparticle belongs can readily be determined from different sublots using conventional flow cytometry techniques as described in U.S. Pat. No. 6,449,562. Typically, a laser is shined on individual microparticles and at least three known classification parameter values measured: forward light scatter ($C_1$) which generally correlates with size and refractive index; side light scatter ($C_2$) which generally correlates with size; and fluorescent emission in at least one wavelength ($C_3$) which generally results from the presence of fluorochrome incorporated into the labeled target sequence. Because microparticles from different subsets differ in at least one of the above listed classification parameters, and the classification parameters for each subset are known, a microparticle's sublot identity can be verified during flow cytometric analysis of the pool of microparticles in a single assay step and in real-time. For each sublot of microparticles representing a particular probe, the intensity of the hybridization signal can be calculated along with signal variance estimations after performing background subtraction.

In one embodiment, responsive probe-sets are then identified based on a set criteria. See FIG. 4 For example, when using the Phylochip array of probes, the responsive probe sets are identified based on probability of probe intensities originating in the positive or background intensity distributions. High confidence subfamilies identified with expected 98.4% True Positive Rate and 2.4% False Positive Rate. Probes targeting most probable taxa in high confidence subfamilies are ranked based on quality criteria such as the lowest potential for cross-hybridization across network of putatively present taxa and the greatest difference between Perfect Match (PM) and Mismatch (MM) probe intensities. Ranked PM probes plus corresponding MM probes are synthesized onto an array and then hybridized to a reserved fraction of the RNA isolated from the organism or sample.

Various methods of mass spectrometry may be used in addition to detection using the present phylogenetic probes, such as nanoSIMS (nanoscale secondary ion mass spectrometry) or time-of-flight secondary ion mass spectrometry or other methods or means of spectrometry or spectroscopy. In other embodiments, the use of spectroscopic methods that may be employed include Raman spectroscopy or reflectance or absorbance spectroscopy. In one preferred embodiment, for analysis of isotope incorporation into organisms, microarrays hybridized with non-fluorescently labeled RNA are imaged with a secondary ion mass spectrometer, such as a SIMS or NanoSIMS device. In a specific embodiment, the NanoSIMS device is a NimbleGen MAS and the probe array is synthesized onto ITO-coated slides suitable for NanoSIMS analysis.

In some embodiments, sequence information generated from reverse-transcribed RNA (cDNA) from the same samples is used to select unique regions for probe design.

In another embodiment, the array of probes is synthesized on a substrate coated with Indium Tin Oxide (ITO) to provide a conductive surface for NanoSIMS analysis. For example, ranked PM probes plus corresponding MM probes are synthesized using the NimbleGen MAS on ITO-coated slides suitable for NanoSIMS analysis.

Current and future research will focus on the cellulose-degrading and N-fixing microorganisms found in the guts of the passalid beetle *Odontotaenius disjunctus*. This microbial community represents a naturally-selected highly-efficient lignocellulose degrading consortium, including Pichia stipitis, a yeast with high capacity for xylose fermentation (Nardi, J. B., C. M. Bee, L. A. Miller, N. H. Nguyen, S.-O. Suh, and M. Blackwell. 2006. Arthropod Struct. Devel. 35:57-68; Suh, S.-O., J. V. McHugh, D. Pollock, and M. Blackwell. 2005. Mycolog. Res. 109:261-265). RNA from beetles have been analyzed with LBNL's Phylochip (Brodie, E. L., T. Z. DeSantis, D. C. Joyner, S. M. Baek, J. T. Larsen, G. L. Andersen, T. C. Hazen, P. M. Richardson, D. J. Herman, T. K. Tokunaga, J. M. M. Wan, and M. K. Firestone. 2006. *Appl. Environ. Microbiol.* 72:6288-6298) and probes are being chosen for analysis based on signal intensity relative to background.

We have demonstrated the capability of the Chip-SIP method to link phylogenetic identity and biogeochemical function. We have achieved this by incubating natural microbial communities in the presence of isotope-enriched substrates and analyzing rRNA from those communities for isotopic enrichment in a taxon-specific manner using phylogenetic microarrays. This method can be applied to all microbial systems to advance our understanding of the microorganisms involved in the sequestration of soil and marine carbon, the deconstruction of biofuel feedstocks, biodegradation of organic pollutants and bioimmobilization of radionuclides and heavy metals.

In another embodiment, the phylogenetic probes and the present methods can be used by detecting how the labeled isotope is incorporated or expressed in an organism for resource partitioning. Observing what organisms are actively consuming of a labeled substrate can provide for identifying contaminant degraders, organisms metabolizing biofuel feed stocks and soil/marine organic matter, and optimizing or monitoring biostimulation of microbes for bioremediation as further examples.

EXAMPLE 1

Applying a Chip-SIP Method to a Marine Microbial Community

Figure 1A:
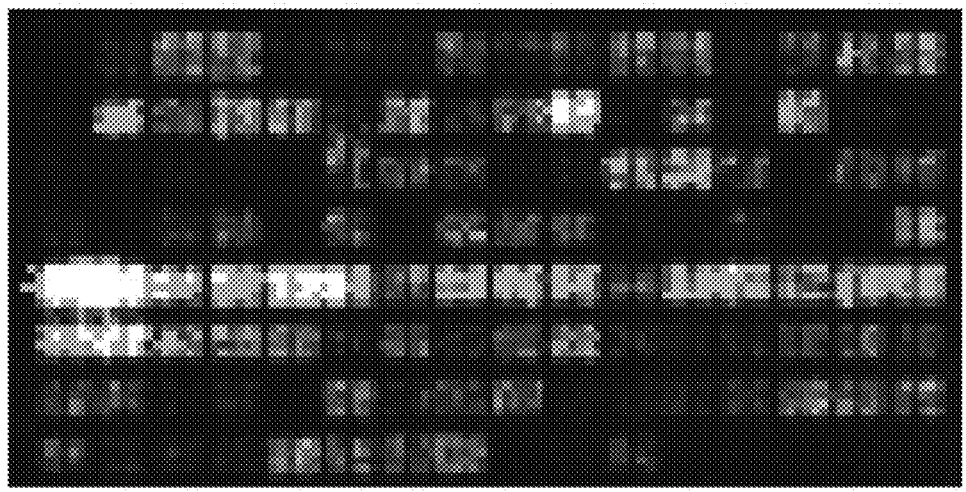
FIGS. 1A and 1B. Hybridization of extracted RNA from a single bacterial species (*Pseudomonas stutzeri*) grown on $^{13}$C-glucose as the sole carbon source. Each spot (and data point) represents a distinct probe specific for *Pseudomonas*.
Figure 1B:
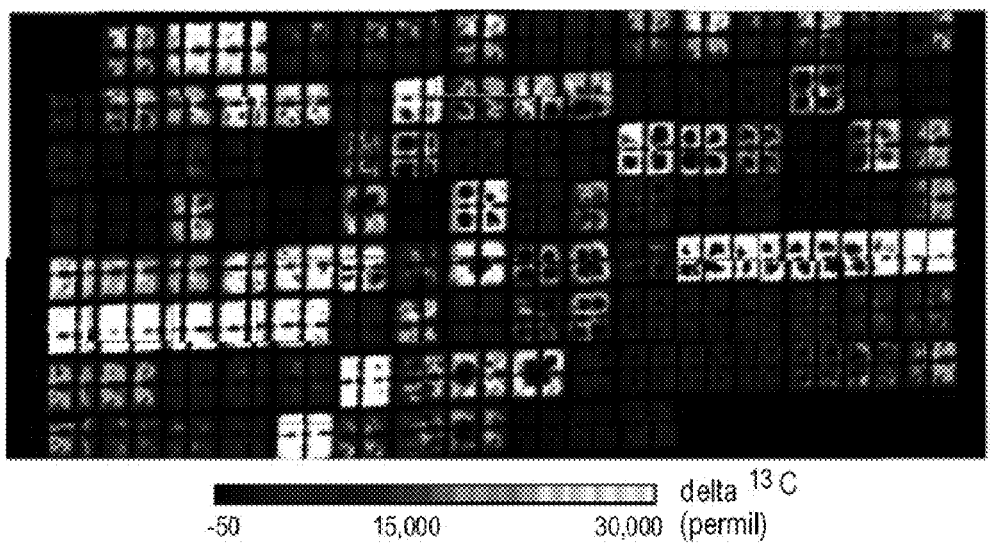
Figure 9:
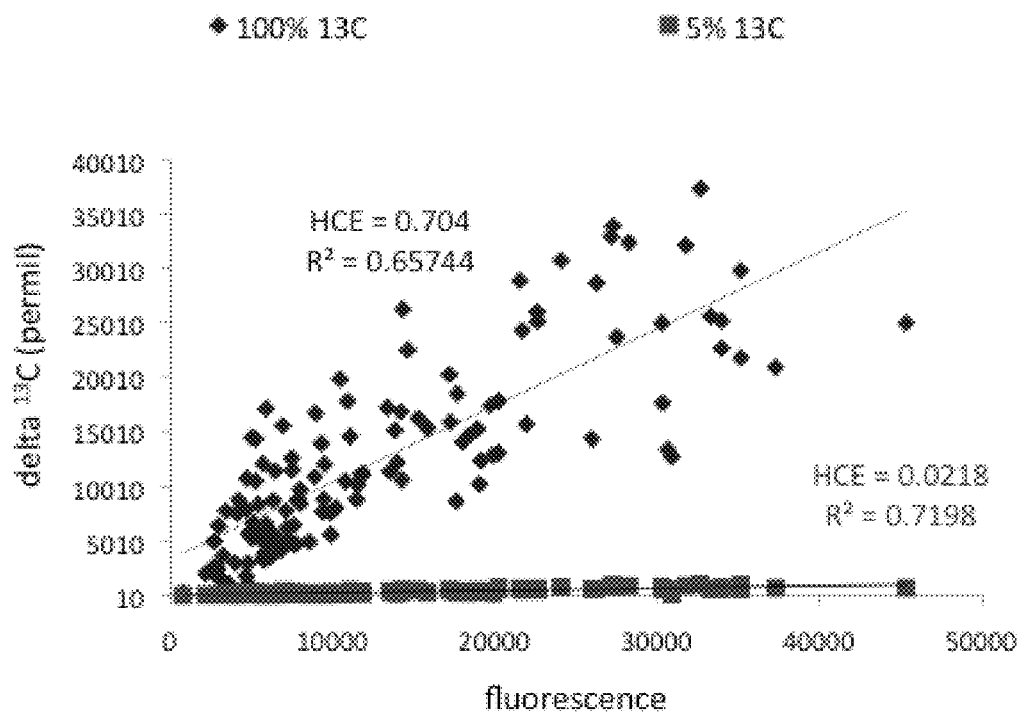
FIG. 9 shows the relationship between array fluorescence (a metric of RNA hybridization) and $^{13}$C/$^{12}$C enrichment (analyzed by NanoSIMS) of RNA from *Pseudomonas stutzeri* cultures grown separately on two levels of $^{13}$C-glucose as a sole carbon source and hybridized to an indium tin oxide (ITO) microarray. Each point represents data from a single probe location on the array. The fluorescence:enrichment relationship (i.e. hybridization corrected enrichment, "HCE") is both highly significant (see regression statistics) and different between RNA from cultures with 100% $^{13}$C (gray) versus 5% $^{13}$C enriched cultures (dark gray).

To test the chip-SIP approach, we grew a single bacterial strain (*Pseudomonas stutzeri*) in a minimal medium with $^{13}C$-glucose as the sole carbon source and extracted its RNA. After fluorescent labeling, the RNA was hybridized to a microarray probe set consisting of >100 sequences targeting different regions of the *P. stutzeri* 16S rRNA gene. Measured isotopic enrichment of these probe spots strongly depended on the efficiency of target RNA hybridization, as quantified by fluorescence (FIGS. 1A, 1B). This correlation is the result of dilution of the target RNA isotopic signal by the background of unenriched oligonucleotide probes. Thus, if less target RNA hybridizes to the array surface, higher dilution results in a lower measured isotopic enrichment. Relative isotopic enrichment of RNA from an organism can be quantified based on the slope of the enrichment:fluorescence relationship for a single probe set. We refer to this value as the hybridization-corrected enrichment (HCE; FIG. 9).

Figure 2A:
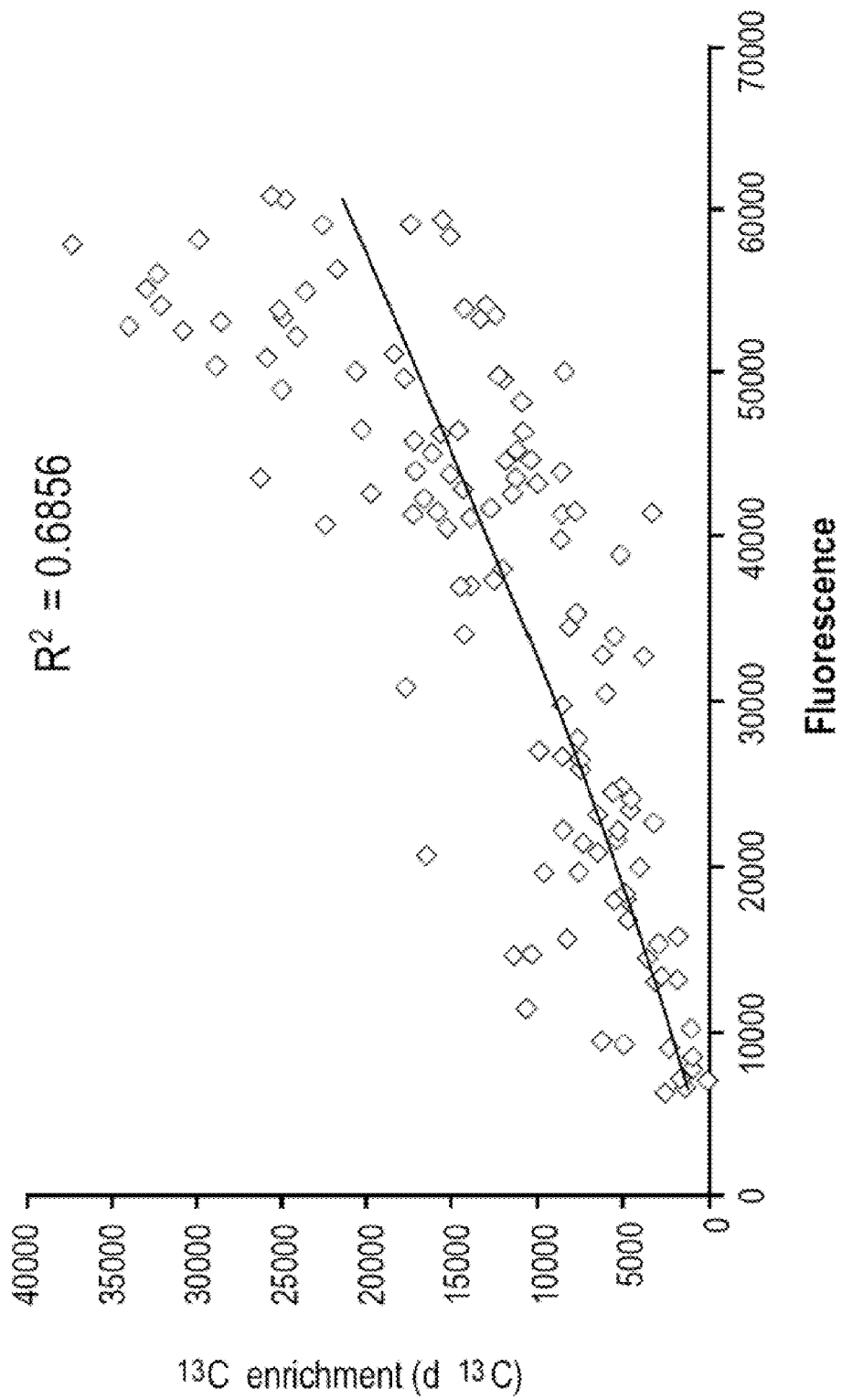
FIG. 2A is a graph that shows that fluorescence and $^{13}$C enrichment are positively correlated demonstrating successful detection of labeled RNA in FIG. 1.
Figure 2B:
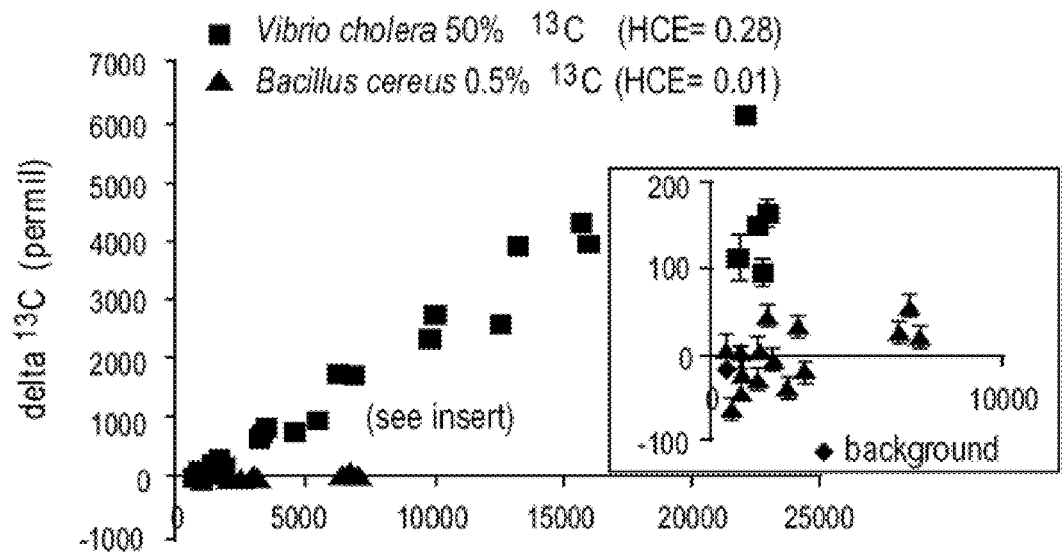
FIGS. 2B and 2C show Chip-SIP analysis of two strains with differential isotopic enrichment demonstrating clear separation of the two taxa; *Vibrio cholerae* (gray squares), *Bacillus cereus* (gray triangles), background (black diamond). HCE=hybridization-corrected enrichment. Each point represents an individual probe spot's fluorescence intensity value (a measure of fluorescence) plotted against its isotopic enrichment measured by NanoSIMS. Error bars are SEMs based on total ion counts.
Figure 2C:
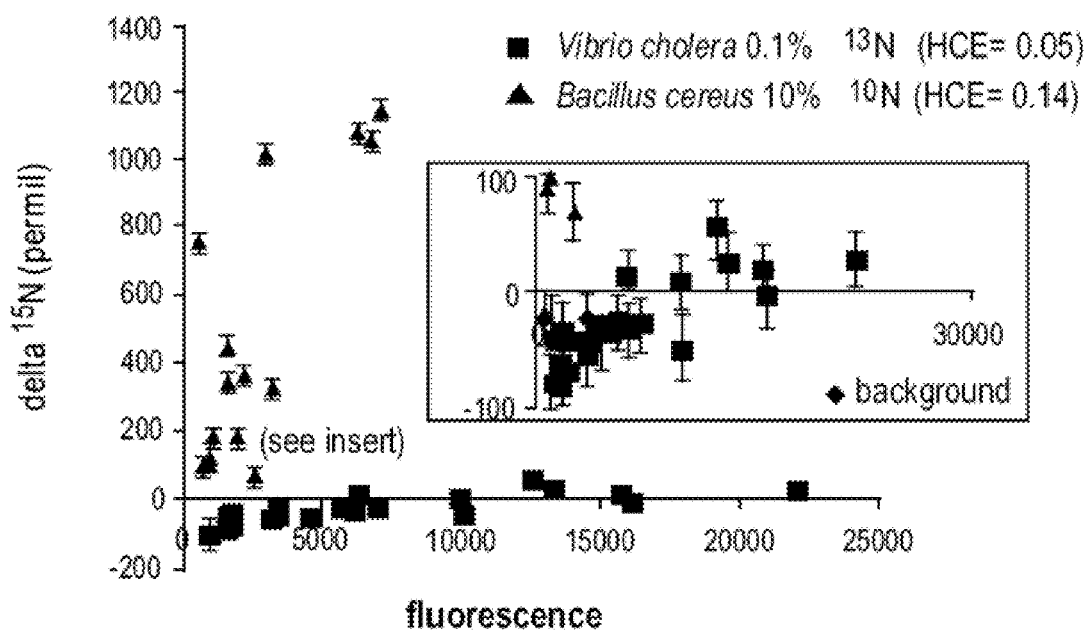

Before applying chip-SIP to natural communities, we sought to test its sensitivity and ability to discriminate a mixture of differentially labeled bacterial taxa. Two bacterial strains, *Vibrio cholerae* and *Bacillus cereus*, were grown separately to different $^{15}N$ and $^{13}C$ isotopic enrichments, then their combined RNA was hybridized to an array consisting of probe sets targeting each organism. Both $^{13}C$ (FIG. 2B) and $^{15}N$ (FIG. 2C) enrichment can easily be distinguished for each taxon based on their respective HCEs, which were significantly different (ANCOVA; p<0.0001). By integrating the results from each organism's probe set (10-20 probes/taxon), the HCE values allow the direct comparison of isotopic incorporation between two or more taxa on a single array. Notably, we successfully detected isotopic enrichments as low as 0.5% $^{13}C$ RNA (half of background $^{13}C$) and 0.1% $^{15}N$ RNA (one third of background $^{15}N$), enrichment levels that traditional SIP techniques currently cannot resolve (8, 10).

EXAMPLE 2

Materials and Methods

These present example describes the materials and methods used in the Examples.

Growth of Single Strains and Incubation of Field Samples.

Strains of *Pseudomonas stutzeri* ATTC 11607, *Vibro cholerae* ATCC 14104, and *Bacillus cereus* D17 were grown from −80° C. frozen stock in Luria-Bertani (LB) broth at 37° C. until late log phase, and transferred into $^{12}C$ glucose-amended M9 minimal medium until late log phase. Then, a 10 µl aliquot was inoculated into 10 ml of M9 enriched in $^{13}C$ glucose and/or $^{15}N$ ammonium and the culture was again grown until late log phase. An enrichment of 10% $^{13}C$ indicates 10% of the glucose in the medium was 99% enriched in $^{13}C$, and 90% of the glucose had natural carbon (1.1% $^{13}C$ and 98.9% $^{12}C$). Cells were centrifuged, washed, and frozen at −80° C. Bulk measurements (by Isotope Ratio Mass Spectrometry) showed that *Pseudomonas* cells grown in full $^{13}C$ glucose were enriched between 680,000 and 900,000 permil, equivalent to 90 atm %.

For field experiments, surface water was collected at the public pier in Berkeley, Calif. USA (37°51'46.67"N, 122°19'3.23"W) and immediately brought back to the laboratory i cooler. Glass bottles (500 ml) were filled without air space and dark incubated at 14° C. For the first set of experiments, samples were simultaneously incubated with 50 µM 99 atm % $^{13}C$ glucose and 200 µM 99 atm % $^{15}N$ ammonium, and subsamples harvested after 2, 6, and 24 hrs by filtration through a 0.22 polycarbonate filter which was then immediately frozen at −80° C. Background concentrations of ammonium in San Francisco bay range from 1-14 µM (1); typically estuarine glucose concentrations are 5-100 nM (2). For the second set of experiments, water samples were incubated as described above with 8 µM mixed amino acids (99 atm % $^{13}C$ and 99 atm % $^{15}N$ labeled; Omicron), 500 µg L$^{-1}$ algal fatty acids (98 atm % $^{13}C$; Omicron), or 50 µg L$^{-1}$ nucleic acids (90 atm % $^{13}C$; RNeasy extract from $^{13}C$ *Pseudomonas stutzeri*), collected by filtration after 12 hrs and frozen at −80° C. These substrate additions were designed to result in concentrations at the high end of what is typically measured in estuarine environments: 2-7 µM amino acids (3), 25 µg L$^{-1}$ fatty acids (4) and 10 µg L$^{-1}$ DNA (5).

RNA Extraction and Labeling.

RNA from pelleted cells (laboratory strains) and filters (field samples) was extracted with the Qiagen RNEasy kit according to manufacturer's instructions, with slight modifications for the field samples. Filters were incubated in 200 µL TE buffer with 5 mg mL$^{-1}$ lysozyme and vortexed for 10 min at RT. RLT buffer (800 µL, Qiagen) was added, vortexed, centrifuged, and the supernatant was transferred to a new tube. Ethanol (560 µl) was added, mixed gently, and the sample was applied to the provided minicolumn. The remaining manufacturer's protocol was subsequently followed. At this point, RNA samples were split: one fraction saved for fluorescent labeling (see below), the other was kept unlabeled for NanoSIMS analysis. This procedure was used because the fluorescent labeling protocol introduces background carbon (mostly $^{12}C$) that dilutes the $^{13}C$ signal (data not shown). Alexafluor 546 labeling was done with the Ulysis kit (Invitrogen) for 10 min at 90° C. (2 µL RNA, 10 µL labeling buffer, 2 µL Alexafluor reagent), followed by fragmentation. All RNA (fluorescently labeled or not) was fragmented using 5× fragmentation buffer (Affymetrix) for 10 min at 90° C. before hybridization. Labeled RNA was purified using a SpinOUT™ minicolumn (Millipore), and RNA was concentrated by ethanol precipitation to a final concentration of 500 ng µL$^{-1}$.

Target Taxa Selection by PhyloC Hip Analysis and De Novo Probe Design.

RNA extracts from SF Bay SIP experiment samples were treated with DNAse I and reverse-transcribed to produce cDNA using the Genechip Expression 3' amplification one-cycle cDNA synthesis kit (Affymetrix). The cDNA was PCR amplified with bacterial and archaeal primers, fragmented, fluorescently labeled, and hybridized to the G2 PhyloChip which is described by E. L. Brodie et al., in "Application of a high-density oligonucleotide microarray approach to study bacterial population dynamics during uranium reduction and reoxidation." *Appl. Environ. Microbiol.* 72, 6288 (2006) hereby incorporated by reference, and commercially available from Affymetrix (Santa Clara, Calif.) through Second Genome (San Francisco, Calif.).

Taxa (16S operating taxonomic units, OTU) considered to be present in the samples were identified based on 90% of the probes for that taxon being responsive, defined as the signal of the perfect match probe>1.3 times the signal from the mismatch probe. From approximately 1500 positively identified taxa, we chose a subset of 100 taxa commonly found in marine environments to target with chip-SIP. We also did not target OTUs previously identified from soil, sewage, and bioreactors as our goal was to characterize the activity of marine microorganisms. Using the Greengenes database (7)

implemented in ARB (8), we designed 25 probes (25 bp long), to create a 'probe set' for each taxon (Table 1; SEQ ID NOS: 1-2805), as well as general probes for the three domains of life. Probes for single laboratory strains (*Pseudomonas stutzeri, Bacillus cereus*, and *Vibrio cholerae*) were also designed with ARB (Table 1).

Microarray Synthesis and Hybridization.

A custom conductive surface for the microarrays was used to eliminate charging during SIMS analysis. Glass slides coated with indium-tin oxide (ITO; Sigma) were treated with an alkyl phosphonate hydroxy-linker (patent pending) to provide a starting substrate for DNA synthesis. Custom-designed microarrays (spot size=17 μm) were synthesized using a photolabile deprotection strategy (9) on the LLNL Maskless Array Synthesizer (Roche Nimblegen, Madison, Wis.). Reagents for synthesis (Roche Nimblegen) were delivered through the Expedite (PerSeptive Biosystems) system. For quality control (to determine that DNA synthesis was successful), slides were hybridized with complimentary *Arabidopsis* calmodulin protein kinase 6 (CPK6) labeled with Cy3 (Integrated DNA Technologies), which hybridized to fiducial marks, probe spots with the complementary sequence synthesized throughout the array area. Probes targeting microbial taxa were arranged in a densely packed formation to decrease the total area analyzed by imaging secondary ion mass spectrometry (NanoSIMS). For array hybridization, RNA samples in 1× Hybridization buffer (NimbleGen) were placed in Nimblegen X4 mixer slides and incubated inside a Maui hybridization system (BioMicro® Systems) for 18 hrs at 42° C. and subsequently washed according to manufacturer's instructions (NimbleGen). Arrays with fluorescently labeled RNA were imaged with a Genepix 4000B fluorescence scanner at pmt=650 units. Arrays with non-fluorescently labeled RNA were marked with a diamond pen and also imaged with the fluorescence scanner to subsequently navigate to the analysis spots in the NanoSIMS. These spots were observable in the fluorescence image because fiducial probe spots were synthesized around the outline of the area to be analyzed by NanoSIMS. Prior to NanoSIMS analysis, samples were not metal coated to avoid further dilution of the RNA's isotope ratio or loss of material. Slides were trimmed and mounted in custom-built stainless steel holders.

NanoSIMS Analyses.

Secondary ion mass spectrometry analysis of microarrays hybridized with $^{13}$C and/or $^{15}$N rRNA was performed at LLNL with a Cameca NanoSIMS 50 (Cameca, Gennevilliers, France). A Cs+ primary ion beam was used to enhance the generation of negative secondary ions. Carbon and nitrogen isotopic ratios were determined by electrostatic peak switching on electron multipliers in pulse counting mode, alternately measuring $^{12}C^{14}N^-$ and $^{12}C^{15}N^-$ simultaneously for the $^{15}N/^{14}N$ ratio, and then simultaneously measuring $^{12}C^{14}N^-$ and $^{13}C^{14}N^-$ for the $^{13}C/^{12}C$ ratio. We used this peak switching strategy because the secondary ion count rate for the CN$^-$ species in these samples is 5-10 times higher than any of the other carbon species (e.g., C$^-$, CH$^-$, C$_2^-$), and therefore higher precision was achieved even though total analytical time was split between the two CN$^-$ species at mass 27. If only one isotopic ratio was needed, peak switching was not performed. Mass resolution was set to ~10,000 mass resolving power to minimize the contribution of isobaric interferences to the species of interest (e.g., $^{11}B^{16}O^-$ contribution to $^{13}C^{14}N^-$<1/100; $^{13}C_2^-$ contribution to $^{12}C^{14}N^-$<1/1000). Analyses were performed in imaging mode to generate digital ion images of the sample for each ion species. Analytical conditions were optimized for speed of analysis, ability to spatially resolve adjacent hybridization locations, and analytical stability. The primary beam current was 5 to 7 pA Cs+, which yielded a spatial resolution of 200-400 nm and a maximum count rate on the detectors of ~300,000 cps $^{12}C^{14}N$. Analysis area was 50×50 μm$^2$ with a pixel density of 256×256 with 0.5 or 1 ms/pixel dwell time. For peak switching, one scan of the analysis area was made per species set, resulting in two scans per analytical cycle. With these conditions, reproducible secondary ion ratios could be measured for a maximum of 4 cycles through the two sets of measurements before the sample was largely consumed. Data were collected for 2 to 4 cycles. Based on total counts for the analyzed cycles, we achieved precision of 2-3% for $^{13}C^{14}N$ and 1-4% for $^{15}N^{12}C$, depending on the enrichment and hybridization intensity. A single microarray analysis of approximately 2500 probes, with an area of 0.75 mm$^2$ and the acquisition of 300 images, was carried out using the Cameca software automated chain analysis in 16 hours. Ion images were stitched together and processed to generate isotopic ratios with custom software (LIMAGE, L. Nittler, Carnegie Institution of Washington). Ion counts were corrected for detector dead time on a pixel by pixel basis. Hybridization locations were selected by hand or with the auto-ROI function, and ratios were calculated for the selected regions over all cycles to produce the location isotopic ratios. Isotopic ratios were converted to delta values using δ=[(R$_{meas}$/R$_{standard}$)−1]×1000, where R$_{meas}$ is the measured ratio and R$_{standard}$ is the standard ratio (0.00367 for $^{15}N/^{14}N$ and 0.011237 for $^{13}C/^{12}C$). Data were corrected for natural abundance ratios measured in unhybridized locations of the sample.

Data Analyses.

For each taxon, isotopic enrichment of individual probe spots was plotted against fluorescence and the linear regression slope was calculated with the y-intercept constrained to natural isotope abundances (zero permil for $^{15}$N data and −20 permil for $^{13}$C data). This calculated slope (permil/fluorescence), which we refer to as the 'hybridization-corrected enrichment (HCE), is a metric that can be used to compare the relative incorporation of a given substrate by different taxa. It should be noted that due to the different natural concentrations of $^{13}$C and $^{15}$N, and more importantly, different background contributions from the microarray, HCEs for $^{15}$N substrates and $^{13}$C substrates are not comparable. To construct a network diagram (e.g. FIG. 8A), taxa with HCEs having standard errors not overlapping with zero and with >30 permil enrichment were included (all others were discarded) using Cytoscape software (10). For analyses of marine bacterial genomic information, genomes of marine bacterial isolates were selected in the Joint Genome Institute's Integrated Microbial Genomes (IM-G) database and word-searched for the presence of amino acid, fatty acid, and nucleoside transporters and extracellular nucleases. Results are summarized in Table S2. For phylogenetic relationships (FIG. 8B), the global 16S rRNA phylogeny in the Greengenes database (7) was opened in ARB (8) and all taxa except the targets of the array analysis were removed with the taxon pruning function.

EXAMPLE 3

Viability of Chip-SIP on a San Francisco Bay Sample

Figure 10:
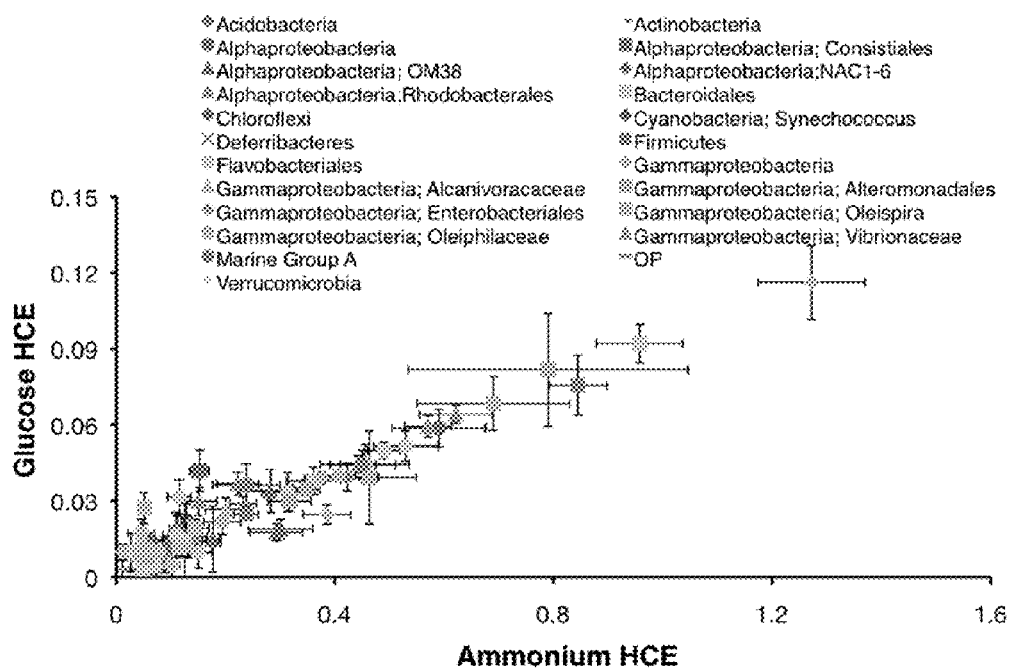
FIG. 10: Relative incorporation of $^{15}$N-ammonium and $^{13}$C-glucose detected by chipSIP for a natural estuarine microbial community from the San Francisco Bay. Units are the slope of permil isotope enrichment over fluorescence (HCE=hybridization corrected enrichment). Each point is the average of probe spots representing the identified phyla. Error bars represent the standard error of the slope calculation.
Figure 11:
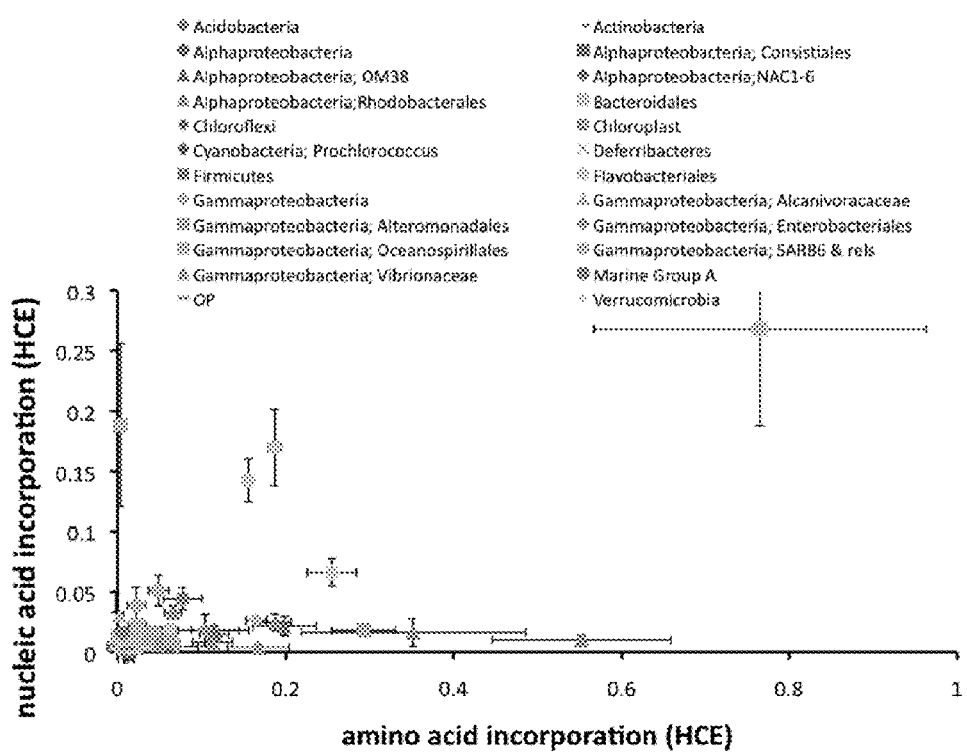
FIG. 11: Relative incorporation of amino acids and nucleic acids detected by chip-SIP for a natural estuarine microbial community from the San Francisco Bay. Units are the slope of permil enrichment over fluorescence (HCE=hybridization corrected enrichment).
Figure 12:
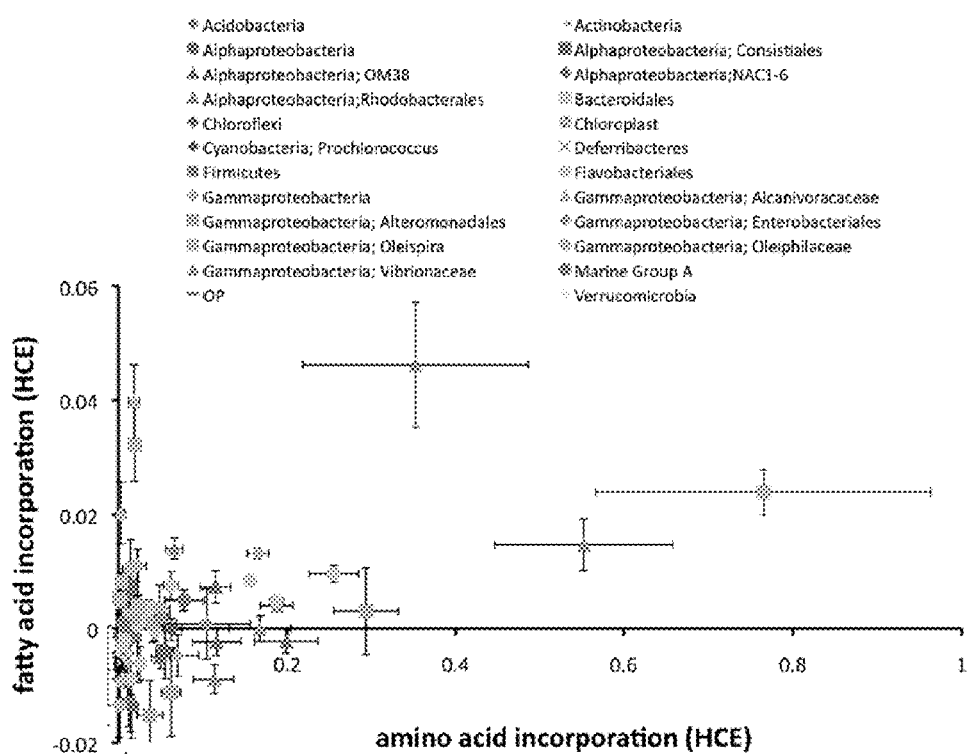
FIG. 12: Relative incorporation of amino acids and fatty acids detected by chip-SIP for a natural estuarine microbial community. Units are the slope of permil enrichment over fluorescence (HCE=hybridization corrected enrichment).
Figure 13:
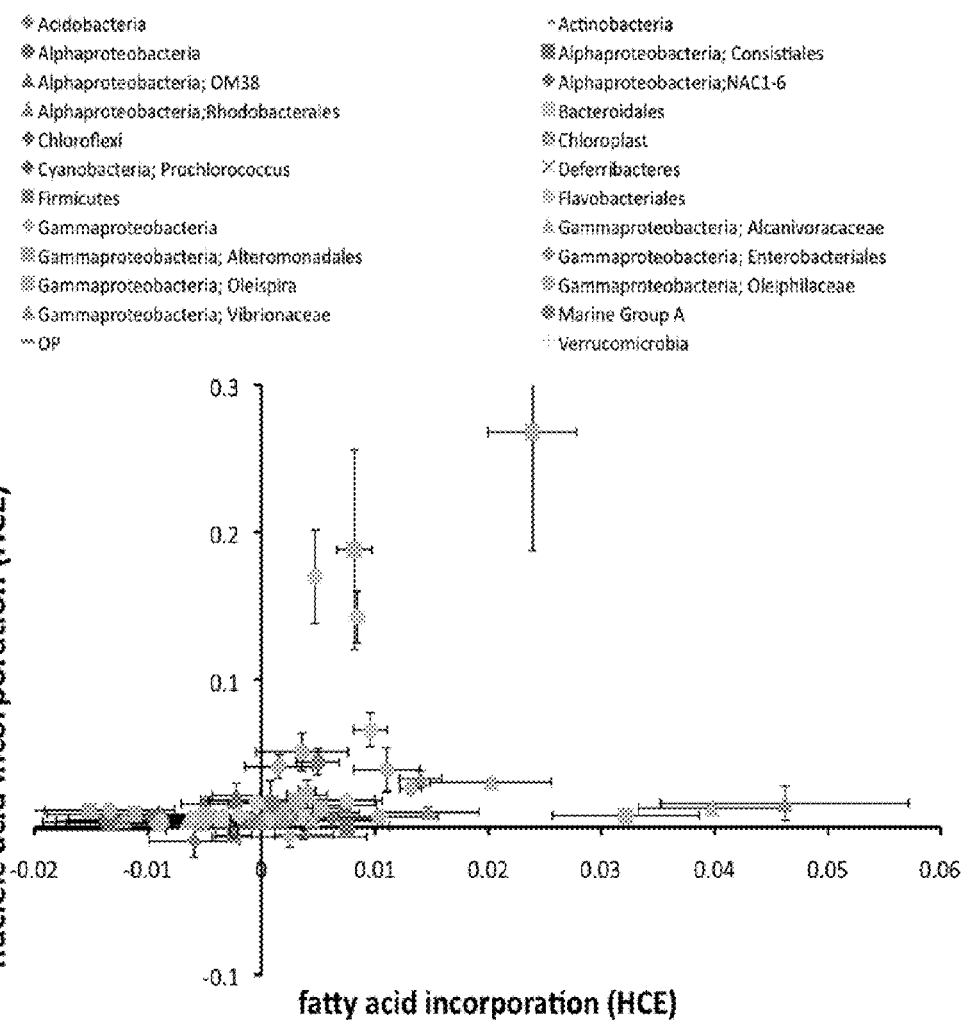
FIG. 13: Relative incorporation of fatty acids and nucleic acids detected by chip-SIP for a natural estuarine microbial community. Units are the slope of permil enrichment over fluorescence (HCE=hybridization corrected enrichment).

In a second set of experiments, we tested the viability of chip-SIP for a diverse natural community, using a sample from the San Francisco (SF) Bay, a eutrophic estuary. The bay water was incubated in the dark with micromolar concentrations of $^{15}$N ammonium and $^{13}$C glucose for 24 hrs, a timescale long enough to ensure detectable isotopic labeling of the dominant active community. We expected the most active taxa to incorporate these substrates, as they are of small molecular weight, do not require extracellular breakdown before uptake, and directly feed into central carbon and nitrogen metabolic pathways. This chip-SIP array consisted of 2500 probes targeting 100 microbial taxa selected from a PhyloChip analysis of the same sample (Table 1; 16). Based on RNA fluorescence, we positively detected 73 taxa. As in the experiments with laboratory cultures, the relationship between fluorescence and isotopic incorporation for each taxon was positive and linear for both $^{15}$N and $^{13}$C (e.g. FIGS. 7A, 7B for three Rhodobacteraceae probes sets), demonstrating that different members of the same bacterial families could incorporate different levels of $^{15}$N from ammonium and $^{13}$C from glucose. Though these substrate concentrations may have favored copiotrophs (17), we detected the model oligotroph *Pelagibacter* (FIGS. 10, 18). This result demonstrates that even oligotrophic organisms retained a presence and detectable biogeochemical activity in this highly eutrophic environment.

Figure 7:
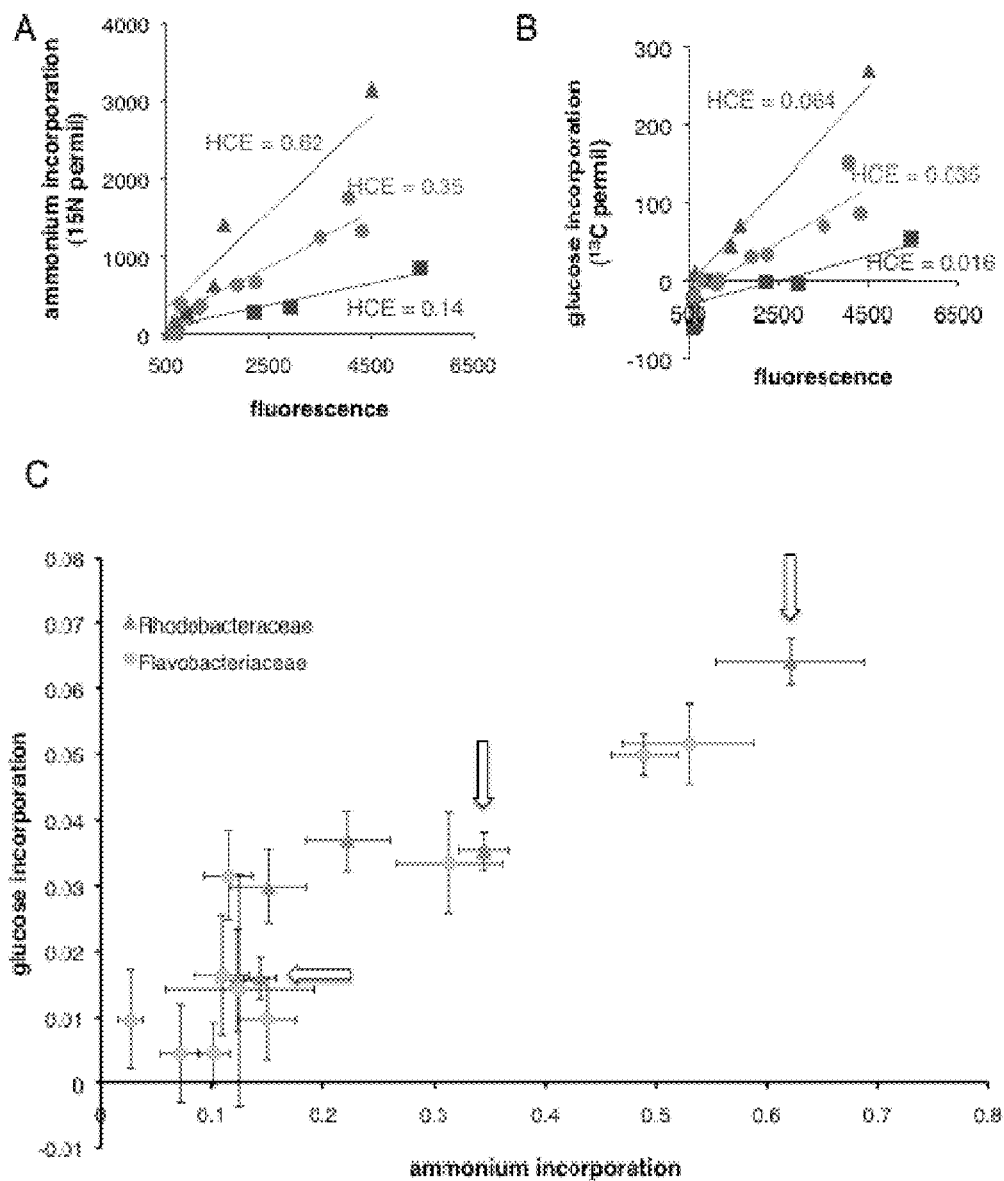
FIG. 7 shows substrate incorporation detected by chip-SIP for a SF Bay estuarine microbial community incubated with 200 μM$^{15}$N ammonium and 50 μM$^{13}$C glucose for 24 hrs; A) $^{15}$N ammonium and B) $^{13}$C glucose incorporation for 3 taxa within the bacterial family Rhodobacteriaceae; each point is derived from a single probe spot's isotopic enrichment value plotted against fluorescence (a measurement of hybridization); C) relationship between ammonium and glucose incorporation for 16 taxa from two bacterial families; HCE=hybridization-corrected enrichment; arrows indicate taxa plotted in A and B.

An advantage of chip-SIP's ability to detect $^{13}$C and $^{15}$N on the same array is its potential to uncover physiological diversity, based on the relative incorporation of two substrates incubated simultaneously. Our ability to measure taxon-specific substrate incorporation allowed us to reveal that the relationship between ammonium and glucose incorporation was linear: organisms with high ammonium incorporation (high $^{15}$N HCEs) also exhibited high glucose incorporation (high $^{13}$C HCEs), and vice versa (FIGS. 7C, 10). A previous experiment illustrated an analogous pattern using lower resolution bulk measurements comparing marine water samples amended with different levels of glucose and ammonium(19). The authors found that community wide C/N assimilation was constant, irrespective of the absolute amount of substrates added. Our data revealed that this pattern also occurs within the same water sample, in which different microbial populations represent physiologically distinct components of the community. We also showed that relatively broad phylogenetic clades (family level, in this case) did not correspond to substrate incorporation patterns: members of the same bacterial family were scattered throughout the HCE distribution. For example, members of the Flavobacteriaceae did not incorporate less (or more) substrate than the Rhodobacteraceae, because within each family, there were taxa with both high and low incorporation (FIG. 7C).

EXAMPLE 4

Viability of Chip-SIP on a San Francisco Bay Sample

Marine microorganisms, most of which remain uncultivated, control the release, transformation, and remineralization of ~50 Gigatons of fixed carbon annually, resulting in biological carbon sequestration to the deep sea (P. Falkowski et al., The global carbon cycle: a test of our knowledge of earth as a system. *Science* 290, 291 (2000)). Identifying the microbes responsible for C cycling processes in the marine microbial loop and the factors affecting C cycling rates in marine ecosystems is a critical precursor to the development of predictive models of microbial responses to environmental perturbations (e.g., pollution, nutrient inputs or global change). Currently, the ecological niches of marine microorganisms, heterotrophic bacteria in particular, are often categorized as "copiotrophic" or "oligotrophic" depending on their predominant location, for example high-nutrient and particle-rich coasts versus low-nutrient open oceans, or warm, well-lit, productive surface waters versus the cold, dark deep (S. J. Giovannoni, U. Stingl, Molecular diversity and ecology of microbial plankton. *Nature* 437, 343 (2005)). The advent of 16S rRNA sequencing and environmental genomics have revolutionized marine microbial ecology by assembling a "parts list" of genetic diversity (M. S. Rappé, P. F. Kemp, S. J. Giovannoni, Phylogenetic diversity of marine coastal picoplankton 16S rRNA genes cloned from the continental shalf off Cape Hatteras, N.C. *Limnol. Oceanogr.* 42, 811 (1997)) and functional capability (E. F. DeLong et al., Community genomics among stratified microbial assemblages in the ocean's Interior. *Science* 311, 496 (2006)), but the goal of linking phylogenetic identity and in situ functional roles of uncultivated microorganisms remains largely unattained. In addition, while the comparative 'omics strategy to gain ecosystem functional information has been fruitful, it relies on sequence comparison rather than direct measurements of biogeochemical activity. To gain a mechanistic understanding of microbial control of biogeochemical cycles in the ocean and elsewhere, it is necessary to move beyond microbial diversity or metagenomic surveys towards trait-based functional studies that directly and simultaneously measure the biogeochemical activities of hundreds of microbial taxa in their native environment.

In a third set of experiments, we compared predicted and actual substrate use of three organic substrates by a diverse natural community, an example of the type of experiment that can eventually lead to more realistic models of marine food web structure (20). In this case, we applied chip-SIP to another set of SF Bay samples incubated separately with isotopically-labeled amino acids, nucleic acids, and fatty acids. These substrates make up a significant proportion of photoautotrophic biomass (21) that provide the majority of fixed carbon substrates for the marine microbial food web.

Figure 8A:
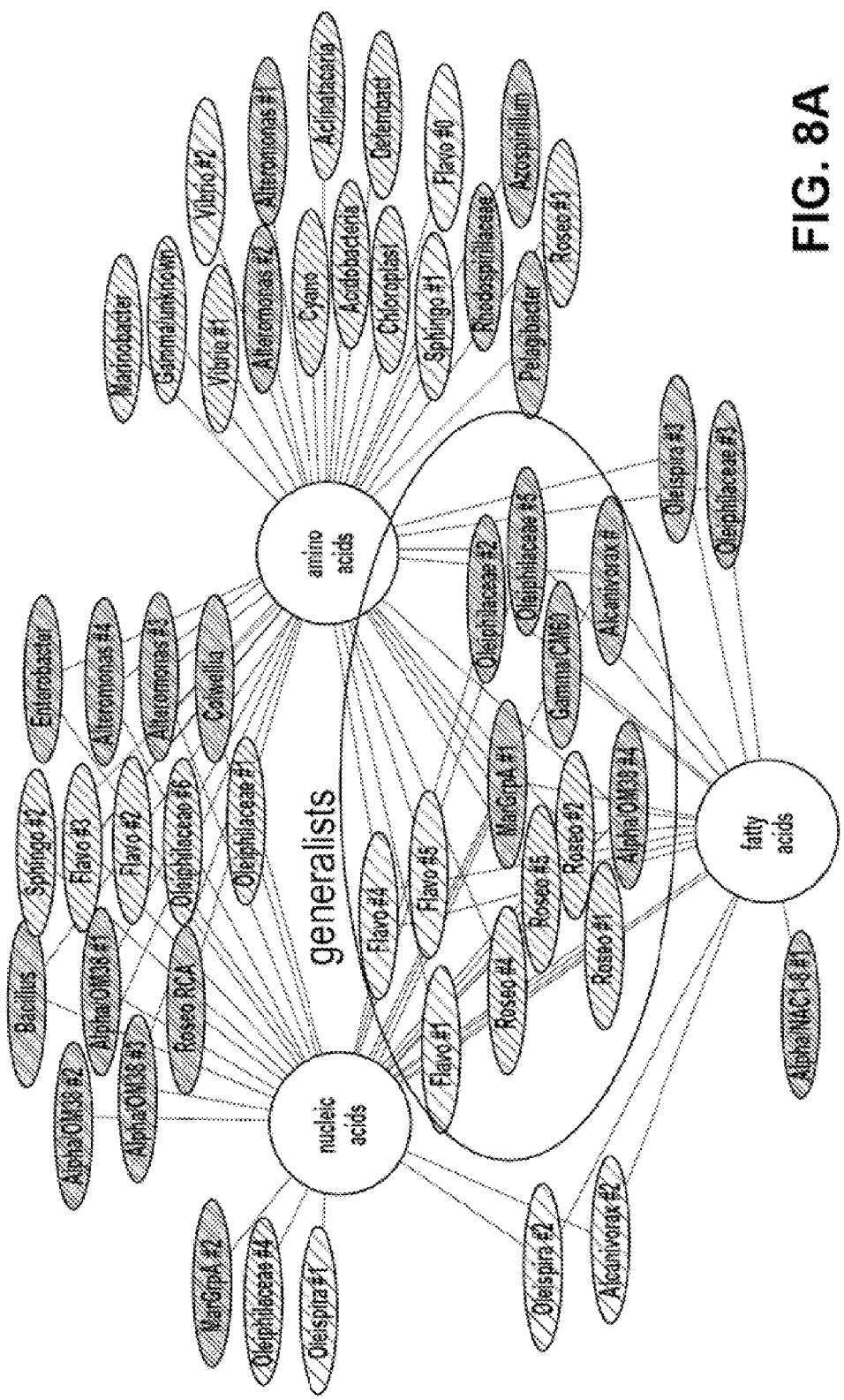
FIG. 8A shows a network map of Chip-SIP analysis of the uptake patterns of three organic substrates by different bacterial taxa in an estuary, identifying substrate specialists and generalists; the thicknesses of the lines are proportional to the substrate incorporation rates based on HCE calculations (Flavo=Flavobacteriaceae, Roseo=Roseobacter, MarGrpA=Marine Group A).

We detected isotopic enrichment of at least one of the three added substrates in 52 out of the 81 taxa with positive RNA hybridization (FIGS. 10-13). A network diagram, based on the measured HCE values, illustrates the movement of organic matter between substrates and microbial taxa, and clearly indicates generalists that incorporated all three substrates versus specialist consumers of only one substrate (FIG. 8A). Our analysis reveals that generalists and specialists were not necessarily distinguishable based on 16S phylogeny. In other words, members of a bacterial family could be generalists while others specialists. Such an analysis, which includes quantitative information (visualized by the thickness of the lines connecting substrates to taxa), is a substantial step forward in our understanding of organic matter flow in the microbial loop.

To compare genome-predicted potential biogeochemical activity to our measured substrate incorporation data, we examined the presence of genes involved in the extracellular degradation or transport of these substrates in the sequenced genomes of marine bacterial isolates (Table 2). Table 2 is shown below:

TABLE S2 presence of identified amino acid transporters, extracellular nucleases, and nucleoside and fatty acid transport in 110 genomes of marine bacterial isolates. Word searches performed with Joint Genome Institute's Integrated Microbial Genomes (IMG) online at IMG JGI website.

| Genome | Amino acid transport | Extracellular nuclease | Nucleoside transport | Fatty acid transport |
|---|---|---|---|---|
| *Agreia* sp. PHSC20C1 | Y | N | N | N |
| *Algoriphagus* sp. PR1 | Y | N | Y | Y |
| *Aurantimonas* sp. SI85-9A1 | Y | N | N | N |

TABLE S2-continued presence of identified amino acid transporters, extracellular nucleases, and nucleoside and fatty acid transport in 110 genomes of marine bacterial isolates. Word searches performed with Joint Genome Institute's Integrated Microbial Genomes (IMG) online at IMG JGI website.

| Genome | Amino acid transport | Extracellular nuclease | Nucleoside transport | Fatty acid transport |
|---|---|---|---|---|
| *Bacillus* sp. B14905 | Y | N | Y | N |
| *Bacillus* sp. NRRL B-14911 | Y | N | Y | N |
| *Bacillus* sp. SG-1 | Y | Y | Y | N |
| *Beggiatoa* sp. PS | Y | N | N | Y |
| *Bermanella marisrubri* | Y | N | N | Y |
| *Blastopirellula marina* DSM 3645 | Y | Y | N | N |
| *Caminibacter mediatlanticus* TB-2 | Y | N | N | N |
| *Candidatus Blochmannia pennsylvanicus* BPEN | Y | N | N | N |
| *Candidatus Pelagibacter ubique* HTCC1002 | Y | N | N | N |
| *Carnobacterium* sp. AT7 | Y | N | Y | Y |
| *Congregibacter litoralis* KT71 | Y | N | Y | N |
| *Croceibacter atlanticus* HTCC2559 | Y | Y | Y | N |
| *Cyanothece* sp. CCY 0110 | Y | N | Y | N |
| *Dokdonia donghaensis* MED134 | Y | Y | Y | N |
| *Erythrobacter litoralis* HTCC2594 | Y | N | Y | Y |
| *Erythrobacter* sp. NAP1 | Y | N | N | N |
| *Erythrobacter* sp. SD-21 | Y | N | Y | N |
| *Finegoldia magna* ATCC 29328 | Y | N | N | N |
| *Flavobacteria bacterium* BAL38 | Y | N | N | Y |
| *Flavobacteria bacterium* BBFL7 | N | Y | N | N |
| *Flavobacteriales bacterium* ALC-1 | Y | N | Y | N |
| *Flavobacteriales bacterium* HTCC2170 | Y | N | Y | N |
| *Fulvimarina pelagi* HTCC2506 | Y | N | N | Y |
| *Hoeflea phototrophica* DFL-43 | Y | N | N | Y |
| *Hydrogenivirga* sp. 128-5-R1-1 | Y | N | N | N |
| *Idiomarina baltica* OS145 | Y | Y | N | Y |
| *Janibacter* sp. HTCC2649 | Y | Y | N | N |
| *Kordia algicida* OT-1 | Y | Y | N | Y |
| *Labrenzia aggregata* IAM 12614 | Y | N | N | N |
| *Leeuwenhoekiella blandensis* MED217 | Y | N | Y | N |
| *Lentisphaera araneosa* HTCC2155 | Y | N | N | Y |
| *Limnobacter* sp. MED105 | Y | N | N | Y |
| *Loktanella vestfoldensis* SKA53 | Y | N | N | N |
| *Lyngbya* sp. PCC 8106 | Y | Y | Y | N |
| marine gamma proteobacterium HTCC2080 | Y | Y | Y | Y |
| marine gamma proteobacterium HTCC2143 | Y | N | N | N |
| marine gamma proteobacterium HTCC2148 | Y | N | N | N |
| marine gamma proteobacterium HTCC2207 | Y | N | N | N |
| *Marinobacter algicola* DG893 | Y | Y | N | Y |
| *Marinobacter* sp. ELB17 | Y | N | N | Y |
| *Marinomonas* sp. MED121 | Y | Y | N | N |
| *Mariprofundus ferrooxydans* PV-1 | Y | N | N | Y |
| *Methylophilales bacterium* HTCC2181 | N | N | N | N |
| *Microscilla marina* ATCC 23134 | Y | Y | Y | N |
| *Moritella* sp. PE36 | Y | Y | Y | Y |
| *Neptuniibacter caesariensis* | Y | N | N | N |
| *Nisaea* sp. BAL199 | Y | N | N | Y |
| *Nitrobacter* sp. Nb-311A | Y | N | N | N |
| *Nitrococcus mobilis* Nb-231 | Y | N | N | N |
| *Nodularia spumigena* CCY9414 | Y | N | N | N |
| *Oceanibulbus indolifex* HEL-45 | Y | N | Y | Y |
| *Oceanicaulis alexandrii* HTCC2633 | Y | N | N | N |
| *Oceanicola batsensis* HTCC2597 | Y | Y | N | N |
| *Oceanicola granulosus* HTCC2516 | Y | Y | Y | N |
| *Parvularcula bermudensis* HTCC2503 | Y | Y | Y | N |
| *Pedobacter* sp. BAL39 | Y | N | N | Y |
| *Pelotomaculum thermopropionicum* SI | Y | N | N | N |
| *Phaeobacter gallaeciensis* 2.10 | Y | N | N | N |
| *Phaeobacter gallaeciensis* BS107 | Y | N | N | N |
| *Photobacterium angustum* S14 | Y | Y | Y | Y |
| *Photobacterium profundum* 3TCK | Y | Y | Y | Y |
| *Photobacterium* sp. SKA34 | Y | Y | Y | Y |
| *Planctomyces maris* DSM 8797 | Y | Y | N | N |
| *Plesiocystis pacifica* SIR-1 | Y | N | Y | Y |
| *Polaribacter irgensii* 23-P | Y | Y | Y | N |
| *Polaribacter* sp. MED152 | Y | Y | Y | N |
| *Prochlorococcus marinus* AS9601 | N | N | N | N |

TABLE S2-continued presence of identified amino acid transporters, extracellular nucleases, and nucleoside and fatty acid transport in 110 genomes of marine bacterial isolates. Word searches performed with Joint Genome Institute's Integrated Microbial Genomes (IMG) online at IMG JGI website.

| Genome | Amino acid transport | Extracellular nuclease | Nucleoside transport | Fatty acid transport |
|---|---|---|---|---|
| *Prochlorococcus marinus* MIT 9211 | Y | N | N | N |
| *Prochlorococcus marinus* MIT 9301 | N | N | N | N |
| *Prochlorococcus marinus* MIT 9303 | Y | N | N | N |
| *Prochlorococcus marinus* MIT 9515 | Y | N | N | N |
| *Prochlorococcus marinus* NATL1A | Y | N | N | N |
| *Pseudoalteromonas* sp. TW-7 | Y | N | Y | Y |
| *Pseudoalteromonas tunicata* D2 | Y | N | Y | Y |
| *Psychroflexus torquis* ATCC 700755 | Y | Y | N | N |
| *Psychromonas* sp. CNPT3 | Y | N | N | Y |
| *Reinekea* sp. MED297 | Y | Y | N | N |
| *Rhodobacterales bacterium* HTCC2150 | Y | Y | Y | N |
| *Rhodobacterales bacterium* HTCC2654 | Y | N | N | N |
| *Rhodobacterales* sp. HTCC2255 | Y | N | Y | N |
| *Roseobacter litoralis* Och 149 | Y | N | N | N |
| *Roseobacter* sp. AzwK-3b | Y | N | N | N |
| *Roseobacter* sp. CCS2 | Y | Y | N | N |
| *Roseobacter* sp. MED193 | Y | N | N | N |
| *Roseobacter* sp. SK209-2-6 | Y | N | Y | N |
| *Roseovarius nubinhibens* ISM | Y | N | N | N |
| *Roseovarius* sp. 217 | Y | Y | Y | Y |
| *Roseovarius* sp. HTCC2601 | Y | N | Y | N |
| *Roseovarius* sp. TM1035 | Y | N | N | N |
| *Sagittula stellata* E-37 | Y | Y | N | N |
| *Shewanella benthica* KT99 | Y | Y | N | Y |
| *Sphingomonas* sp. SKA58 | Y | N | Y | Y |
| *Sulfitobacter* sp. EE-36 | Y | N | N | N |
| *Sulfitobacter* sp. NAS-14.1 | Y | N | N | N |
| *Synechococcus* sp. BL107 | Y | N | N | N |
| *Synechococcus* sp. RS9916 | Y | N | N | N |
| *Synechococcus* sp. RS9917 | Y | N | N | N |
| *Synechococcus* sp. WH 5701 | Y | N | N | N |
| *Synechococcus* sp. WH 7805 | Y | N | N | N |
| *Ulvibacter* sp. SCB49 | Y | Y | N | Y |
| *Vibrio alginolyticus* 12G01 | Y | Y | Y | Y |
| *Vibrio campbellii* AND4 | Y | N | Y | Y |
| *Vibrio harveyi* HY01 | Y | N | Y | Y |
| *Vibrio shilonii* AK1 | Y | Y | Y | Y |
| *Vibrio* sp. MED222 | Y | Y | Y | Y |
| *Vibrio splendidus* 12B01 | Y | Y | Y | Y |
| *Vibrionales bacterium* SWAT-3 | Y | Y | Y | Y |

Incorporation of leucine and other amino acids is routinely used as a proxy for bacterial production in aquatic systems (22) and metatranscriptomic evidence suggests most marine bacterial taxa incorporate amino acids directly (23). As nearly all genomes of marine bacteria (106/110) possess annotated putative amino acid transporters, we expected most of the active microbes in the SF Bay system would incorporate amino acids. Bacterial uptake of single nucleosides (e.g. thymidine) is ubiquitous and used to measure rates of growth (24), but only a few studies have examined longer nucleic acid molecules as a source of carbon or nitrogen for microbial metabolism (see ref. 25 as a recent example). Considering that half (55/110) of fully sequenced marine bacterial genomes contain at least one identified nucleoside transporter or extracellular nuclease, we expected nucleic acid incorporation could be a common phenomenon in the environment. Finally, we also chose to examine fatty acid incorporation because marine bacterial isolates commonly reveal high lipase activity (26), although only 38/110 sequenced bacterial genomes contained identified lipid transporters. In addition, comparative genomics has shown that oligotrophic marine bacterial genomes contain significantly more genes for lipid metabolism and fatty acid degradation than copiotrophic genomes (27). If oligotrophs favor fatty acid incorporation, we hypothesized that it would be less common than amino acid incorporation in our samples since a eutrophic estuary should favor copiotrophs.

In general terms, our results agree with predictions made from available marine genomic data: amino acids were the most commonly incorporated (46 taxa), followed by nucleic acids (32 taxa) and then fatty acids (18 taxa). However, the chip-SIP and genomic data did not always concur. For example, all the *Vibrio* genomes we examined contain putative enzymes for the utilization of the three substrates tested (Table 2), yet chip-SIP indicates the *Vibrio* taxa we detected incorporated only amino acids (FIG. 8A). In this case, genomic potential did not indicate activity. With a relatively high level of taxonomic detail, chip-SIP showed that over 10% of the active taxa in this sample (6 out of 52) did not incorporate amino acid-derived $^{15}N$ into their RNA, even though amino acids are considered a ubiquitous substrate for marine bacteria (22, 23). Indeed, if rates of marine bacterial carbon production based on leucine incorporation are underestimates, this could have significant implications for global carbon modeling efforts. Our analyses also revealed that bacteria commonly incorporate carbon (and presumably nitrogen) from external nucleic acid sources. This complements previous work that identified nucleic acids as a source of phosphorus for marine bacteria, (28). Nucleic acids have C/N ratios lower than phytoplankton-derived organic matter and most amino acids (average C/N of RNA=2.5, POM=6.6, amino acids=3.6). This makes them an ideal resource for bacteria that have relatively high nitrogen requirements. Fatty acids, which contain no nitrogen, were less commonly incorporated than either amino acids or nucleic acids, although we did identify one taxon (uncultivated Alphaproteobacterial clade NAC1-6) that incorporated this substrate but not the others. Such measurements of taxon-specific substrate incorporation within complex communities, along with data gleaned from genomic sequencing, could clearly be useful during the selection of strategies for isolation of previously uncultured microbial taxa.

A frequently accepted, although increasingly controversial view in microbial ecology (29), maintains that 16S phylogeny is closely related to functional role. It is widely assumed that taxa that are closely related by 16S phylogeny are more likely to be functionally similar than to taxa more phylogenetically distant. This concept has been a major assumption of microbial ecology research, without which 16S diversity surveys lose their functional context. Chip-SIP allowed us to test this assumption by matching functional in situ resource use to 16S phylogenetic relationships.

Figure 8B:
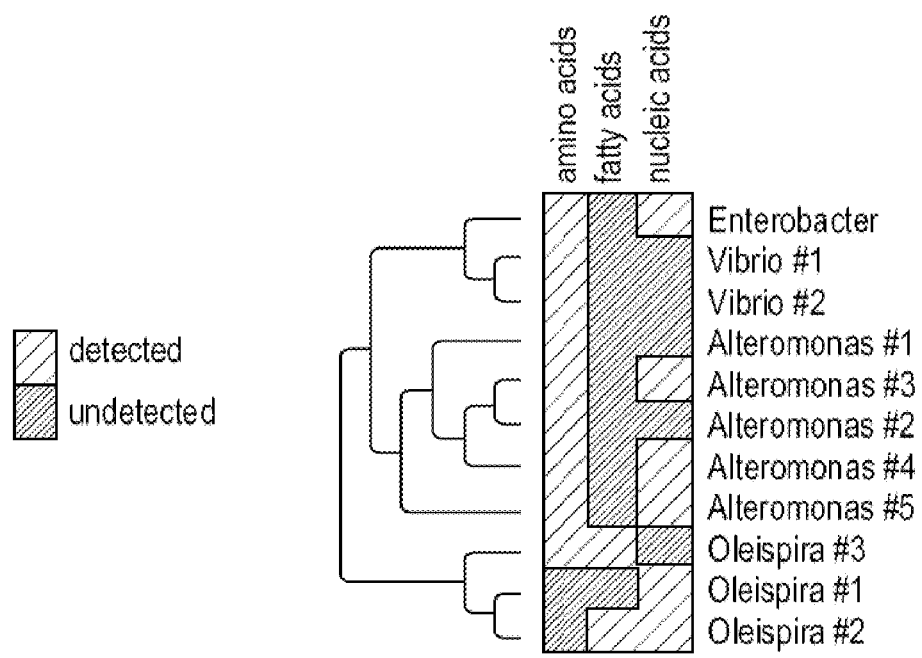
FIG. 8B shows a heat map relationship between substrate incorporation (green=detected, black=not detected) and 16S rRNA phylogeny for a subset of the Gammaproteobacteria, indicating taxa where physiological traits match phylogeny (Alteromonadales and Vibrionaceae) and where they do not (*Oleispira*).

As an example, we mapped substrate utilization data across a subset of the Gammaproteobacterial phylogeny (FIG. 8B) and observed taxon specific responses. For the well characterized and previously cultivated copiotrophic organisms of the genera *Vibrio* and *Alteromonas*, patterns of resource use matched 16S phylogeny quite well: all taxa incorporated amino acids, and several *Alteromonas* taxa incorporated nucleic acids, while no taxon incorporated fatty acids (FIG. 8B). In this case, 16S based phylogeny correlates with resource use. However, in other phylogenetic groups there is a clear decoupling between phylogeny and biogeochemical function. The three taxa identified from the *Oleispira* group exhibited completely different substrate incorporation patterns (FIG. 8B): one incorporated amino acids and fatty acids, the second incorporated only nucleic acids, while the third incorporated both fatty acids and nucleic acids. Based on these data, it would be impossible to predict the resource use of a different *Oleispira* taxon. This decoupling between phylogenetic similarity and measured substrate incorporation illustrates the limitation of using 16S phylogenetic information to predict functional resource utilization.

Based on the success of these initial experiments, chip-SIP may facilitate great strides in our understanding of the functional mechanisms that underlie patterns of microbial diversity. Using this high resolution, high-sensitivity approach, we have revealed patterns of resource utilization in an estuarine community with critical implications for our understanding of carbon cycling in marine environments. These data considerably expand upon previous studies that have identified marine bacterial resource partitioning based on seasonal and small-scale spatial habitat use (30) by adding relative rates of substrate utilization as a critical component of the bacterial niche.

REFERENCES

1. P. Falkowski et al., The global carbon cycle: a test of our knowledge of earth as a system. *Science* 290, 291 (2000).
2. S. J. Giovannoni, U. Stingl, Molecular diversity and ecology of microbial plankton. *Nature* 437, 343 (2005).
3. M. S. Rappé, P. F. Kemp, S. J. Giovannoni, Phylogenetic diversity of marine coastal picoplankton 16S rRNA genes cloned from the continental shelf off Cape Hatteras, N.C. *Limnol. Oceanogr.* 42, 811 (1997).
4. E. F. DeLong et al., Community genomics among stratified microbial assemblages in the ocean's Interior. *Science* 311, 496 (2006).
5. S. Radajewski, P. Ineson, N. R. Parekh, J. C. Murrell, Stable-isotope probing as a tool in microbial ecology. *Nature* 403, 646 (2000).
6. M. Manefield, A. S. Whiteley, R. I. Griffiths, M. J. Bailey, RNA stable isotope probing, a novel means of linking microbial community function to phylogeny. *Appl. Environ. Microbiol.* 68, 5367 (2002).
7. J. Neufeld, M. Wagner, J. Murrell, Who eats what, where and when? Isotope-labelling experiments are coming of age. *ISME J.* 1, 103 (2007).
8. J. C. Murrell, A. S. Whiteley, *Stable isotope probing and related technologies.* (ASM Press, Washington D.C., 2010).
9. M. G. Dumont, J. C. Murrell, Stable isotope probing: linking microbial identity to function. *Nat. Rev. Microbiol.* 3, 499 (2005).
10. O. Uhlik, K. Jecná, M. B. Leigh, M. Macková, T. Macek, DNA-based stable isotope probing: a link between community structure and function. *Sci. Total Environ.* 407, 3611 (2009).
11. S. L. Addison, I. R. McDonald, G. Lloyd-Jones, Stable isotope probing: technical considerations when resolving $^{15}$N-labeled RNA in gradients. *J. Microbiol. Methods* 80, 70 (2010).
12. H. T. S. Boschker et al., Direct linking of microbial populations to specific biogeochemical processes by $^{13}$C-labelling of biomarkers. *Nature* 392, 801 (1998).
13. S. Behrens et al., Linking microbial phylogeny to metabolic activity at the single-cell level by using enhanced element labeling-catalyzed reporter deposition fluorescence in situ hybridization (EL-FISH) and NanoSIMS. *Appl. Environ. Microbiol.* 74, 3143 (2008).
14. C. C. Ouverney, J. A. Fuhrman, Combined microautoradiography-16S rRNA probe technique for determination of radioisotope uptake by specific microbial cell types in situ. *Appl. Environ. Microbiol.* 65, 1746 (1999).
15. J. Adamczyk et al., The isotope array, a new tool that employs substrate-mediated labeling of rRNA for determination of microbial community structure and function. *Appl. Environ. Microbiol.* 69, 6875 (2003).
16. E. L. Brodie et al., Application of a high-density oligonucleotide microarray approach to study bacterial population dynamics during uranium reduction and reoxidation. *Appl. Environ. Microbiol.* 72, 6288 (2006).
17. C. Suttle, J. A. Fuhrman, D. G. Capone, Rapid ammonium cycling and concentration-dependent partitioning of ammonium and phosphate: implications for carbon transfer in planktonic communities. *Limnol. Oceanogr.* 35, 424 (1990).
18. M. S. Rappe, S. A. Connon, K. L. Vergin, S. J. Giovannoni, Cultivation of the ubiquitous SAR11 marine bacterioplankton clade. *Nature* 418, 630 (2002).
19. J. C. Goldman, M. R. Dennett, Ammonium regeneration and carbon utilization by marine bacteria grown on mixed substrates. *Mar. Biol.* 109, 369 (1991).
20. L. R. Pomeroy, P. J. l. Williams, F. Azam, J. E. Hobbie, The microbial loop. *Oceanogr.* 20, (2007).
21. M. J. Fernandez-Reiriz et al., Biomass production and variation in the biochemical profile (total protein, carbohydrates, RNA, lipids and fatty acids) of seven species of marine microalgae. *Aquacult.* 83, 17 (1989).

22. D. Kirchman, E. K'nees, R. Hodson, Leucine incorporation and its potential as a measure of protein synthesis by bacteria in natural aquatic systems. *Appl. Environ. Microbiol.* 49, 599 (1985).
23. R. S. Poretsky, S. Sun, X. Mou, M. A. Moran, Transporter genes expressed by coastal bacterioplankton in response to dissolved organic carbon. *Envir. Microbiol.* 12, 616 (2010).
24. J. A. Fuhrman, F. Azam, Bacterioplankton secondary production estimates for coastal waters of British Columbia, Canada, Antarctica, and California, USA. *Appl. Environ. Microbiol.* 39, 1085 (1980).
25. J. T. Lennon, Diversity and metabolism of marine bacteria cultivated on dissolved DNA. *Appl. Environ. Microbiol.* 73, 2799 (2007).
26. J. Martinez, D. C. Smith, G. F. Steward, F. Azam, Variability in ectohydrolytic enzyme activities of pelagic marine bacteria and its significance for substrate processing in the sea. *Aquat. Microb. Ecol.* 10, 223 (1996).
27. F. M. Lauro et al., The genomic basis of trophic strategy in marine bacteria. *Proc. Natl. Acad. Sci. U.S.A* 106, 15527 (2009).
28. J. W. Ammerman, F. Azam, Bacterial 5-nucleotidase in aquatic ecosystems: a novel mechanism of phosphorus regeneration. *Science* 227, 1338 (1985).
29. W. F. Doolittle, O. Zhaxybayeva, On the origin of prokaryotic species. *Genome Res.* 19, 744 (2009).
30. D. E. Hunt et al., Resource partitioning and sympatric differentiation among closely related bacterioplankton. *Science* 320, 1081 (2008).

REFERENCES FOR EXAMPLE 2

1. R. C. Dugdale, F. P. Wilkerson, V. E. Hogue, A. Marchi, The role of ammonium and nitrate in spring bloom development in San Francisco Bay. *Estuar. Coast. Shelf Sci.* 73, 17 (2007).
2. R. B. Hanson, J. Snyder, Glucose exchanges in a salt marsh estuary: biological activity and chemical measurements. *Limnol. Oceanogr.* 25, 633 (1980).
3. R. Evens, J. Braven, A seasonal comparison of the dissolved free amino acid levels in estuarine and English Channel waters. *Sci. Total Environ.* 76, 69 (1988).
4. T. B. Stauffer, W. G. Macintyre, Dissolved fatty acids in the James River estuary, Virginia, and adjacent ocean waters. *Chesap. Sci.* 11, 216 (1970).
5. M. F. DeFlaun, J. H. Paul, W. H. Jeffrey, Distribution and molecular weight of dissolved DNA in subtropical estuarine and oceanic environments. *Mar. Ecol. Prog. Ser.* 38, 65 (1987).
6. E. L. Brodie et al., Application of a high-density oligonucleotide microarray approach to study bacterial population dynamics during uranium reduction and reoxidation. *Appl. Environ. Microbiol.* 72, 6288 (2006).
7. T. Z. DeSantis et al., Greengenes, a Chimera-Checked 16S rRNA Gene Database and Workbench Compatible with ARB. *Appl. Environ. Microbiol.* 72, 5069 (2006).
8. W. Ludwig et al., ARB: a software environment for sequence data. *Nucl. Acids Res.* 32, 1363 (2004).
9. S. Singh-Gasson et al., Maskless fabrication of light-directed oligonucleotide microarrays using a digital micromirror array. *Nat. Biotech.* 17, 974 (1999).
10. M. S. Cline et al., Integration of biological networks and gene expression data using Cytoscape. *Nat. Protocols* 2, 2366 (2007).

The above examples are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

TABLE 1 list of probes specific for laboratory bacterial strains and San Francisco Bay natural community

| SEQUENCE_ID | PROBE_SEQUENCE | SEQUENCE_ID | PROBE_SEQUENCE | SEQUENCE_ID | PROBE SEQUENCE |
|---|---|---|---|---|---|
| Pstutzeri_1 | TAACCGTCCCCCCGAAGGTTAGACT | Vcholerae_1 | AACTTAACCACCTTCCTCCCTACTG | Bcereus_1 | TCCACCTCGCGGTCTTGCAGCTCTT |
| Pstutzeri_2 | GGTAACCGTCCCCCCGAAGGTTAGA | Vcholerae_2 | GTAGGTAACGTCAAATGATTAAGGT | Bcereus_2 | GCCTTTCAATTTCGAACCATGCGGT |
| Pstutzeri_3 | TGGTAACCGTCCCCCCGAAGGTTAG | Vcholerae_3 | TGTAGGTAACGTCAAATGATTAAGG | Bcereus_3 | CTCTTAATCCATTCGCTCGACTTGC |
| Pstutzeri_4 | GTAACCGTCCCCCCGAAGGTTAGAC | Vcholerae_4 | TAACTTAACCACCTTCCTCCCTACT | Bcereus_4 | CCACCTCGCGGTCTTGCAGCTCTTT |
| Pstutzeri_5 | ACTCCGTGGTAACCGTCCCCCCGAA | Vcholerae_5 | ACTTAACCACCTTCCTCCCTACTGA | Bcereus_5 | CTCTGCTCCCGAAGGAGAAGCCCTA |
| Pstutzeri_6 | CACTCCGTGGTAACCGTCCCCCCGA | Vcholerae_6 | TTAACTTAACCACCTTCCTCCCTAC | Bcereus_6 | CCGCCTTTCAATTTCGAACCATGCG |
| Pstutzeri_7 | TCACTCCGTGGTAACCGTCCCCCCG | Vcholerae_7 | TAAGGTATTAACTTAACCACCTTCC | Bcereus_7 | TCTGCTCCCGAAGGAGAAGCCCTAT |
| Pstutzeri_8 | ACCGTCCCCCCGAAGGTTAGACTAG | Vcholerae_8 | CTGTAGGTAACGTCAAATGATTAAG | Bcereus_8 | ACCTGTCACTCTGCTCCCGAAGGAG |
| Pstutzeri_9 | ATCACTCCGTGGTAACCGTCCCCCC | Vcholerae_9 | CTTAACCACCTTCCTCCCTACTGAA | Bcereus_9 | GCTCTTAATCCATTCGCTCGACTTG |
| Pstutzeri_10 | CCGTGGTAACCGTCCCCCCGAAGGT | Vcholerae_10 | ATTAACTTAACCACCTTCCTCCCTA | Bcereus_10 | CGCCTTTCAATTTCGAACCATGCGG |
| Pstutzeri_11 | CTCCGTGGTAACCGTCCCCCCGAAG | Vcholerae_11 | AAGGTATTAACTTAACCACCTTCCT | Bcereus_11 | ACTCTGCTCCCGAAGGAGAAGCCCT |
| Pstutzeri_12 | CCGTCCCCCCGAAGGTTAGACTAGC | Vcholerae_12 | TTAACCACCTTCCTCCCTACTGAAA | Bcereus_12 | GCTCCCGAAGGAGAAGCCCTATCTC |
| Pstutzeri_13 | CCACCACCCTCTGCCATACTCTAGC | Vcholerae_13 | CTTCTGTAGGTAACGTCAAATGATT | Bcereus_13 | TCACTCTGCTCCCGAAGGAGAAGCC |
| Pstutzeri_14 | TCCACCACCCTCTGCCATACTCTAG | Vcholerae_14 | TATTAACTTAACCACCTTCCTCCCT | Bcereus_14 | TCTTAATCCATTCGCTCGACTTGCA |
| Pstutzeri_15 | TTCCACCACCCTCTGCCATACTCTA | Vcholerae_15 | ACGACGTACTTTGTGAGATTCGCTC | Bcereus_15 | CTGCTCCCGAAGGAGAAGCCCTATC |
| Pstutzeri_16 | AATTCCACCACCCTCTGCCATACTC | Vcholerae_16 | TACGACGTACTTTGTGAGATTCGCT | Bcereus_16 | TAATCCATTCGCTCGACTTGCATGT |
| Pstutzeri_17 | AAATTCCACCACCCTCTGCCATACT | Vcholerae_17 | ACTACGACGTACTTTGTGAGATTCG | Bcereus_17 | CACTCTGCTCCCGAAGGAGAAGCCC |
| Pstutzeri_18 | GAAATTCCACCACCCTCTGCCATAC | Vcholerae_18 | CTACGACGTACTTTGTGAGATTCGC | Bcereus_18 | GGTCTTGCAGCTCTTTGTACCGTCC |
| Pstutzeri_19 | ATTCCACCACCCTCTGCCATACTCT | Vcholerae_19 | GACTACGACGTACTTTGTGAGATTC | Bcereus_19 | TGCTCCCGAAGGAGAAGCCCTATCT |
| Pstutzeri_20 | GGAAATTCCACCACCCTCTGCCATA | Vcholerae_20 | AGGTATTAACTTAACCACCTTCCTC | Bcereus_20 | CTTAATCCATTCGCTCGACTTGCAT |
| Pstutzeri_21 | CAGGAAATTCCACCACCCTCTGCCA | Vcholerae_21 | GGTATTAACTTAACCACCTTCCTCC | Bcereus_21 | TTAATCCATTCGCTCGACTTGCATG |
| Pstutzeri_22 | AGGAAATTCCACCACCCTCTGCCAT | Vcholerae_22 | GTATTAACTTAACCACCTTCCTCCC | Bcereus_22 | CTCCCGAAGGAGAAGCCCTATCTCT |
| Pstutzeri_23 | CAGTGTCAGTATTAGCCCAGGTGGT | Vcholerae_23 | CGCGGTATCGCTGCCCTCTGTATAC | Bcereus_23 | GTCACTCTGCTCCCGAAGGAGAAGC |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| Pstutzeri_24 | TCAGTATTAGCCCAGGTGGTCGCCT | Vcholerae_24 | TCGCGGTATCGCTGCCCTCTGTATA | Bcereus_24 | CACCTCGCGGTCTTGCAGCTCTTTG |
| Pstutzeri_25 | TCAGTGTCAGTATTAGCCCAGGTGG | Vcholerae_25 | CTTGTCAGTTTCAAATGCGATTCCT | Bcereus_25 | GTCTTGCAGCTCTTTGTACCGTCCA |
| Pstutzeri_26 | TGTCAGTATTAGCCCAGGTGGTCGC | Vcholerae_26 | TTGTCAGTTTCAAATGCGATTCCTA | Bcereus_26 | TGTCACTCTGCTCTGCTCCGAAGAGAAG |
| Pstutzeri_27 | GTCAGTATTAGCCCAGGTGGTCGCC | Vcholerae_27 | GCGGTATCGCTGCCCTCTGTATACG | Bcereus_27 | TCCCGAAGGAGAAGCCCTATCTCTA |
| Pstutzeri_28 | CCTCAGTGTCAGTATTAGCCCAGGT | Vcholerae_28 | CCTGGGCATATCCGGTAGCGCAAGG | Bcereus_28 | CGGTCTTGCAGCTCTTTGTACCGTC |
| Pstutzeri_29 | CTCAGTGTCAGTATTAGCCCAGGTG | Vcholerae_29 | TCCCACCTGGGCATATCCGGTAGCG | Bcereus_29 | TCAAAATGTTATCCGGTATTAGCCC |
| Pstutzeri_30 | ACCTCAGTGTCAGTATTAGCCCAGG | Vcholerae_30 | GGCATATCCGGTAGCGCAAGGCCCG | Bcereus_30 | CCTGTCACTCTGCTCCCGAAGGAGA |
| Pstutzeri_31 | GTGTCAGTATTAGCCCAGGTGGTCG | Vcholerae_31 | ACCTGGGCATATCCGGTAGCGCAAG | Bcereus_31 | TTCAAAATGTTATCCGGTATTAGCC |
| Pstutzeri_32 | AGTGTCAGTATTAGCCCAGGTGGTC | Vcholerae_32 | CTGGGCATATCCGGTAGCGCAAGGC | Bcereus_32 | CACCTGTCACTCTGCTCCCGAAGGA |
| Pstutzeri_33 | CACCTCAGTGTCAGTATTAGCCCAG | Vcholerae_33 | CCCACCTGGGCATATCCGGTAGCGC | Bcereus_33 | TCTTGCAGCTCTTTGTACCGTCCAT |
| Pstutzeri_34 | GCACCTCAGTGTCAGTATTAGCCCA | Vcholerae_34 | TGGGCATATCCGGTAGCGCAAGCC | Bcereus_34 | CTGTCACTCTGCTCCCGAAGGAGAA |
| Pstutzeri_35 | CGCACCTCAGTGTCAGTATTAGCCC | Vcholerae_35 | GGGCATATCCGGTAGCGCAAGGCCC | Bcereus_35 | GCGGTCTTGCAGCTCTTTGTACCGT |
| Pstutzeri_36 | TTCCGCACCTCAGTGTCAGTATTAGC | Vcholerae_36 | GCATATCCGGTAGCGCAAGGCCCGA | Bcereus_36 | CGCGGTCTTGCAGCTCTTTGTACCG |
| Pstutzeri_37 | TCGCACCTCAGTGTCAGTATTAGCC | Vcholerae_37 | CCACCTGGGCATATCCGGTAGCGCA | Bcereus_37 | AGCTCTTAATCATTCGCAGCTCGACTT |
| Pstutzeri_38 | AATGCGTTAGCTGCGCCACTAAGAT | Vcholerae_38 | CATATCCGGTAGCGCAAGGCCCGAA | Bcereus_38 | ACCTGCGGTCTTGCAGCTCTTTGT |
| Pstutzeri_39 | CACACCCCTCTGCCATATCCTAGCT | Vcholerae_39 | CACCTGGGCATATCCGGTAGCGCAA | Bcereus_39 | TCGCGGTCTTGCAGCTCTTTGTACC |
| Pstutzeri_40 | ACACAGGAAATTCACCACACCCTCTG | Vcholerae_40 | ATATCCGGTAGCGCAAGGCCCGAAG | Bcereus_40 | CTCGCGGTCTTGCAGCTCTTTGTAC |
| Pstutzeri_41 | CACAGGAAATTCACCACACCCTCTGC | Vcholerae_41 | TATCCGGTAGCGCAAGGCCCGAAGG | Bcereus_41 | TGCACACCTGTCACTCTGCTCCCG |
| Pstutzeri_42 | ACAGGAAATTCCACCACACCCCTCTGCC | Vcholerae_42 | TCCCCTGCTTTGCTCTTTGCGAGGTT | Bcereus_42 | ATGCACCACCTGTCACTCTGCTCCC |
| Pstutzeri_43 | GAAGTTAGCGCGGTGCTTATTCTGTC | Vcholerae_43 | GTCCCCTGCTTTGCTCTTTGCGAGGT | Bcereus_43 | ACCACCTGTCACTCTGCTCCCCGAAG |
| Pstutzeri_44 | GAAAGTTCTCTGCATGTCAAGGCCT | Vcholerae_44 | CCGAAGGTCCCCTGCTTTGCTCTTTG | Bcereus_44 | GCACCACCTGTCACTCTGCTCCCGA |
| Pstutzeri_45 | AAAGTTCTCTGCATGTCAAGGCCTG | Vcholerae_45 | GGTCCCCTGCTTTGCTCTTTGCGAGG | Bcereus_45 | CACCACCTGTCACTCTGCTCCCGAA |
| Pstutzeri_46 | TCTCTGCATGTCAAGGCCTGGTAAG | Vcholerae_46 | GAAGGTCCCCTGCTTTGCTCTTTGCG | Bcereus_46 | CATAAGAGCAAGCTCTTAATCCATT |
| Pstutzeri_47 | GTTCTCTGCATGTCAAGGCCTGGTA | Vcholerae_47 | AGTCCCCTGCTTTGCTCTTTGCGAG | Bcereus_47 | CCTCGCGGTCTTGCAGCTCTTTGTA |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE SEQUENCE |
|---|---|---|---|---|---|
| Pstutzeri_48 | AGTTCTCTGCATGTCAAGGCCTGGT | Vcholerae_48 | CGAAGGTCCCCTGCTTTGCTCTTGC | Bcereus_48 | CCACCTGTCACTCTGCTCCCGAAGG |
| Pstutzeri_49 | AAGTTCTCTGCATGTCAAGGCCTGG | Vcholerae_49 | AAGGTCCCCTGCTTTGCTCTTGCGA | Bcereus_49 | AAGAGCAAGCTCTTAATCATTCGC |
| Pstutzeri_50 | CTCTGCATGTCAAGGCCTGGTAAGG | Vcholerae_50 | CCCCTGCTTTGCTCTTGCGAGGTTA | Bcereus_50 | CGAAGGAGAAGCCCTATCTCTAGGG |
| Pstutzeri_51 | TTCTCTGCATGTCAAGGCCTGGTAA | Vcholerae_51 | TCTAGGGCACAACCTCCAAGTAGAC | Bcereus_51 | AAGTCTTAATCATTCGCTCGACT |
| Pstutzeri_52 | CTGCATGTCAAGGCCTGGTAAGGTT | Vcholerae_52 | CTCTAGGGCACAACCTCCAAGTAGA | Bcereus_52 | TAAGAGCAAGCTCTTAATCATTCG |
| Pstutzeri_53 | TCTGCATGTCAAGGCCTGGTAAGGT | Vcholerae_53 | CCTCTAGGGCACAACCTCCAAGTAG | Bcereus_53 | ATAAGAGCAAGCTCTTAATCATTC |
| Pstutzeri_54 | TACTCACCCGTCCGCCGCTGAATCA | Vcholerae_54 | CGACGTACTTTGTGAGATTCGCTCC | Bcereus_54 | CCCGAAGGAGAAGCCCTATCTCTAG |
| Pstutzeri_55 | CAGCCATGCAGCACCTGTGTCAGAG | Vcholerae_55 | TCAGTTTCAAATGCGATTCCTAGTT | Bcereus_55 | CCGAAGGAGAAGCCCTATCTCTAGG |
| Pstutzeri_56 | ACAGCCATGCAGCACCTGTGTCAGA | Vcholerae_56 | AGTTTCAAATGCGATTCCTAGTTG | Bcereus_56 | CAAGCTCTTAATCATTCGCTCGAC |
| Pstutzeri_57 | GACAGCCATGCAGCACCTGTGTCAG | Vcholerae_57 | TGTCAGTTTCAAATGCGATTCCTAG | Bcereus_57 | AAGGAGAAGCCCTATCTCTAGGGTT |
| Pstutzeri_58 | CTGGAAAGTTCTCTGCATGTCAAGG | Vcholerae_58 | GTTTCAAATGCGATTCCTAGTTGA | Bcereus_58 | GAAGGAGAAGCCCTATCTCTAGGGT |
| Pstutzeri_59 | TGGAAAGTTCTCTGCATGTCAAGGC | Vcholerae_59 | CTAGCTTGTCAGTTTCAAATGCGAT | Bcereus_59 | GCAAGCTCTTAATCATTCGCTCGA |
| Pstutzeri_60 | GGAAAGTTCTCTGCATGTCAAGGCC | Vcholerae_60 | TCTAGCTTGTCAGTTTCAAATGCGA | Bcereus_60 | AGCAAGCTCTTAATCATTCGCTCG |
| eukaryotes_1 | AACTAAGAACGGCCATGCACCACCA | sphingo_1_1 | CCAGCTTGCTGCCCTCTGTACCATC | alpha_7_1 | ACATCTCTGTTTCCGCGACCGGGAT |
| eukaryotes_2 | CACCAACTAAGAACGGCCATGCACC | sphingo_1_2 | CAGCTTGCTGCCCTCTGTACCATCC | alpha_7_2 | CATCTCTGTTTCCGCGACCGGGATG |
| eukaryotes_3 | CCAACTAAGAACGGCCATGCACCAC | sphingo_1_3 | GCCAGCTTGCTGCCCTCTGTACCAT | alpha_7_3 | AAACATCTCTGTTTCCGCGACCGGG |
| eukaryotes_4 | ACCAACTAAGAACGGCCATGCACCA | sphingo_1_4 | TGCCAGCTTGCTGCCCTCTGTACCA | alpha_7_4 | GAAACATCTCTGTTTCCGCGACCGG |
| eukaryotes_5 | CCACCAACTAAGAACGGCCATGCAC | sphingo_1_5 | CAGTTTACGACCCAGAGGGGTGTCT | alpha_7_5 | AGAAACATCTCTGTTTCCGCGACCG |
| eukaryotes_6 | TCCACCAACTAAGAACGGCCATGCA | sphingo_1_6 | AGCAGTTTACGACCCAGAGGGCTGT | alpha_7_6 | AACATCTCTGTTTCCGCGACCGGGA |
| eukaryotes_7 | CAACTAAGAACGGCCATGCACCACC | sphingo_1_7 | AAGCAGTTTACGACCCAGAGGGCTG | alpha_7_7 | ATCTGTTTCCGCGACCGGGATGT |
| eukaryotes_8 | CTCCACCAACTAAGAACGGCCATGC | sphingo_1_8 | GCAGTTTACGACCCAGGCCATGTC | alpha_7_8 | CTGCCACTGTCCACCCGAGCAAGCT |
| eukaryotes_9 | TTGGAGCTGGAATTACCGCGGCTGC | sphingo_1_9 | CCGCTACCTCTAGTGTATTCAAGC | alpha_7_9 | CCACTGTCCACCCGAGCAAGCTCGG |
| eukaryotes_10 | TCAGGCTCCCCTCCGGAATCGAAC | sphingo_1_10 | CATTCCGCCTACCTCTAGTGTATTC | alpha_7_10 | GCCACTGTCCACCCGAGCAAGCTCG |
| eukaryotes_11 | TCTCAGGCTCCCCTCCGGAATCGA | sphingo_1_11 | TGCTGTTGCCAGCTTGCTGCCCTCT | alpha_7_11 | AAACCTCTAGTAGATACCACGCG |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| eukaryotes_12 | TATTGGAGCTGGAATTACCGCGGCT | sphingo_1_12 | GCTGTTGCCAGCTTGCTGCCCTCTG | alpha_7_12 | CCAAACCTCTAGGTAGATACCCACG |
| eukaryotes_13 | ATTGGAGCTGGAATTACCGCGGCTG | sphingo_1_13 | TTGCTGTTGCCAGCTTGCTGCCCTC | alpha_7_13 | GTCTGCCACTGTCCACCCGAGCAAG |
| eukaryotes_14 | TAAGAACGGCCATGCACCACCACCC | sphingo_1_14 | CACATTCCGCCTACCTCTAGTGTAT | alpha_7_14 | CCACCCGAGCAAGCTCGGGTTTCTC |
| eukaryotes_15 | CTAAGAACGGCCATGCACCACCACC | sphingo_1_15 | GTCACATTCCGCCTACCTCTAGTGT | alpha_7_15 | TGCCACTGTCCACCCGAGCAAGCTC |
| eukaryotes_16 | ACTAAGAACGGCCATGCACCACCAC | sphingo_1_16 | TCACATTCCGCCTACCTCTAGTGTA | alpha_7_16 | CAAACCTCTAGGTAGATACCCACGC |
| eukaryotes_17 | CTCAGGCTCCCTCTCCGGAATCGAA | sphingo_1_17 | GCTTTCGCTTAGCCGCTAACTGTGT | alpha_7_17 | TCTGCCACTGTCCACCCGAGCAAGC |
| eukaryotes_18 | CTATTGGAGCTGGAATTACCGCGGC | sphingo_1_18 | CGCTTTCGCTTAGCCGCTAACTGTG | alpha_7_18 | CGTCTGCCACTGTCCACCCGAGCAA |
| eukaryotes_19 | AAGAACGGCCATGCACCACCACCCA | sphingo_1_19 | TCGCTTAGCCGCTAACTGTGTATCG | alpha_7_19 | TCCGAACCTCTAGGTAGATTCCCAC |
| eukaryotes_20 | AGGGCTCCCTCTCCGGAATCGAACC | sphingo_1_20 | TTCGCTTAGCCGCTAACTGTGTATC | alpha_7_20 | CACCCGAGCAAGCTCGGGTTTCTCG |
| eukaryotes_21 | CAGGCTCCCTCTCCGGAATCGAACC | sphingo_1_21 | CTTTCGCTTAGCCGCTAACTGTGTA | alpha_7_21 | ACCCGAGCAAGCTCGGGTTTCTCGT |
| eukaryotes_22 | GCTATTGGAGCTGGAATTACCGCGG | sphingo_1_22 | CTGTTGCCAGCTTGCTGCCCTCTGT | alpha_7_22 | CCGTCTGCCACTGTCCACCCGAGCA |
| eukaryotes_23 | TTTCTCAGGCTCCCTCTCCGGAATC | sphingo1_23 | GTTGCCAGCTTGCTGCCCTCTGTAC | alpha_7_23 | CCGAACCTCTAGGTAGATTCCCACG |
| eukaryotes_24 | GGGCTCCCTCTCCGGAATCGAACCCT | sphingo_1_24 | TGTTGCCAGCTTGCTGCCCTCTGTA | alpha_7_24 | AACCTCTAGGTAGATACCCACGCGT |
| eukaryotes_25 | CACTCCACCAACTAAGAACGGCCAT | sphingo_1_25 | CGCTTAGCCGCTAACTGTGTATCGC | alpha_7_25 | TCCACCCGAGCAAGCTCGGGTTTCT |
| archaea_1 | TTGTGGTGCTTCCCCGCCAATTCCT | sphingo_2_1 | TACCGCTACACCCCTCGTTCCGCT | alpha_8_1 | CTGCCACTGTCCACCCGAGCAAGCT |
| archaea_2 | TGCTCCCCCGCCAATTCCTTTAAGT | sphingo_2_2 | GCTATCGGCGTTCTGAGGAATATCT | alpha_8_2 | GCCACTGTCCACCCGAGCAAGCTCG |
| archaea_3 | CGCGCCTGCTGCGCCCGTAGGGC | sphingo_2_3 | CGCTATCGGCGTTCTGAGGAATATC | alpha_8_3 | AAAACCTCTAGGTAGATACCCACGCG |
| archaea_4 | TTTCGGCCTGCTGCGCCCGTAGG | sphingo_2_4 | TCGGCGTTCTGAGGAATATCTATGC | alpha_8_4 | GTCTGCCACTGTCCACCCGAGCAAG |
| archaea_5 | TCGGCCTGCTGCGCCCCGTAGGGC | sphingo_2_5 | TTCACCCGCTACACCCCTCGTTCCGC | alpha_8_5 | CCACCCGAGCAAGCTCGGGTTTCTC |
| archaea_6 | TTCGGCCTGCTGCGCCCGTAGGG | sphingo_2_6 | TTTCACCCGCTACACCCCTCGTTCCG | alpha_8_6 | TGCCACTGTCCACCCGAGCAAGCTC |
| archaea_7 | GTGCTCCCCCGCCAATTCCTTTAAG | sphingo_2_7 | TCGCTTTCGCTTAGCCACTTACTGT | alpha_8_7 | CAAACCTCTAGGTAGATACCCACGC |
| archaea_8 | GCTCCCCCGCCAATTCCTTTAAGTT | sphingo_2_8 | CGGCGTTCTGAGGAATATCTATGCA | alpha_8_8 | TCTGCCACTGTCCACCCGAGCAAGC |
| archaea_9 | GCGCCTGCTGCGCCCCGTAGGGCCT | sphingo_2_9 | AACTAATGGGGGCATGCCCATCCC | alpha_8_9 | ACTGTCCACCCGAGCAAGCTCGGGT |
| archaea_10 | CGCCTGCTGCGCCCCGTAGGGCCTG | sphingo_2_10 | CGCTTAGCCACTTACTGTATATCGC | alpha_8_10 | CCACTGTCCACCCGAGCAAGCTCGG |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| archaea_11 | GCCTGCTGCGCCCCGTAGGGCCTGG | sphingo_2_11 | ACTAATGGGGCGCATGCCCATCCCG | alpha_8_11 | CCAAACCTCTAGGTAGATACCCACG |
| archaea_12 | GTTTCGCGCCTGCTGCGCCCCGTAG | sphingo_2_12 | GCCATGCAGCACCTCGTATAGAGTC | alpha_8_12 | GTCCACCCGAGCAAGCTCGGGTTTC |
| archaea_13 | CTTGTGGTGCTCCCCGCCAATTCC | sphingo_2_13 | AGCCATGCAGCACCTCGTATAGAGT | alpha_8_13 | TCCACCCGAGCAAGCTCGGGTTTCT |
| archaea_14 | GGTTTCGCGCCTGCTGCGCCCCGTA | sphingo_2_14 | CAGCCATGCAGCACCTCGTATAGAG | alpha_8_14 | CGTCTGCCACTGTCCACCCGAGCAA |
| archaea_15 | AGGTTTCGCGCCTGCTGCGCCCCGT | sphingo_2_15 | ACAGCCATGCAGCACCTCGTATAGA | alpha_8_15 | TGTCCACCCGAGCAAGCTCGGGTTT |
| archaea_16 | CCTGCTGCGCCCCGTAGGGCCTGGA | sphingo_2_16 | CTTACTTGTCAGCCTACGCACCCTT | alpha_8_16 | ACCCTCTAGGTAGATACCCACGCGTT |
| archaea_17 | CCTTGTGGTGCTCCCCGCCAATTC | sphingo_2_17 | ACTTACTTGTCAGCCTACGCACCCT | alpha_8_17 | CACCCGAGCAAGCTCGGGTTTCTCG |
| archaea_18 | CCCCTTGTGGTGCTCCCCGCCAAT | sphingo_2_18 | CCACTGACTTACTTGTCAGCCTACG | alpha_8_18 | TAAGCCGTCTGCCACTGTCCACCCG |
| archaea_19 | ACCCCTTGTGGTGCTCCCCGCCAA | sphingo_2_19 | CACTGACTTACTTGTCAGCCTACGC | alpha_8_19 | ACCCGAGCAAGCTCGGGTTTCTCGT |
| archaea_20 | CCCTTGTGGTGCTCCCCGCCAATT | sphingo_2_20 | GACTTACTTGTCAGCCTACGCACCC | alpha_8_20 | CCGTCTGCCACTGTCCACCCGAGCA |
| archaea_21 | CACCCCTTGTGGTGCTCCCCGCCA | sphingo_2_21 | TGACTTACTTGTCAGCCTACGCACC | alpha_8_21 | AACCCTCTAGGTAGATACCCACGCGT |
| archaea_22 | GTGTGTGCAAGGAGCAGGGACGTAT | sphingo_2_22 | CTGACTTACTTGTCAGCCTACGCAC | alpha_8_22 | GCCGTCTGCCACTGTCCACCCGAGC |
| archaea_23 | TGTGTGCAAGGAGCAGGGACGTATT | sphingo_2_23 | ACTGACTTACTTGTCAGCCTACGCA | alpha_8_23 | TAGATACCCACGCGTTACTAAGCCG |
| archaea_24 | CGGTGTGCAAGGAGCAGGGACGT | sphingo_2_24 | CCATGCAGCACCTCGTATAGAGTCC | alpha_8_24 | AAGCCCTCTGCCACTGTCCACCCGA |
| archaea_25 | GGTGTGTGCAAGGAGCAGGGACGTA | sphingo_2_25 | CGCTTTCGCTTAGCCACTTACTGTA | alpha_8_25 | GTAGATACCCACGCGTTACTAAGCC |
| bacteria_1 | CGCTCGTTGCGGGACTTAACCCAAC | sphingo_3_1 | AGTTTCCTCGAGCTATGCCCCAGTT | alpha_9_1 | TCTCCGGCGACCAAACTCCCCATGT |
| bacteria_2 | GCTCGTTGCGGGACTTAACCCAACA | sphingo_3_2 | CGAGTTTCCTCGAGCTATGCCCCAG | alpha_9_2 | CGTCTCCGGCGACCAAACTCCCCAT |
| bacteria_3 | GACTTAACCCAACATCTCACGACAC | sphingo_3_3 | GTTTCCTCGAGCTATGCCCCAGTTA | alpha_9_3 | GTCTCCGGCGACCAAACTCCCCATG |
| bacteria_4 | AACCCAACATCTCACGACACGAGCT | sphingo_3_4 | TTTCCTCGAGCTATGCCCCAGTTAA | alpha_9_4 | CTCCGGCGACCAAACTCCCCATGTC |
| bacteria_5 | ACTTAACCCAACATCTCACGACACG | sphingo_3_5 | GAGTTTCCTCGAGCTATGCCCCAGT | alpha_9_5 | GCCGTCTCCGGCGACCAAACTCCCC |
| bacteria_6 | TAACCCAACATCTCACGACACGAGC | sphingo_3_6 | TCGAGTTTCCTCGAGCTATGCCCCA | alpha_9_6 | TCCGGCGACCAAACTCCCCATGTCA |
| bacteria_7 | GGACTTAACCCAACATCTCGCCCTCG | sphingo_3_7 | TTACCGAAGTAAATGCTGCCCCTCG | alpha_9_7 | CCGTCTCCGGCGACCAAACTCCCA |
| bacteria_8 | CTTAACCCAACATCTCACGACACGA | sphingo_3_8 | GTTGCTAGCTCTACCCTAAACAGCG | alpha_9_8 | CGCCGTCTCCGGCGACCAAACTCCC |
| bacteria_9 | TTAACCCAACATCTCACGACACGAG | sphingo_3_9 | AGTTGCTAGCTCTACCCTAAACAGC | alpha_9_9 | CCGGGCGACCAAACTCCCCATGTCAA |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| bacteria_10 | GGGACTTAACCCAACATCTCACGAC | sphingo_3_10 | CCATTTACCGAAGTAAATGCTGCCC | alpha_9_10 | ACGCCGTCTCCGGCGACCAAACTCC |
| bacteria_11 | ACTGCTGCCTCCCGTAGGAGTCTGG | sphingo_3_11 | CATTTACCGAAGTAAATGCTGCCCC | alpha_9_11 | GAACTGAAGGACGCCGTCTCCGGCG |
| bacteria_12 | CTCGTTGCGGGACTTAACCCAACAT | sphingo_3_12 | CGCCATTTACCGAAGTAAATGCTGC | alpha_9_12 | CGGCGACCAAACTCCCCTTACGGTCAAG |
| bacteria_13 | CGGGACTTAACCCAACATCTCACGA | sphingo_3_13 | TTGCTAGTCTCTACCCTAAACAGCGC | alpha_9_13 | GTCGGCAGCCTCCCTTACGGGTCGG |
| bacteria_14 | TCGTTGCGGGACTTAACCCAACATC | sphingo_3_14 | GCCATTTACCGAAGTAAATGCTGCC | alpha_9_14 | GGTCGGCAGCCTCCCTTACGGGTCG |
| bacteria_15 | CGTTGCGGGACTTAACCCAACATCT | sphingo_3_15 | TCCTCGAGCTATGCCCCAGTTAAAG | alpha_9_15 | TGGTCGGCAGCCTCCCTTACGGGTC |
| bacteria_16 | GTTGCGGGACTTAACCCAACATCTC | sphingo_3_16 | TTTCCTCGAGCTATGCCCCAGTTAAA | alpha_9_16 | TCGGCAGCCTCCCTTACGGGTCGGC |
| bacteria_17 | TGCGGGACTTAACCCAACATCTCAC | sphingo_3_17 | CAGTTGCTAGTCTCTACCCTAAACAG | alpha_9_17 | GTGGTCGGCAGCCTCCCTTACGGGT |
| bacteria_18 | TTGGGGACTTAACCCAACATCTCA | sphingo_3_18 | TGCTAGTCTCTACCCTAAACAGCGCC | alpha_9_18 | CGTGGTCGGCAGCCTCCCTTACGGG |
| bacteria_19 | CCCCACTGCTGCCTCCCGTAGGAGT | sphingo_3_19 | CCGTCAGATCCTCTCGCAAGAGTAT | alpha_9_19 | CGGCAGCCTCCCTTACGGGTCGGCG |
| bacteria_20 | GCGGGACTTAACCCAACATCTCACG | sphingo_3_20 | CTCGAGCTATGCCCCAGTTAAAGGT | alpha_9_20 | CGCACCTCAGCGTCAGATCCGGACC |
| bacteria_21 | GCGCTCGTTGCGGGACTTAACCCAA | sphingo_3_21 | CCTCGAGCTATGCCCCAGTTAAAGG | alpha_9_21 | AATCTTTCCCCTCCAGGGCTTATCC |
| bacteria_22 | TCCCCACTGCTGCCTCCCGTAGGAG | sphingo_3_22 | CCAGTTGCTAGTCTCTACCCTAAACA | alpha_9_22 | CGAACTGAAGGACGCCGTCTCCGGC |
| bacteria_23 | ATTCCCCACTGCTGCCTCCCGTAGG | sphingo_3_23 | TCTCTCTGGATGTCACTGCATTCT | alpha_9_23 | TACCCCTTCTTCCGATCTCTAGCCTAG |
| bacteria_24 | TTCCCCACTGCTGCCTCCCGTAGGA | sphingo_3_24 | AtCTCTGGATGTCACTGCATTCTGCATTC | alpha_9_24 | GGCAGCCTCCCTTACGGGTCGGCGA |
| bacteria_25 | ACCCAACATCTCACGACACAGAGCTG | sphingo_3_25 | CTCTCTGGATGTCACTGCATTCTA | alpha_9_25 | GGCGACCAAACTCCCCATGTCAAGG |
| rhodobacter_1 | TCCCCAGGCGGAATGCTTAATCCGT | caldithrix_1_1 | ACTCCTCAGAGAGCTTCATCGCCCACG | alpha_10_1 | CGCACCTGAGCGTCAGATCTAGTCC |
| rhodobacter_2 | CTCCCCAGGCGGAATGCTTAATCCG | caldithrix_1_2 | CTCCTCAGAGAGCTTCATCGCCCACGC | alpha_10_2 | TCGCACCTGAGCGTCAGATCTAGTC |
| rhodobacter_3 | ACTCCCCAGGCGGAATGCTTAATCC | caldithrix_1_3 | AACAGGGCTTTACACTCCTCAGAGC | alpha_10_3 | CGTGCGCCACTCTCCAGTTCCCGAA |
| rhodobacter_4 | CCCCAGGCGGAATGCTTAATCCGTT | caldithrix_1_4 | CACTCCTCAGAGAGCTTCATCGCCCAC | alpha_10_4 | CCGTGCGCCACTCTCCAGTTCCCGA |
| rhodobacter_5 | CACCGCGTCATGCTGTTACGCGATT | caldithrix_1_5 | ACAGGGCTTTACACTCCTCAGAGCT | alpha_10_5 | CCCGTGCGCCACTCTCCAGTTCCCG |
| rhodobacter_6 | TCACCGCGTCATGCTGTTACGCGAT | caldithrix_1_6 | ACACTCCTCAGAGAGCTTCATCGCCCA | alpha_10_6 | CTGAGCGTCAGATCTAGTCCAGGTG |
| rhodobacter_7 | ATTCACCGCGTCATGCTGTTACGCG | caldithrix_1_7 | CAGGGCTTTACACTCCTCAGAGCTT | alpha_10_7 | TTCGCACCTGAGCGTCAGATCTAGT |
| rhodobacter_8 | TAGCCCAACCGTAAGGGCCATGAG | caldithrix_1_8 | TCCTCAGAGAGCTTCATCGCCCACGCG | alpha_10_8 | CCAACCGTTATCCCCACTAAGAGAG |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE |
|---|---|---|---|
| rhodobacter_9 | TACTCCCCAGGCGGAATGCTTAATC | caldithrix_1_9 | TACACTCCTCAGAGCTTCATCGCCC | alpha_10_9 | TCCAACCGTTATCCCCACTAAGAG |
| rhodobacter_10 | AGCCCAACCCGTAAGGCCATGAGG | caldithrix_1_10 | CTTTCTGGCACTCCCGACTTTCATGG | alpha_10_10 | GCACCTGAGCGTCAGATCAGTCCA |
| rhodobacter_11 | GCCCAACCCGTAAGGGCCATGAGGA | caldithrix_1_11 | TTACACTCCTCAGAGCTTCATCGCC | alpha_10_11 | CCTGAGCGTCAGATCTAGTCCAGGT |
| rhodobacter_12 | AACGTATTCACCGCGTCATGCTGTT | caldithrix_1_12 | CCTCAGAGCTTCATCGCCACGCGG | alpha_10_12 | GTTAGCCCACCGTCTTCGGTAAAA |
| rhodobacter_13 | TTCACCGCGTCATGCTGTTACGCGA | caldithrix_1_13 | CCTAACAGGGCTTTACACTCCTCAG | alpha_10_13 | CCACTAAGAGGTAGGTCCCCACGCG |
| rhodobacter_14 | ACCGCGTCATGCTGTTACGCGATTA | caldithrix_1_14 | AGGGCTTTACACTCCTCAGAGCTTC | alpha_10_14 | TGAGCCTCAGATCTAGTCCAGGTGG |
| rhodobacter_15 | GCGGAATGCTTAATCCGTTAGGTGT | caldithrix_1_15 | TTCTGGCACTCCCGACTTTCATGC | alpha_10_15 | ATCCCCACTAAGAGGTAGGTCCCC |
| rhodobacter_16 | CCAACCCGTAAGGGCCATGAGGACT | caldithrix_1_16 | TCTGGCACTCCCGACTTTCATGGCG | alpha_10_16 | GCTTTCACCCCTGACTGGCAAGACC |
| rhodobacter_17 | CCCAGGCGGAATGCTTAATCCGTTA | caldithrix_1_17 | CTCAGAGCTTCATCGCCACGCGGC | alpha_10_17 | CAACCGTTATCCCCACTAAGAGGT |
| rhodobacter_18 | CCCAACCCGTAAGGGCCATGAGGAC | caldithrix_1_18 | GGGCTTTACACTCCTCAGAGCTTCA | alpha_10_18 | GCGTCACCGAAATCGAAATCCCGAC |
| rhodobacter_19 | AATTCCACTCACCTCTCGAACTC | caldithrix_1_19 | CTCCTAACAGGGCTTTACACTCCTC | alpha_10_19 | TGCGTCACCGAAATCGAAATCCCGA |
| rhodobacter_20 | GAATTCCACTCACCTCTCGAACT | caldithrix_1_20 | CTGGCACTCCCGACTTTCATGGCGT | alpha_10_20 | CGTCACCGAAATCGAAATCCCGACA |
| rhodobacter_21 | TATTCACCGCGTCATGCTGTTACGC | caldithrix_1_21 | TCAGAGCTTCATCGCCACGCGCG | alpha_10_21 | CTGCCACCTGAGCGTCAGATCTAG |
| rhodobacter_22 | ACGTATTCACCGCGTCATGCTGTTA | caldithrix_1_22 | ACCTCTAGACAGTCCCGAAGGAAG | alpha_10_22 | TTTCGCACCTGAGCGTCAGATCTAG |
| rhodobacter_23 | GAACGTATTCACCGCGTCATGCTGT | caldithrix_1_23 | CCCTCTAACAGGGTTTTACACTCC | alpha_10_23 | CTTTCACCCCTGACTGGCAAGACCG |
| rhodobacter_24 | GGAATTCCACTCACCTCTCGAAC | caldithrix_1_24 | GGTCGAAACCTCCAACACACTAGTGC | alpha_10_24 | CTAAAAGGTTAGCCACCGTCTTCG |
| rhodobacter_25 | GTAGCCAACCCGTAAGGCCATGA | caldithrix_1_25 | GTCGAAACCTCCAACACACTAGTGC | alpha_10_25 | CCCACTAAGAGGTAGGTCCCCACGC |
| margrpA_1 | ACGAAGTTAGCCGGTGCTTTCTTGT | chloroflexi_1_1 | TCTCCGAGGAGTCGTTCCAGTTTCC | alpha_12_1 | CCGTGCGCCACTCTATAAATAGCGT |
| margrpA_2 | CACGAAGTTAGCCGGTGCTTTCTTG | chloroflexi_1_2 | CTCCGAGGAGTCGTTCCAGTTTCCC | alpha_12_2 | CCCGTGCGCCACTCTATAAATAGCG |
| margrpA_3 | GTTACTCACCCGTTCGCCAGTTTAC | chloroflexi_1_3 | ACGAATGGGTTTGACACCACCACA | alpha_12_3 | CCAACCGTTATCCCGCAGAAAAAGG |
| margrpA_4 | TAAGGGACATACTGACTTGACATCA | chloroflexi_1_4 | CGAATGGGTTTGACACCACCACCAC | alpha_12_4 | CCCGAGAAAAAGGCAGGTTCCCAC |
| margrpA_5 | ATAAGGGACATACTGACTTGACATC | chloroflexi_1_5 | CTCTCCGAGGAGTCGTTCCAGTTTC | alpha_12_5 | ACCGTTATCCCGCAGAAAAGGCAG |
| margrpA_6 | AAGGGACATACTGACTTGACATCAT | chloroflexi_1_6 | TCCGAGGAGTCGTTCCAGTTTCCT | alpha_12_6 | CAACCGTTATCCCGCAGAAAACGC |
| margrpA_7 | TTACTCACCCGTTCGCCAGTTTACT | chloroflexi_1_7 | GAATGGGTTTGACACCACCACACC | alpha_12_7 | CGTTCAAACCGTTATCCCGCAGAA |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| margrpA_8 | CGTTACTCACCCGTTCGCCAGTTTA | chloroflexi_1_8 | GCTCTCCGAGGAGTCGTTCCAGTTT | alpha_12_8 | CCGCAGAAAAGGCAGGTTCCCACG |
| margrpA_9 | GCGTTACTCACCCGTTCGCCAGTTT | chloroflexi_1_9 | CCGAGGAGTCGTTCCAGTTTCCCTT | alpha_12_9 | CGCAGAAAAGGCAGGTTCCCACGC |
| margrpA_10 | CGCGTTACTCACCCGTTCGCCAGT | chloroflexi_1_10 | CGCTCTCCGAGGAGTCGTTCCAGTT | alpha_12_10 | CCGTTATCCCGCAGAAAAGGCAGG |
| margrpA_11 | ACATACTGACTTGACATCATCCCCA | chloroflexi_1_11 | AATGGGTTTGACACCACCACCT | alpha_12_11 | CGTTATCCCGCCACTCTATAAATGC |
| margrpA_12 | TACTGACTTGACATCATCCCCACCT | chloroflexi_1_12 | CGAGGAGTCGTTCCAGTTTCCCTTC | alpha_12_12 | ACCCGTGCGCCACTCTATAAATAGC |
| margrpA_13 | GGACATACTGACTTGACATCATCCC | chloroflexi_1_13 | AGGAGTCGTTCCAGTTTCCCTTCAC | alpha_12_13 | CACCCGTGCGCCACTCTATAAATAG |
| margrpA_14 | GACATACTGACTTGACATCATCCCC | chloroflexi_1_14 | GAGGAGTCGTTCCAGTTTCCCTTCA | alpha_12_14 | TCCCCGAGAAAAGGCAGGTTCCCA |
| margrpA_15 | ATACTGACTTGACATCATCCCCACC | chloroflexi_1_15 | CGCTTTGCGACATGAGCGTCAGGTT | alpha_12_15 | GCAGAAAAGGCAGGTTCCCACGCG |
| margrpA_16 | CATACTGACTTGACATCATCCCCAC | chloroflexi_1_16 | TGAGCGTCAGGTTCAATGCCCAGGT | alpha_12_16 | GGAAACCAAACTCCCCATGTCAAGG |
| margrpA_17 | AGGGACATACTGACTTGACATCATC | chloroflexi_1_17 | ACGCTTTGCGACATGAGCGTCAGT | alpha_12_17 | CCTCCTGCAAGCAGGTTAGCTCACC |
| margrpA_18 | GGGACATACTGACTTGACATCATCC | chloroflexi_1_18 | TCCCCACGCTTTGCGACATGAGCGT | alpha_12_18 | TTTCGCGCCCTCAGCGTCGTCAAATCGG |
| margrpA_19 | ACGCGTTACTCACCCGTTCGCCAGT | chloroflexi_1_19 | TCAGGTTCAATGCCAGGTACCCCT | alpha_12_19 | TTCGCGCCTCAGCGTCAAAATCGGA |
| margrpA_20 | GCACGAAGTTAGCCGGTGCTTTCTT | chloroflexi_1_20 | ATCATCTCGGCCTTCACGTTCGACT | alpha_12_20 | ACTCCCCATGTCAAGGACTGTAAG |
| margrpA_21 | GGCACGAAGTTAGCCGGTGCTTTCT | chloroflexi_1_21 | TGCGACATGAGCGTCAGGTTCAATG | alpha_12_21 | GCCTCCTGCAAGCAGGTTAGCTCAC |
| margrpA_22 | TGGGCACGAAGTTAGCCGGTGCTTT | chloroflexi_1_22 | ATGAGCGTCAGGTTCAATGCCAGGG | alpha_12_22 | CAGAAAAGGCAGGTTCCCCACGCGT |
| margrpA_23 | ACTGACTTGACATCATCCCCACCTT | chloroflexi_1_23 | CACGCTTTGCGACATGAGCGTCAGG | alpha_12_23 | TCCGGCGGACCTTTCTCCGGCGACCTTTC |
| margrpA_24 | CTGGCACGAAGTTAGCCGGTGCTTT | chloroflexi_1_24 | CATGAGCGTCAGGTTCAATGCCAGG | alpha_12_24 | CCCCTCTTTCTCCGGCGGACCTTTC |
| margrpA_25 | ACGATTACTAGCGATTCCTGCTTCA | chloroflexi_1_25 | GTAATCATCTCGGCCTTCAGGTTCG | alpha_12_25 | CCCCTCTTTCTCCGGCGGACCTTTC |
| vibrionaceae_1 | TATCCCCCACATCAGGGCAATTTCC | chloroflexi_2_1 | GGTGACTCCCCTTTCAGGTTGCTAC | alpha_13_1 | TCTAACTGTTCAAGCAGCCTGCGAG |
| vibrionaceae_2 | CGACATTACTCGCTGGCAAACAAGG | chloroflexi_2_2 | AGGTGACTCCCCTTTCAGGTTGCTA | alpha_13_2 | CTAACTGTTCAAGCAGCCTGCGAGC |
| vibrionaceae_3 | CCGACATTACTCGCTGGCAAACAAG | chloroflexi_2_3 | CCCTCCCCATTAAGCGGGGAGATTT | alpha_13_3 | TAACTGTTCAAGCAGCCTGCGAGCC |
| vibrionaceae_4 | CCCCACATCAGGGCAATTTCCTAGG | chloroflexi_2_4 | GCAAGTTGGCTCATCGGTACCGTT | alpha_13_4 | GTCTAACTGTTCAAGCAGCCTGCGA |
| vibrionaceae_5 | CCCCTACATCAGGGCAATTTCCTAG | chloroflexi_2_5 | CTCTCCCGATGTTCCAAGCAAGCTT | alpha_13_5 | CGCTCCTCAGCGTCAGAAATAGCC |
| vibrionaceae_6 | CCCCATCAGGGCAATTTCCTAGGC | chloroflexi_2_6 | CCCCTCCCCATTAAGCGGGGAGATT | alpha_13_6 | GCTCCTCAGCGTCAGAAATAGCCA |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| vibrionaceae_7 | CCACATCAGGGCAATTTCCTAGGCA | chloroflexi_2_7 | TTCCAAGCAAGCTTGGCTCATCGGT | alpha_13_7 | TCGCTCCTCAGCGTCAGAAAATAGC |
| vibrionaceae_8 | TCCCCACATCAGGGCAATTTCCTA | chloroflexi_2_8 | AGCAAGCTTGGCTCATCGGTACCGT | alpha_13_8 | CGTCTAACTGTTCAAGCAGCCTGCG |
| vibrionaceae_9 | CCCGACATTACTCGCTGGCAAACAA | chloroflexi_2_9 | ACTCTCCCGATGTTCCAAGCAAGCT | alpha_13_9 | AACTGTTCAAGCAGCCTGCGAGCCC |
| vibrionaceae_10 | ATCCCCCACATCAGGGCAATTTCCT | chloroflexi_2_10 | ACCCCTCCCCATTAAGCGGGAGAT | alpha_13_10 | CACGTCGAACTGTTCAAGCAGCCTG |
| vibrionaceae_11 | TGGTTATCCCCCACATCAGGGCAAT | chloroflexi_2_11 | TCTCCCGATGTTCCAAGCAAGCTTG | alpha_13_11 | ACGTCTAACTGTTCAAGCAGCCTGC |
| vibrionaceae_12 | CCCCCACATCAGGGCAATTTCCCAG | chloroflexi_2_12 | CTCCCGATGTTCCAAGCAAGCTTGG | alpha_13_12 | ACTGTTCAAGCAGCCTGCGAGCCCT |
| vibrionaceae_13 | TCCCCACATCAGGGCAATTTCCCA | chloroflexi_2_13 | AATGACCCCTCCCCATTAAGCGGG | alpha_13_13 | CCGGGGATTTCACGTCTAAGTCTTC |
| vibrionaceae_14 | CCCCACATCAGGGCAATTTCCCAGG | chloroflexi_2_14 | GAATGACCCCTCCCCATTAAGCGG | alpha_13_14 | CTCCTCAGCGTCAGAAAATAGCCAG |
| vibrionaceae_15 | CCCCACATCAGGGCAATTTCCCAGGC | chloroflexi_2_15 | GTTCCAAGCAAGCTTGGCTCATCGG | alpha_13_15 | TTCAAGCAGCCTGCGAGCCCTTTAC |
| vibrionaceae_16 | CACATCAGGGCAATTTCCCAGGCAT | chloroflexi_2_16 | CGAATGACCCCTCCCCATTAAGCGG | alpha_13_16 | TGTTCAAGCAGCCTGCGAGCCCTTT |
| vibrionaceae_17 | CCAATCAGGGCAATTTCCCAGGCA | chloroflexi_2_17 | TGTTCCAAGCAAGCTTGGCTCATCG | alpha_13_17 | CTGTTCAAGCAGCCTGCGAGCCCTT |
| vibrionaceae_18 | ATCCCCCACATCAGGGCAATTTCCC | chloroflexi_2_18 | TCGAATGACCCCTCCCCATTAAGCG | alpha_13_18 | GTTCAAGCAGCCTGCGAGCCCTTTA |
| vibrionaceae_19 | TCCCGACATTACTCGCTGGCAAACA | chloroflexi_2_19 | AAGCAAGCTTGGCTCATCGGTACCG | alpha_13_19 | CGGCATTGCTGGATCAGAGTTGCCT |
| vibrionaceae_20 | GGTTATCCCCCACATCAGGGCAATT | chloroflexi_2_20 | TGACCCCTCCCCATTAAGCGGGGAG | alpha_13_20 | GGCATTGCTGGATCAGAGTTGCCTC |
| vibrionaceae_21 | CGCAAGTTGCCGCCCTCTGTATGC | chloroflexi_2_21 | CCACTCTCCCGATGTTCCAAGCAAG | alpha_13_21 | CGCGGCATTGCTGGATCAGAGTTGC |
| vibrionaceae_22 | GCAAGTTGGCGCGCCCTCTGTATGCG | chloroflexi_2_22 | CCTCCCCATTAAGCGGGAGAGATTTC | alpha_13_22 | GCATTGCTGGATCAGAGTTGCCTCC |
| vibrionaceae_23 | ATGGTTATCCCCCACATCAGGGCAA | chloroflexi_2_23 | CAAGCTTGGCTCATCGGTACCGTTC | alpha_13_23 | GCGGGCATTGCTGGATCAGAGTTGCC |
| vibrionaceae_24 | ACTCGCTGGCAAACAAGGATAAGGG | chloroflexi_2_24 | CCGATGTTCCAAGCAAGCTTGGCTC | alpha_13_24 | CCCGGGGATTTCACGTCTAACTGTT |
| vibrionaceae_25 | CGCATCTGAGTGTCAGTATCTGTCC | chloroflexi_2_25 | CACTCTCCCGATGTTCCAAGCAAGC | alpha_13_25 | ACGCGGCATTGCTGGATCAGAGTTG |
| alteromonadales_1 | CCCCACTTGGGCCAATCTAAAGGCGA | chlorella_pl_1 | CGCCACTCATCGCAATCTGGCAAGC | delta_1_1 | CCGAACTACGAACTGCTTTCTGGA |
| alteromonadales_2 | ATCCCCACTTGGGCCAATCTAAAGGC | chlorella_pl_2 | GCCACTCATCGCAATGTGGCAAGCC | delta_1_2 | TCCGAACTACGAACTGCTTTCTGGG |
| alteromonadales_3 | TCCCACTTGGGCCAATCTAAAGGCG | chlorella_pl_3 | CCACTCATCGCAATCTGGCAAGCCA | delta_1_3 | TTGCTGCGGCACAGCAGGGGTCAAT |
| alteromonadales_4 | CACTTGGGCCAATCTAAAGGCGAG | chlorella_pl_4 | CACTCATCGCAATCTGGCAAGCCAA | delta_1_4 | GTTTGCTGCGGCACACAGCAGGGGTCA |
| altermaonadales_5 | CACTTGGGCCAATCTAAAGGCGAGA | chlorella_pl_5 | GCAAGCCAAATTGCATGAGTACGAC | delta_1_5 | TTTGCTGCGGCACACAGCAGGGGTCAA |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| alteromonadales_6 | ACTTTGGGCCAATCTAAAGGCGAGAG | chlorella_p1_6 | GCCAAATTGCATGCGTACGACTTGC | delta_1_6 | TTGCCCAACGACTTCTGGTACAACC |
| alteromonadales_7 | CTTGGGCCAATCAAAGGCGAGAGC | chlorella_p1_7 | TGGCAAGCCAAATTGCATGCGTACG | delta_1_7 | GGTTTGCCCAACGACTTCTGGTACA |
| alteromonadales_8 | CACCTCAAGGCATGTTCCCAAGCAT | chlorella_p1_8 | CTGTGTCCACTCTGGAACTTCCCCT | delta_1_8 | TCCCCGAAGGGTTTGCCCAACGACT |
| alteromonadales_9 | TGAGCGTCAGTGTTGACCCAGGTGG | chlorella_p1_9 | CCGTCCGCCACTCATCGCAATCTGG | delta_1_9 | CCCCGAAGGGTTTGCCCAACGACTT |
| alteromonadales_10 | CGAAGCCCCCTTTGGTCCGTAGACA | chlorella_p1_10 | CCGCCACTCATCGCAATCTGGCAAG | delta_1_10 | CCGAAGGGTTTGCCCAACGACTTCT |
| alteromonadales_11 | ACAGAACCGAGGTTCCGAGCTTCTA | chlorella_p1_11 | CGTCCGCCACTCATCGCAATCTCGC | delta_1_11 | CCCGAAGGGTTTGCCCAACGACTTC |
| alteromonadales_12 | CAGAACCGAGGTTCCGAGCTTCTAG | chlorella_p1_12 | CCTGTGTCCACTCTGGAACTTCCCC | delta_1_12 | CCCGGGCTTTCACACCTGACTTAAA |
| alteromonadales_13 | AGAACCGAGGTTCCGAGCTTCTAGT | chlorella_p1_13 | GTCCGCCACTCATCGCAATCTGGCA | delta_1_13 | GCTTCCTTCAGTGGTACCGTCAACA |
| alteromonadales_14 | GAAAAACAGAACCGAGGTTCCGAGC | chlorella_p1_14 | TCCGCCACTCATCGCAATCTGGCAA | delta_1_14 | AGGGCGCTGCATCCCCGAAGGGTTT |
| alteromonadales_15 | GAACCGAGGTTCCGAGCTTCTAGTA | chlorella_p1_15 | ACCTGTGTCCACTCTGGAACTTCCC | delta_1_15 | GGCGCCTGCATCCCCGAAGGGTTTG |
| alteromonadales_16 | CCGAGGTTCCGAGCTTCTAGTAGAC | chlorella_p1_16 | GGCAAGCCAAATTGCATGCGTACGA | delta_1_16 | GCGCCTGCATCCCCGAAGGGTTTGC |
| alteromonadales_17 | CGAGGTTCCGAGCTTCTAGTAGACA | chlorella_p1_17 | CTGGCAAGCCAAATTGCATGCGTAC | delta_1_17 | GCATCCCCGAAGGGTTTGCCCAACG |
| alteromonadales_18 | AACCGAGGTTCCGAGCTTCTAGTAG | chlorella_p1_18 | CCCGTCCGCCACTCATCGCAATCTG | delta_1_18 | ATCCCCGAAGGGTTTGCCCAACGAC |
| alteromonadales_19 | ACCGAGGTTCCGAGCTTCTAGTAGA | chlorella_p1_19 | CACCTGTGCCACTCTGGAACTTTCC | delta_1_19 | CATCCCCGAAGGGTTTGCCCAACGA |
| alteromonadales_20 | AACAGAACCGAGGTTCCGAGCTTCT | chlorella_p1_20 | ACCCGTCCGCCACTCATCGCAATCT | delta_1_20 | ACCTTAGGCGCCTGCATCCCCGAAG |
| alteromonadales_21 | AAACAGAACCGAGGTTCCGAGCTTC | chlorella_p1_21 | CCACCTGTGTCCACTCTGGAACTTC | delta_1_21 | CCTTAGGCGCCTGCATCCCCGAAGG |
| alteromonadales_22 | CCGAAGCCCCCTTTGGTCCGTAGAC | chlorella_p1_22 | CACCCGTCCGCCACTCATCGCAATC | delta_1_22 | TACCTTAGGCGCCTGCATCCCCGAA |
| alteromonadales_23 | GAAGCCCCCTTTGGTCCGTAGACAT | chlorella_p1_23 | TCACCCGTCCGCCACTCATCGCAAT | delta_1_23 | ATACCTTAGGCGCCTGCATCCCCGA |
| alteromonadales_24 | AAGCCCCCTTTGGTCCGTAGACATT | chlorella_p1_24 | ACCACCTGTGTCCACTCTGGAACTT | delta_1_24 | CTTAGGCGCCTGCATCCCCGAAGGG |
| alteromonadales_25 | CCACCTCAAGGCATGTTCCCAAGCA | chlorella_p1_25 | CACCACCTGTGTCCACTCTGGAACT | delta_1_25 | CATACCTTAGGCGCCTGCATCCCCG |
| polaribacters_1 | GCCAGATGGCTGCTCATTGTCCATA | plastid_1_1 | GGTCTCACGACTTGGCATCTCATTG | delta_2_1 | CTCCAGTCTTTCGATAGGATTCCCG |
| polaribacters_2 | TGCCAGATGGCTGCTCATTGTCCAT | plastid_1_2 | TCTCCCTAGGCAGGTTTTTGACCTG | delta_2_2 | GGCCACCCTTGATCCAAAAACCCGA |
| polaribacters_3 | TTGCCAGATGGCTGCTCATTGTCCA | plastid_1_3 | CCACGTGGATTCGATACACGCAATG | delta_2_3 | AGGCCACCCTTGATCCAAAAACCCG |
| polaribacters_4 | CCAGATGGCTGCTCATTGTCCATAC | plastid_1_4 | ATGCACCACCTGTATGTGTCTGCCG | delta_2_4 | AAGGGCACTCCAGTCTTTCGATAGG |

TABLE 1-continued list of probes specific for laboratory bacterial strains and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| polaribacters_5 | GTTGCCAGATGGCTGCTCATTGTCC | plastid_1_5 | CACCACCTGTATGTGTCTGCCGAAG | delta_2_5 | GAGGCCACCCTTGATCCAAAAACCC |
| polaribacters_6 | TCCCTCAGCGTCAGTACATACGTAG | plastid_1_6 | AACACCACGTGGATTCGATACACGC | delta_2_6 | GAAGGGCACTCCAGTCTTTCGATAG |
| polaribacters_7 | CCCTCAGCGTCAGTACATACGTAGT | plastid_1_7 | ACCACCTGTATGTGTCTGCCGAAGC | delta_2_7 | ACCCTAGCAAGCTAGAGTGTTCTCG |
| polaribacters_8 | GTCCCTCAGCGTCAGTACATACGTA | plastid_1_8 | CTTCTCCCTAGGCAGGTTTTTGACC | delta_2_8 | AGAGGCCACCCTTGATCCAAAAACC |
| polaribacters_9 | CAGATGGCTGCTCATTGTCCATACC | plastid_1_9 | TGCACCACCTGTATGTGTCTGCCGA | delta_2_9 | AGAGGCCACCCTTGATCCAAAAACC |
| polaribacters_10 | TTCGCATAGTGGCTGCTCATTGTCC | plastid_1_10 | ACACCACCTGGATTCGATACACCCA | delta_2_10 | ACATGTAGAGGCCACCCTTGATCCA |
| polaribacters_11 | CGTCCCTCAGCGTCAGTACATACGT | plastid_1_11 | CCACCTGTATGTGTCTGCCGAAGCA | delta_2_11 | TACATGTAGAGGCCACCCTTGATCC |
| polaribacters_12 | AGACCCCTACCTATCGTTGCCATG | plastid_1_12 | GCACCACCTGTATGTGTCTGCCGAA | delta_2_12 | CCCCGAAGGGCACTCCAGTCTTTCG |
| polaribacters_13 | CGCTTAGTCACTGAGCTAATGCCCA | plastid_1_13 | CACCACGTGGATTCGATACACGCAA | delta_2_13 | CCCTAGCAAGCTAGAGTGTTCTCGT |
| polaribacters_14 | TGTTGCCAGATGGCTGCTCATTGTC | plastid_1_14 | CTCACGACTTGGCATCAGAAACTTCC | delta_2_14 | GCTTACATGTAGAGGCCACCCTTGA |
| polaribacters_15 | GATTCGCTCCTATTCGCATAGTGGC | plastid_1_15 | CAGGTACACGTCAGAGTTTTTGACCGT | delta_2_15 | GGGCACTCCAGTCTTTCGATAGGAT |
| polaribacters_16 | TCGTCCCTCAGCGTCAGTACATACG | plastid_1_16 | CTCCCTAGGCAGGTTTTTGACCTGT | delta_2_16 | CCGAAGGGCACTCCAGTCTTTCGAT |
| polaribacters_17 | TCGTTAGTCACTGAGCTAATGCCC | plastid_1_17 | CGTTCTCACGACTTGGCATCATT | delta_2_17 | CGAAGGGCACTCCAGTCTTTCGATA |
| polaribacters_18 | TCGCATAGTGGCTGCTCATTGTCCA | plastid_1_18 | GACCAACTACTGATCGTCACCTTGG | delta_2_18 | AGGGGCACTCCAGTCTTTCGATAGGA |
| polaribacters_19 | CAGACCCCCTACCTATCGTTGCCAT | plastid_1_19 | GTTCTCCCTAGGCAGGTTTTTGAC | delta_2_19 | CCCGAAGGGCACTCCAGTCTTTCGA |
| polaribacters_20 | TTCGTCCCTCAGCGTCAGTACATAC | plastid_1_20 | CACCTGTATGTGTCTGCCGAAGCAC | delta_2_20 | CCAGTCTTTCGATAGGATTCCCGGG |
| polaribacters_21 | CTCTCTGTTGCCAGATGGCTGCTCA | plastid_1_21 | CTGTATGTGTCTGCCGAAGCACTTC | delta_2_21 | TCCAGTCTTTCGATAGGATTCCCGG |
| polaribacters_22 | GCAGATTCTATACGCGTTACGCACC | plastid_1_22 | CATGCACACCTGTATGTGTCTGCC | delta_2_22 | GTCTTTTCGATAGGATTCCCGGGATG |
| polaribacters_23 | GGCAGATTCTATACGCGTTACGCAC | plastid_1_23 | AGGTACACGTCAGAACTTCCTCCC | delta_2_23 | CTTTCGATAGGATTCCCGGGATGTC |
| polaribacters_24 | CACCTCTGACTTAATTGACCGCCTG | plastid_1_24 | TCGGTCTCACGACTTGGCATCTCAT | delta_2_24 | CAGTCTTTCGATAGGATTCCCGGGA |
| polaribacters_25 | CCTTCTGACTTAATTGACCGCCTGCG | plastid_1_25 | CCTTCTACTTCGACTTCTACTCCGAGC | delta_2_25 | GGGCTCCCCGAAGGGCACTCCAGTC |
| desulfovibrionales_1 | CCCGAGCATGCTGATCTCGAATTAC | plastid_2_1 | CAGGTAACGTCAGAACTTCCTCCCT | delta_31 | GGCACAGAAAGGGTCAACACTTCCT |
| desulfovibrionales_2 | CACCCGAGCATGCTGATCTCGAATT | plastid_2_2 | AGGTAACGTCAGAACTTCCTCCCTG | delta_3_2 | TCGGCACAGAAAGGTCAACACTTC |
| desulfovibrionales_3 | TCACCCGAGCATGCTGATCTCGAAT | plastid_2_3 | GGTAACGTCAGAACTTCCTCCCTGA | delta_3_3 | CGGCACAGAAAGGGTCAACACTTCC |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| desulfovibrionales_4 | TTCACCCGAGCATGCTGATCTCGAA | plastid_2_4 | TCAGGTAACGTCAGAACTTCCTCCC | delta_3_4 | CTTCGGCACAGAAAGGGTCAACACT |
| desulfovibrionales_5 | GCACCCTCTAATTTCCTAGAGGTCC | plastid_2_5 | CGCGTTAGCTATAATACCGCATGGG | delta_3_5 | CACTTTACTCTCCCGACGAATCGGA |
| desulfovibrionales_6 | AGGGCACCCTCTAATTTCCTAGAGG | plastid_2_6 | AATACCGCATGGGTCGATACATGCG | delta_3_6 | CCACTTTACTCTCCCGACGAATCGG |
| desulfovibrionales_7 | GGGCACCCTCTAATTTCCTAGAGGT | plastid_2_7 | CTGTATGTACGTTCCCGAAGGTGGT | delta_3_7 | GCTTCGGCACAGAAAGGGTCAACAC |
| desulfovibrionales_8 | CCCTCTAATTTCCTAGAGGTCCCCT | plastid_2_8 | CCTGTATGTACGTTCCCGAAGGTGG | delta_3_8 | CTCTCCCGACGAATCGGAATTTCTC |
| desulfovibrionales_9 | ACCCTCTAATTTCCTAGAGGTCCCC | plastid_2_9 | TCAGCCGCGAGCTCCTCTCTAGGCA | delta_3_9 | CCGACGAATCGGAATTTCTCGTTCG |
| desulfovibrionales_10 | ATTTCCTAGAGGTCCCCTGATGTC | plastid_2_10 | ATACCGCATGGGTCGATACATGCGA | delta_3_10 | GCCACTTTACTCTCCCGACGAATCG |
| desulfovibrionales_11 | AGGGTACCGTCAAATGCCTACCCTA | plastid_2_11 | ACCTGTATGTACGTTCCCGAAGGTG | delta_3_11 | AGCTTCGGCACAGAAAGGGTCAACA |
| desulfovibrionales_12 | GAGGGTACCGTCAAATGCCTACCCT | plastid_2_12 | GCCGCGAGCTCCTCTCTAGGCAGAA | delta_3_12 | ACTCTCACGAGTTCGCTACCCTTTG |
| desulfovibrionales_13 | GGGTACCGTCAAATGCCTACCCTAT | plastid_2_13 | GCGCCTTCCTCCAAACGGTTAGAAT | delta_3_13 | TCTCCCGACGAATCGGAATTTCTCG |
| desulfovibrionales_14 | TTTCCTAGAGGTCCCCTGATGTCA | plastid_2_14 | AGCCGCGAGCTCCTCTCTAGGCAGA | delta_3_14 | TAGCTTCGGCACAGAAAGGGTCAAC |
| desulfovibrionales_15 | TTCCTAGAGGTCCCCTGATGTCAA | plastid_2_15 | CAGCCGCGAGCTCCTCTCTAGGCAG | delta_3_15 | CTCTCACGAGTTCGCTACCCTTTGT |
| desulfovibrionales_16 | TGAGGGTACCGTCAAATGCCTACCC | plastid_2_16 | CACCTGTATGTACGTTCCCGAAGGT | delta_3_16 | GTGCTGGTTACACCCGAAGGCAATC |
| desulfovibrionales_17 | CTCTAATTTCCTAGAGGTCCCCTGG | plastid_2_17 | AATCAGCCGCGAGCTCCTCTCTAGG | delta_3_17 | CGCCACTTTACTCTCCCGACGAATC |
| desulfovibrionales_18 | CACCCTCTAATTTCCTAGAGGTCCC | plastid_2_18 | TAATCAGCCGCGAGCTCCTCTCTAG | delta_3_18 | CTCCCGACGAATCGGAATTTCTCGT |
| desulfovibrionales_19 | GGCACCCTCTAATTTCCTAGAGGTC | plastid_2_19 | ATCAGCCGCGAGCTCCTCTCTAGGC | delta_3_19 | CTTACTCTCACGAGTTCGCTACCCT |
| desulfovibrionales_20 | CCCTCTAATTTCCTAGAGGTCCCTG | plastid_2_20 | GGCGCCTTCCTCCAAACGGTTAGAA | delta_3_20 | TGTGCTGGTTACACCCGAAGGCAAT |
| desulfovibrionales_21 | CAACCGTTATCCCGTTCTTGAAGGT | plastid_2_21 | CCGGAGCTCCTCTCTAGGCAGAAA | delta_3_21 | CTCACGAGTTCGCTACCCTTTGTAC |
| desulfovibrionales_22 | ATCAAAGGCTGTTCCACCGTTGAGC | plastid_2_22 | GCATGGGTCGATACATGCGACATCT | delta_3_22 | CTGTGCTGGTTACACCCGAAGGCAA |
| desulfovibrionales_23 | TTGCTCGTTAGCTCGCCGGCTTCGG | plastid_2_23 | CCGCATGGGTCGATACATGCGACAT | delta_3_23 | TCGCCACTTTACTCTCCCGACGAAT |
| desulfovibrionales_24 | ATTGCTCGTTAGCTCGCCGGCTTCG | plastid_2_24 | TACCGCATGGGTCGATACATGCGAC | delta_3_24 | CCTGTGCTGGTTACACCCGAAGGCA |
| desulfovibrionales_25 | CCTAGAGGTCCCCTGGATGTCAAGC | plastid_2_25 | ACCGCATGGGTCGATACATGCGACA | delta_3_25 | GCTTACTCTCACGAGTTCGCTACCC |
| aquaficae_1 | AACCAGACGCTCCACCGGTTGTGCC | plastid_3_1 | CACCGTCGTATATCTGACCGACGAT | altero_1_1 | CCCACTTGGGCCAATCAATCTAAAGGCGA |
| aquaficae_2 | ACCAGACGCTCCACCGGTTGTGCCG | plastid_3_2 | TTCACCGTCGTATATCTGACCGACG | altero_1_2 | ATCCCACTTGGGCCAATCAATCTAAAGGC |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| aquaficae_3 | AAACCAGACGCTCCACCGGTTGTGC | plastid_3_3 | TCACCGTCGTATATCTGACCGACGA | altero_1_3 | TCCCACTTGGGCCAATCTAAAGGCG |
| aquaficae_4 | TGCCACTGTAGCGCCTGTGTAGCCC | plastid_3_4 | GTAGCCGAGTTTCAGGCTACAATCC | altero_1_4 | CCACTTGGGCCAATCTAAAGGCGAG |
| aquaficae_5 | TAAACCAGACGCTCCACCGGTTGTG | plastid_3_5 | TAGCCGAGTTTCAGGCTACAATCCG | altero_1_5 | CACTTGGGCCAATCTAAAGGCGAGA |
| aquaficae_6 | GCCACTGTAGCGCCTGTGTAGCCCA | plastid_3_6 | GACCTCATCCTCACCTTCCTCCAAT | altero_1_6 | ACTTGGGCCAATCTAAAGGCGAGAG |
| aquaficae_7 | CCAGACGCTCCACCGGTTGTGCGGG | plastid_3_7 | AGCCGAGTTTCAGGCTACAATCCGA | altero_1_7 | CTTGGGCCAATCTAAAGGCGAGAGC |
| aquaficae_8 | CCACTGTAGCGCCTGTGTAGCCCAG | plastid_3_8 | GCCGAGTTTCAGGCTACAATCCGAA | altero_1_8 | CTGTCAGTAACGTCACAGCTAGCAG |
| aquaficae_9 | GCATAAAGGGCATACTGACCTGACG | plastid_3_9 | CCGAGTTTCAGGCTACAATCCGAAC | altero_1_9 | ACAGAACCGAGGTTCCGAGCTTCTA |
| aquaficae_10 | TTAAACCAGACGCTCCACCGGTTGT | plastid_3_10 | CTCCCGTAGGAGTCTGTTCCGTTCT | altero_1_10 | CAGAACCGAGGTTCCGAGCTTCTAG |
| aquaficae_11 | CATTGCCCACGATTCCCCACTGCTG | plastid_3_11 | CCTTCCCGTAGGAGTCTGTTCCGTTC | altero_1_11 | AGAACCGAGGTTCCGAGCTTCTAGT |
| aquaficae_12 | ATTGCCCACGATTCCCCACTGCTGC | plastid_3_12 | TCCCGTAGGAGTCTGTTCCGTTCTA | altero_1_12 | GAAAAACAGAACCGAGGTTCCGAGC |
| aquaficae_13 | CCATTGCCCACGATTCCCCACTGCT | plastid_3_13 | CCCGTAGGAGTCTGTTCCGTTCTAA | altero_1_13 | GAACCGAGGTTCCGAGCTTCTAGTA |
| aquaficae_14 | GCCCATTGCCCACGATTCCCCACTG | plastid_3_14 | TGACCTCATCCTCACCTTCCTCCAA | altero_1_14 | CCGAGGTTCCGAGCTTCTAGTAGAC |
| aquaficae_15 | CCCCATTGCCCACGATTCCCCACTG | plastid_3_15 | CTAAAGCATTCATCCTCCACGCGGT | altero_1_15 | CGAGGTTCCGAGCTTCTAGTAGACA |
| aquaficae_16 | CGCCCATTGCCACGATTCCCCACT | plastid_3_16 | CCTAAAGCATTCATCCTCCACGCGG | altero_1_16 | AACCGAGGTTCCGAGCTTCTAGTAG |
| aquaficae_17 | TGCCCACGATTCCCCACTGCTGCCC | plastid_3_17 | CCCTAAAGCATTCATCCTCCACGCG | altero_1_17 | ACCGAGGTTCCGAGCTTCTAGTAGA |
| aquaficae_18 | ATTAAACCAGACGCTCCACCGGTTG | plastid_3_18 | ACCCTAAAGCATTCATCCTCCACGC | altero_1_18 | AACAGAACCGAGGTTCCGAGCTTCT |
| aquaficae_19 | TTGCCCACGATTCCCCACTGCTGCC | plastid_3_19 | ACATAAGGGCATGCTGACTTGACC | altero_1_19 | AAACAGAACCGAGGTTCCGAGCTTC |
| aquaficae_20 | GCCCACGATTCCCCACTGCTGCCCC | plastid_3_20 | GTTCCGTTCTAAATCCCAGTGTGGC | altero_1_20 | CCAACTGTTGTCCCCACCTCAAGG |
| aquaficae_21 | CAGACGCTCCACCGGTTGTGCGGGC | plastid_3_21 | CATAAGGGCATGCTGACTTGACCT | altero_1_21 | CCGGACTACGACGCACTTAAGTGA |
| aquaficae_22 | GGCATAAAGGGCATACTGACCTGAC | plastid_3_22 | GCGGTATTGCTTGGTCAAGCTTTCG | altero_1_22 | TGGGCCAATCTAAAGGCGAGAGCCG |
| aquaficae_23 | GCAGTTCGGAATGCCTTGCCGAAGT | plastid_3_23 | CGGTATTGCTTGGTCAAGCTTTCGC | altero_1_23 | GGGCCAATCTAAAGGCGAGAGCCGA |
| aquaficae_24 | CAGTTCGGAATGCCTTGCCGAAGTT | plastid_3_24 | CACGCGGTATTGCTTGGTCAAGCTT | altero_1_24 | TTGGGCCAATCTAAAGGCGAGAGCC |
| aquaficae_25 | CGCAGTTCGGAATGCCTTGCCGAAG | plastid_3_25 | CATCCTCCACGCGGTATTGCTTGGT | altero_1_25 | GGTTCCGAGCTTCTAGTAGACATCG |
| bacilli_1 | CACTCTGCTCCGAGGAGGAGAAGCCC | plastid_4_1 | CTTAAGCGCCGCCCTCCGAATGTT | altero_2_1 | TCTCACTTGGGCCTCTCTTGCGCC |

TABLE 1-continued list of probes specific for laboratory bacterial strains and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| bacilli_2 | GTCACTCTGCTCCCGAAGGAGAAGC | plastid_4_2 | CCTTAAGCGCCCCTTCCGAATGGT | altero_2_2 | CCCCTCGCAAAGGCAAGTTCCCAAG |
| bacilli_3 | CTGCTCCCGAAGGAGAAGCCCTATC | plastid_4_3 | TACCTTAAGCGCCGCCCTCCGAATG | altero_2_3 | CCCTCGCAAAGGCAAGTTCCCAAGC |
| bacilli_4 | TCACTCTGCTCCCGAAGGAGAAGCC | plastid_4_4 | ACCTTAAGCGCCGCCCTCCGAATGG | altero_2_4 | TCACTTGGGCCTCTCTCTTTGCGCCGG |
| bacilli_5 | TCTGCTCCCGAAGGAGAAGCCCTAT | plastid_4_5 | AGCCCTACCTTAAGCGCCCCTCC | altero_2_5 | CTTGGGCCTCTCTCTTTGCGCCGAGC |
| bacilli_6 | TGCTCCCGAAGGAGAAGCCCTATCT | plastid_4_6 | TTAAGCGCCGCCCTCCGAATGGTTA | altero_2_6 | CGACATTCTTTAAGGGGTCCGCTCC |
| bacilli_7 | CTCTGCTCCCGAAGGAGAAGCCCTA | plastid_4_7 | TAAGCGCCGCGCCCTCCGAATGGTTAG | altero_2_7 | CACTTGGGCCTCTCTCTTTGCGCCGGA |
| bacilli_8 | GCTCCCGAAGGAGAAGCCCTATCTC | plastid_4_8 | TAGCCCTACCTTAAGCGCCGCCTC | altero_2_8 | CTCTGGGCCTCTCTCTTTGCGCCGAG |
| bacilli_9 | ACTCTGCTCCCGAAGGAGAAGCCCT | plastid_4_9 | CTACCTTAAGCGCCGCCCCTCCGAAT | altero_2_9 | ACTTGGGCCTCTCTCTTTAAGGGTCCGC |
| bacilli_10 | CCGAAGCCGCCTTTCAATTTCGAAC | plastid_4_10 | GCCCTACCTTAAGCGCCGCCCTCCG | altero_2_10 | CTACGACATTCTTTAAGGGGTCCGC |
| bacilli_11 | CGTCCGCCGCTAACTTCATAAGAGC | plastid_4_11 | CCCTACCTTAAGCGCCGCCCTCCGA | altero_2_11 | CCGGACTACGACATTCTTTAAGGGG |
| bacilli_12 | GTCCGCCGCTAACTTCATAAGAGCA | plastid_4_12 | CCTACCTTAAGCGCCGCCCTCCGAA | altero_2_12 | ATCTCACTTGGGCCTCTCTTTGCGC |
| bacilli_13 | CCGCCGCTAACTTCATAAGAGCAAG | plastid_4_13 | CTAGCCCTACCTTAAGCGCCGCCCT | altero_2_13 | CCCCCTCGCAAAGGCAAGTTCCCAA |
| bacilli_14 | AGCCGAAGCCGCCTTTCAATTTCGA | plastid_4_14 | ACTAGCCCTACCTTAAGCGCCGCCC | altero_2_14 | ACATTCTTTAAGGGGTCCGCTCCAC |
| bacilli_15 | CTCCGAAGGAGAAGCCCTATCTCT | plastid_4_15 | AAGCGCCGCCCTCCGAATGGTTAGG | altero_2_15 | TTGGGCCTCTCTCTTTGCGCCGAGCC |
| bacilli_16 | CAGCCGAAGCCGCCTTTCAATTTCG | plastid_4_16 | CACTAGCCCTACCTTAAGCGCCGCC | altero_2_16 | TCCCCCTCGCAAAGGCAAGTTCCCA |
| bacilli_17 | CTGTCACTCTGCTCCCGAAGGAGAA | plastid_4_17 | CGCCGCCCTCCGAATGGTTAGCGCT | altero_2_17 | CCTCGCAAAGGCAAGTTCCCAAGCA |
| bacilli_18 | GCCGAAGCCGCCTTTCAATTTCGAA | plastid_4_18 | GGGCCGCCCTCCGAATGGTTAGGCT | altero_2_18 | GGGTCCGCTCCACATCACTGTCTCG |
| bacilli_19 | CCCGTCCGCCGCTAACTTCATAAGA | plastid_4_19 | GCCGCCCTCCGAATGGTTAGGCTAA | altero_2_19 | ACGACATTCTTTAAGGGGTCCGCTC |
| bacilli_20 | CCGTCCGCCGCTAACTTCATAAGAG | plastid_4_20 | AGCGCCGCCCTCCGAATGGTTAGGC | altero_2_20 | CATTCTTTAAGGGGTCCGCTCCACA |
| bacilli_21 | CGCCCTAACTTCATAAGAGCAAGC | plastid_4_21 | ACGAGATTAGCTAGCCTTCGCAGGT | altero_2_21 | GACATTCTTTAAGGGGTCCGCTCCA |
| bacilli_22 | CCCGAAGGAGAAGCCCTATCTCTAG | plastid_4_22 | CCGCCCTCCGAATGGTTAGGCTAAC | altero_2_22 | AATCTCACTTGGGCCTCTCTTTGCG |
| bacilli_23 | CGAAGGAGAAGCCCTATCTCTAGGG | plastid_4_23 | CGCCCTCCGAATGGTTAGGCTAACG | altero_2_23 | TAAGGGGTCCGCTCCACATCACTGT |
| bacilli_24 | CCGAAGGAGAAGCCCTATCTCTAGG | plastid_4_24 | GCCCTCCGAATGGTTAGGCTAACGA | altero_2_24 | ATCCCCCTCGCAAAGGCAAGTTCCC |
| bacilli_25 | TGTCACTCTGCTCCCGAAGGAGAAG | plastid_4_25 | TCACTAGCCCTACCTTAAGCGCCGC | altero_2_25 | GGTCCGCTCCACATCACTGTCTCGC |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| crenarch_1_1 | AGCCTGTACGTTGAGCGTACAGATT | plastid_5_1 | CTCTACCCCTACCATACTCAAGCCT | colwel_1_1 | TGCGCCACTCACGGATCAAGTCCAC |
| crenarch_1_2 | CCTGTACGTTGAGCGTACAGATTTA | plastid_5_2 | GACGTCGTCCTCCAAATGGTTAGAC | colwel_1_2 | CTGCGCCACTCACGGATCAAGTCCA |
| crenarch_1_3 | GCCTGTACGTTGAGCGTACAGATTT | plastid_5_3 | CCTTAGCGTCGTCCTCCAAATGT | colwel_1_3 | GCTGCGCCACTCACGGATCAAGTCC |
| crenarch_1_4 | GAGCGTACAGATTTAACCGAAAACT | plastid_5_4 | ACCTTAGACGTCGTCCTCCAAATGG | colwel_1_4 | TAGCTGCGCCACTCACGGATCAAGT |
| crenarch_1_5 | TGAGCGTACAGATTTAACCGAAAAC | plastid_5_5 | CCTCTACCCCTACCATACTCAAGCC | colwel_1_5 | GTTAGCTGCGCCACTCACGGATCAA |
| crenarch_1_6 | CAGCCTGTACGTTGAGCGTACAGAT | plastid_5_6 | GCTAGTTCTCGCGAATTTGCGACTC | colwel_1_6 | CGTTAGCTGCGCCACTCACGGATCA |
| crenarch_1_7 | CCTTGTCACGAACCTCAAGTTCGAT | plastid_5_7 | CCTTCGGCATATGGGGATTTAGCT | colwel_1_7 | GTGCGTTAGCTGCGCCACTCACGGA |
| crenarch_1_8 | CTTGTCACGAACCTCAAGTTCGATA | plastid_5_8 | GACTAACGGTGTTGGGTATGACCAG | colwel_1_8 | TGCGTTAGCTGCGCCACTCACGGAT |
| crenarch_1_9 | TTGTCACGAACCTCAAGTTCGATAA | plastid_5_9 | ACTAAACGGTGTTGGGTATGACCAGC | colwel_1_9 | TTAGCTGCGCCACTCACGGATCAAG |
| crenarch_1_10 | CTGTACGTTGAGCGTACAGATTTAA | plastid_5_10 | CCAACAGTTATTCCCCTCCTAAGGG | colwel_1_10 | GCGGTTAGCTGCGCCACTCACGGATC |
| crenarch_1_11 | GTCACGAACCTCAAGTTCGATAACG | plastid_5_11 | CTCTCGGCATATGGGGATTTAGCTG | colwel_1_11 | AGCTGCGCCACTCACGGATCAAGTC |
| crenarch_1_12 | TTCCCTGTCACGAACCTCAAGTTC | plastid_5_12 | GCGCGAGTCATCCTTAGGCAGTGT | colwel_1_12 | GCGGTATTGCTGCCCTCTGTACCTG |
| crenarch_1_13 | TCACGAACCTCAAGTTCGATAACGC | plastid_5_13 | GCGAGTCATCCTTAGGCAGTGTA | colwel_1_13 | CGCGGTATTGCTGCCCTCTGTACCT |
| crenarch_1_14 | TGTCACGAACCTCAAGTTCGATAAC | plastid_5_14 | GCGAGTCATCCTTAGGCAGTGTAA | colwel_1_14 | GGATCAAGTCCACGAACGGCTAGTT |
| crenarch_1_15 | CTGCAGCACTGCATTGGCCACAAGC | plastid_5_15 | CACCTCTCGGCATATGGGGATTTAG | colwel_1_15 | CGGATCAAGTCCACGAACGGCTAGT |
| crenarch_1_16 | GCAGCCTGTACGTTGAGCGTACAGA | plastid_5_16 | ACCTCTCGGCATATGGGGATTTAGC | colwel_1_16 | GCGCCACTCACGGATCAAGTCCACG |
| crenarch_1_17 | CACGAACCTCAAGTTCGATAACGCC | plastid_5_17 | GCAGCCTACAATCCGAACTTGGACA | colwel_1_17 | ACGGATCAAGTCCACGAACGGCTAG |
| crenarch_1_18 | TGTACGTTGAGCGTACAGATTTAAC | plastid_5_18 | GGGCGGAGTCATCCTTAGGCAGTG | colwel_1_18 | CACGGATCAAGTCCACGAACGGCTA |
| crenarch_1_19 | CGTTGAGCGTACAGATTTAACCGAA | plastid_5_19 | CGGACAGTTCTCTCTAGAGATCCAAT | colwel_1_19 | CGCCACTCACGGATCAAGTCCACGA |
| crenarch_1_20 | GTACGTTGAGCGTACAGATTTAACC | plastid_5_20 | ATCACCGGCAGTCTCTCTAGAGATC | colwel_1_20 | GCCACTCACGGATCAAGTCCACGAA |
| crenarch_1_21 | CCTGCAGCACTGCATTGGCCACAAG | plastid_5_21 | CACCGGGCAGTCTCTCTAGAGATCCC | colwel_1_21 | TCAACGGATCAAGTCCACGAACGGCT |
| crenarch_1_22 | GGCAGCCTGTACGTTGAGCGTACAG | plastid_5_22 | ACCGGGCAGTCTCTCTAGAGATCCA | colwel_1_22 | GATCAAGTCCACGAACGGCTAGTTG |
| crenarch_1_23 | TACGTTGAGCGTACAGATTTAACCG | plastid_5_23 | CCGGCAGTCTCTCTAGAGATCCCAA | colwel_1_23 | ACTCACGGATCAAGTCCACGAACGG |
| crenarch_1_24 | ACGTTGAGCGTACAGATTTAACCGA | plastid_5_24 | TTCGCCCTCTCAGTGTCAGTAATGGC | colwel_1_24 | CACTCACGGATCAAGTCCACGAACG |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| crenarch_1_25 | CCACTCCCTAGCTCTGCAGTATTCC | plastid_5_25 | TCGCCTTCTCAGTGTCAGTAATGCC | colwel_1_25 | CTCACGGATCAAGTCCACGAACGGC |
| acido_1_1 | TGCAGCACCTCTTCTGGAGTCCCCG | margrpA_1_1 | GCTCCGGTACCGAAGGGGTCGAATC | altero_3_1 | CAACTGTTGTCCCCACGTTTTGGC |
| acido_1_2 | GCCGGCAGTCCCCAAAGTCCCCG | margrpA_1_2 | AGCTCCGGTACCGAAGGGGTCGAAT | altero_3_2 | AACTGTTGTCCCCACGTTTTGGCA |
| acido_1_3 | CCATGCAGCACCTCTTCTGGAGTCC | margrpA_1_3 | CACCCGGATTCGGGTACTACTGACTT | altero_3_3 | CCCCACGTTTTGGCATATTCCCAAG |
| acido_1_4 | CATGCAGCACCTCTTCTGGAGTCCC | margrpA_1_4 | ACCCGGATTCGGGTACTACTGACTTC | altero_3_4 | CCCACGTTTTGGCATATTCCCAAGC |
| acido_1_5 | GCGCCGGCAGTCCCCCAAAGTCCC | margrpA_1_5 | CTCCGGTACCGAAGGGGTCGAATCC | altero_3_5 | TCCCCACGTTTTGGCATATTCCCA |
| acido_1_6 | ATGCAGCACCTCTTCTGGAGTCCCC | margrpA_1_6 | CCACCCGATTCGGGTACTACTGACT | altero_3_6 | CCCCACGTTTTGGCATATTCCCAA |
| acido_1_7 | CGCCGGCAGTCCCCCAAAGTCCCC | margrpA_1_7 | GCCACCCGATTCGGGTACTACTGA | altero_3_7 | CCAACTGTTGTCCCCACGTTTTGG |
| acido_1_8 | GCAGCACCTCTTCTGGAGTCCCCGA | margrpA_1_8 | GGCCACCCGATTCGGGTACTACTGA | altero_3_8 | GTCCCCACGTTTTGGCATATTCCC |
| acido_1_9 | CAGCACCTCTTCrGGAGTCCCCGAA | margrpA_1_9 | TAGCTCCGGTACCGAAGGGGTCGAA | altero_3_9 | ACTGTTGTCCCCACGTTTTGGCAT |
| acido_1_10 | AGCACCTCTTCTGGAGTCCCCGAAG | margrpA_1_10 | TCCGGTACCGAAGGGGTCGAATCCC | altero_3_10 | TCCAACTGTTGTCCCCACGTTTTG |
| acido_1_11 | CCGGCAGTCCCCCAAAGTCCCCGG | margrpA_1_11 | GAAGGGGTCGAATCCCCGACACCA | altero_3_11 | TGTCCCCACGTTTTGGCATATTC |
| acido_1_12 | GCAGTCCCCCAAAGTCCCCGGCAT | margrpA_1_12 | AAGGGGTCGAATCCCCGACACCAA | altero_312 | GCATACCATGCTGTTAGCAACCC |
| acido_1_13 | GCACCTCTTCTGGAGTCCCCGAAGG | margrpA_1_13 | CTTCCCTTACGACAGACCTTTACGC | altero_313 | CGCATACCATGCTGTTAGCAACC |
| acido_1_14 | GCCATGCAGCACCTCTTCTGGAGTC | margrpA_1_14 | CCCGATTCGGGTACTACTGACTTCC | altero_314 | TCGCATACCATGCTGTTAGCAAC |
| acido_1_15 | ACCTCTTCTGGAGTCCCCGAAGGGA | margrpA_1_15 | ACAACTGTATCCCGAAGGATCCGCT | altero_315 | CTGTTGTCCCCACGTTTTGGCATA |
| acido_1_16 | CACCTCTTCTGGAGTCCCCGAAGGG | margrpA_1_16 | CAACTGTATCCCGAAGGATCCGCTG | altero_316 | CTTGGGCTAATCAAAACGCGCAAGG |
| acido_1_17 | CGGCAGTCCCCCAAAGTCCCCGGC | margrpA_1_17 | AACTGTATCCCGAAGGATCCGCTGC | altero_317 | TCCCACTTGGGCTAATCAAAACGCG |
| acido_1_18 | CCCGAAGGGGCCTTACCGCTCAAC | margrpA_1_18 | AACAACTGTATCCCGAAGGATCCG | altero_3_18 | TTGGGCTAATCAAAACGCGCAAGGC |
| acido_1_19 | CCTCTTCTGGAGTCCCCGAAGGGAA | margrpA_1_19 | GTTAGCTCCGGTACCGAAGGGGTCG | altero_3_19 | CCCACTTGGGCTAATCAAAACGCGC |
| acido_1_20 | GGCAGTCCCCCAAAGTCCCCGGCA | margrpA_1_20 | TTAGCTCCGGTACCGAAGGGGTCGA | altero_3_20 | TCACCGGCAGTCTCCCTATAGTTCC |
| acido_1_21 | AGCCATGCAGCACCTCTTCTGGAGT | margrpA_1_21 | GCGTTAGCTCCGGTACCGAAGGGGT | altero_3_21 | TGGGCTAATCAAAACGCGCAAGGCC |
| acido_1_22 | CAGCCATGCAGCACCTCTTCTGGAG | margrpA_1_22 | CGTTAGCTCCGGTACCGAAGGGGTC | altero_3_22 | CCACTTGGGCTAATCAAAACGCGCA |
| acido_1_23 | CCCCCGAAGGGGCCTCACCGCTCAA | margrpA_1_23 | TGCGTTAGCTCCGGTACCGAAGGGG | altero_3_23 | ATAGTTCCCGACATAACTCGCTGGC |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE SEQUENCE |
|---|---|---|---|---|---|
| acido_1_24 | ACAGCCATGCAGCACCCTTCTGGA | margrpA_1_24 | TCCCTTACGACAGACCTTTACGCTC | altero_3_24 | CCATCGCTGGTTAGCAACCCTTTGT |
| acido_1_25 | CCGAAGGGGCCTTACCGCTCAACTT | margrpA_1_25 | ACTGTATCCGAAGGATCCGCTGCA | altero_3_25 | GGGCTAATCAAAACGCGCAAGGCCC |
| acido_2_1 | GTCAACTCCCTCCACACCAAGTGTT | margrpA_2_1 | GCTGCCTTCGCATTTGACTTTCCTC | gamma_1_1 | CTAAAAGGTCAAGCCTCCCAACGG |
| acido_2_2 | GGTCAACTCCCTCCACACCAAGTGT | margrpA_2_2 | GGCTGCCTTCGCATTTGACTTTCCT | gamma_1_2 | ACTAAAAGGTCAAGCCTCCCAACGG |
| acido_2_3 | GGGTCAACTCCCTCCACACCAAGTG | margrpA_2_3 | AGGCTGCCTTCGCATTTGACTTTCC | gamma_1_3 | GAAGAGGCCCTCTTTCCCTCTTAAG |
| acido_2_4 | TCAACTCCCTCCACACCAAGTGTTC | margrpA_2_4 | ACAACTGTGCTCCGAAGAGCCCCT | gamma_1_4 | CACTAAAAGGTCAAGCCTCCCAACG |
| acido_2_5 | GGGGTCACCTCCCTCCACACCAAGT | margrpA_2_5 | TAACAACTGTGCTCCGAAGAGCCCG | gamma_1_5 | GCATGTATTAGGCCTGCCGCCAACG |
| acido_2_6 | AGGGGTCAACTCCCTCCACACCAAG | margrpA_2_6 | AACAACTGTGCTCCGAAGAGCCCGC | gamma_1_6 | GGCTCCTCCAATAGTGAGAGCTTTC |
| acido_2_7 | CAACTCCCTCCACACCAAGTGTTCA | margrpA_2_7 | GATACCATCTTCGGGTACTGCAGAC | gamma_1_7 | AAGAGGCCCTCTTTCCCTCTTTCCCTCTT |
| acido_2_8 | AAGGGGTCAACTCCCTCCACACCAA | margrpA_2_8 | TTAACAACTGTGCTCCGAAGAGCCC | gamma_1_8 | CAAGAAGAGGCCCCTCTTTCCCTCTT |
| acido_2_9 | GAAGGGGTCAACTCCCTCCACACCA | margrpA_2_9 | CAACTGTGCTCCGAAGAGCCCGCTG | gamma_1_9 | TCAAGAAGAGGCCCTCTTTCCCTCT |
| acido_2_10 | AACTCCCTCCACACCAAGTGTTCAT | margrpA_2_10 | CAGAAGGCTGCCTTCGCATTTGACT | gamma_1_10 | TAGCTGCGCCACTAAAAGGTCAAGC |
| acido_2_11 | ACTCCCTCCACACCAAGTGTTCATC | margrpA_2_11 | ACCATCTTCGGGTACTGCAGATTTC | gamma_1_11 | CAGGCTCCTCCAATAGTGAGAGCTT |
| acido_2_12 | CTCCCTCCACACCAAGTGTTCATCG | margrpA_2_12 | TTGCGGTTAGGATACCATCTTCGGG | gamma_1_12 | CTCAGGCTCAGTATCAATCCAGGGG |
| acido_2_13 | CAGTCCCCGTAGAGTTCCGCCATG | margrpA_2_13 | CTTGCGGTTAGGATACCATCTTCGG | gamma_1_13 | AAAGGTCAAGCCTCCCAACGCTAG |
| acido_2_14 | TCCCCGTAGAGTTCCCGCCATGACG | margrpA_2_14 | CCTTGCGGTTAGGATACCATCTTCG | gamma_1_14 | AGAGGCCCTCTTTCCCTCTTAAGGC |
| acido_2_15 | GTCCCCGTAGAGTTCCCGCCATGAC | margrpA_2_15 | CCATCTTCGGGTACTGCAGACTTCC | gamma_1_15 | GAGGCCCTCTTTCCCTCTTAAGGCG |
| acido_2_16 | AGTCCCCGTAGAGTTCCCGCCATGA | margrpA_2_16 | GGATACCATCTTCGGGTACTGCAGA | gamma_1_16 | AGAGGCCCTCTTTCCCTCTTAAGGC |
| acido_2_17 | GCAGTCCCCGTAGAGTTCCCGCCAT | margrpA_2_17 | ACCTGCCTTACCTTAAACAGCTCCC | gamma_1_17 | CCCCCTCTATCGTACTCTAGCCTAT |
| acido_2_18 | GGCAGTCCCCGTAGAGTTCCCGCCA | margrpA_2_18 | CCTGCCTTACCTTAAACAGCTCCCT | gamma_1_18 | CCCCTCTATCGTACTCTAGCCTATC |
| acido_2_19 | CCGGCACGGAAGGGGTCAACTCCCT | margrpA_2_19 | CCAGAAGGCTGCCTTCGCATTTGAC | gamma_1_19 | TTCAAGAAGAGGCCCCTCTTTCCCTC |
| acido_2_20 | ACGCGCTGGCAACTACGGGGTAAGG | margrpA_2_20 | TGCGGTTAGGATACCATCTTCGGGT | gamma_1_20 | AGGCCCTCTTTCCCTCTTAAGGCGT |
| acido_2_21 | GACGCGCTGGCAACTACGGGTAAG | margrpA_2_21 | CGAAGAGCCCGCTGCATTATTTGT | gamma_1_21 | GCCCTCTTTCCCTCTTAAGGCGTAT |
| acido_2_22 | TGACGCGCTGGCAACTACGGGTAAG | margrpA_2_22 | CCACCATGAATTCGCGTTCCTCTC | gamma_1_22 | CCCTCTTTCCCTCTTAAGGCGTATG |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE SEQUENCE |
|---|---|---|---|---|---|
| acido_2_23 | AGCTCCGGCACGGAAGGGGTCAACT | margrpA_2_23 | CCTCCTTGCGGTTAGGATACCATCT | gamma_1_23 | CTCTTTCCCTCTTAAGGCGTATGCG |
| acido_2_24 | GCTCCGGCACGGAAGGGGTCAACTC | margrpA_2_24 | CATCTTCGGGTACTGCAGACTTCCA | gamma_1_24 | CCTCTTTCCCTCTTAAGGCGTATGC |
| acido_2_25 | CTCCGGCACGGAAGGGGTCAACTCC | margrpA_2_25 | CGGTTAGGATACCATCTTCGGGTAC | gamma_1_25 | GGCCCTCTTTCCCTCTTAAGGCGTA |
| acido_3_1 | CTCACGGCATTCGTCCCACTCGACA | OP10_1_1 | CCGCTTGCACGGGCAGTTCCGTAAG | gamma_2_1 | TACCTGCTAGCAACCAGGGATAGGG |
| acido_3_2 | CGAGGTCCCCACGGTGTCATGCGGT | OP10_1_2 | CCCGCTTGCACGGGCAGTTCCGTAA | gamma_2_2 | CAGCATTACCTGCTAGCAACCAGGG |
| acido_3_3 | TCACCCTCACGGCATTCGTCCCACT | OP10_1_3 | CGCTTGCACGGGCAGTTCCGTAAGA | gamma_2_3 | TTACCTGCTAGCAACCAGGGATAGG |
| acido_3_4 | AGGTCCCCACGGTGTCATGCGGTAT | OP10_1_4 | TCCCGCTTGCACGGGCAGTTCCGTA | gamma_2_4 | ACCTGCTAGCAACCAGGGATAGGG |
| acido_3_5 | GGACCGAGGTCCCCACGGTGTCATG | OP10_1_5 | GGGTGCAGACAATTCAGGTGACTTG | gamma_2_5 | TCAGCATTACCTGCTAGCAACCAGG |
| acido_3_6 | CCGAGGTCCCCACGGTGTCATGCGG | OP10_1_6 | CTCCCGCTTGCACGGGCAGTTCCGT | gamma_2_6 | TCTCCCTGGAGTTCTCAGCATTACC |
| acido_3_7 | ACCCTCACGGCATTCGTCCCACTCG | OP10_1_7 | CCTCCCGCTTGCACGGGCAGTTCCG | gamma_2_7 | GTCTCCCTGGAGTTCTCAGCATTAC |
| acido_3_8 | ACCGAGGTCCCCACGGTGTCATGCG | OP10_1_8 | GCTTGCACGGGCAGTTCCGTAAGAG | gamma_2_8 | CAGTCTCCCTGGAGTTCTCAGCATT |
| acido_3_9 | CACCCTCACGGCATTCGTCCCACTC | OP10_1_9 | CGGGTGCAGACAATTCAGGTGACTT | gamma_2_9 | TCCCTGGAGTTCTCAGCATTACCTG |
| acido_3_10 | GACCGAGGTCCCCACGGTGTCATGC | OP10_1_10 | CCGTAAGAGTTCCCGACTTTACGCT | gamma_2_10 | CTCCCTGGAGTTCTCAGCATTACCT |
| acido_3_11 | CCTCACGGCATTCGTCCCACTCGAC | OP10_1_11 | GCAGACAATTCAGGTGACTTGACGG | gamma_2_11 | GCAGTCTCCCTGGAGTTCTCAGCAT |
| acido_3_12 | TTCACCCTCACGGCATTCGTCCCAC | OP10_1_12 | TCGGGTGCAGACAATTCAGGTGACT | gamma_2_12 | GGCAGTCTCCCTGGAGTTCTCAGCA |
| acido_3_13 | GAGGTCCCCACGGTGTCATGCGGTA | OP10_1_13 | CGTAAGAGTTCCCGACTTTACGCTG | gamma_2_13 | CCTGCTAGCAACCAGGGATAGGGGT |
| acido_3_14 | CCCTCACGGCATTCGTCCCACTCGA | OP10_1_14 | TTGCACGGGCAGTTCCGTAAGAGTT | gamma_2_14 | TGCTAGCAACCAGGGATAGGGGTTG |
| acido_3_15 | GGTCCCCACGGTGTCATGCGGTATT | OP10_1_15 | TCCGTAAGAGTTCCCGACTTTACGC | gamma_2_15 | CTGCTAGCAACCAGGGATAGGGGTT |
| acido_3_16 | GTCCCCACGGTGTCATGCGGTATTA | OP10_1_16 | GGCAGTTCCGTAAGAGTTCCCGACT | gamma_2_16 | TAGCAACCAGGGATAGGGGTTGCGC |
| acido_3_17 | GATTGTTCACCCTCACGGCATTCGT | OP10_1_17 | CTTGCACGGGCAGTTCCGTAAGACT | gamma_2_17 | AGCAACCAGGGATAGGGGTTGCGCT |
| acido_3_18 | AGGACCGAGGTCCCCACGGTGTCAT | OP10_1_18 | CGGGCAGTTCCGTAAGAGTTCCCGA | gamma_2_18 | CTCAGCATTACCTGCTAGCAACCAG |
| acido_3_19 | ATTGTTCACCCTCACGGCATTCGTC | OP10_1_19 | TGCACGGGCAGTTCCGTAAGAGTTC | gamma_2_19 | CTAGCAACCAGGGATAGGGGTTGCG |
| acido_3_20 | TTGTTCACCCTCACGGCATTCGTCC | OP10_1_20 | ACGGGCAGTTCCGTAAGAGTTCCCG | gamma_2_20 | GCTAGCAACCAGGGATAGGGGTTGC |
| acido_3_21 | TGTTCACCCTCACGGCATTCGTCCC | OP10_1_21 | GCACGGGCAGTTCCGTAAGAGTTCC | gamma_2_21 | GCATTACCTGCTAGCAACCAGGGAT |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| acido_3_22 | GGATTGTTCACCCTCACGGCATTCG | OP10_1_22 | CACGGGGCAGTTCCGTAAGAGTTCCC | gamma_2_22 | AGCATTACCTGCTAGCAACCAGGGA |
| acido_3_23 | CACGGCATTCGTCCCACTCGACAGG | OP10_1_23 | GCAGTTCCGTAAGAGTTCCCGACTT | gamma_2_23 | TCGCGAGTTGGCAGCCCTCTGTACG |
| acido_3_24 | TCACGGCATTCGTCCCACTCGACAG | OP10_1_24 | GGGCAGTTCCGTAAGAGTTCCCGAC | gamma_2_24 | CTCGCGAGTTGGCAGCCCTCTGTAC |
| acido_3_25 | GCTTTGATCCAAGGACCGAGGTCC | OP10_1_25 | CCCCCTTACTCCCCACACCTTAGAC | gamma_2_25 | CGCGAGTTGGCAGCCCTCTGTACGC |
| actino_1_1 | AAACCTAGATCCGTCATCCCACACG | OP3_1_1 | ATCCAAGGGTGATAGGTCCTTACGG | gamma_3_1 | TGCGACACCGAAGGGCAACCCCCC |
| actino_1_2 | CAAACCTAGATCCGTCATCCCACAC | OP3_1_2 | TCCAAGGGTGATAGGTCCTTACGGA | gamma_3_2 | CTGCGACACCGAAGGGCAACCCCCC |
| actino_1_3 | CACCACCTGTATAGGGCGCTAATGC | OP3_1_3 | CCAAGGGTGATAGGTCCTTACGGAT | gamma_3_3 | GACTAGTTCCGAGTATGTCAAGGGC |
| actino_1_4 | ACCACCTGTATAGGGCGCTAATGCA | OP3_1_4 | TGTTCTCCCCTGCTGACAGGAGTTT | gamma_3_4 | GCTGCCGACACCGAAGGGCAACCCC |
| actino_1_5 | CCACCTGTATAGGGCGCTAATGCAC | OP3_1_5 | TTGTTCTCCCCTGCTGACAGGAGTT | gamma_3_5 | AACGCGTAGCTGCGACACCGAAGG |
| actino_1_6 | CACCTGTATAGGGCGCTAATGCACA | OP3_1_6 | CTTGTTCTCCCCTGCTGACAGGAGT | gamma_3_6 | TAACGCGTAGCTGCGACACCGAAG |
| actino_1_7 | GCACCACCTGTATAGGGCGCTAATG | OP3_1_7 | GTTCTCCCCTGCTGACAGGAGTTTA | gamma_3_7 | TTACTTAACCGCCAACGCGCTTT |
| actino_1_8 | AACCTAGATCCGTCATCCCACACGC | OP3_1_8 | CATCCAAGGGTGATAGGTCCTTACG | gamma_3_8 | ACGCGTAGCTGCGACACCGAAGGG |
| actino_1_9 | TGCACCACCTGTATAGGGCGCTAAT | OP3_1_9 | TCGACAGGTTATCCCGAACCCTAGG | gamma_3_9 | TTAACGCGTAGCTGCGACACCGAA |
| actino_1_10 | AGCCCTGAACTTTCACGACCGACTT | OP3_1_10 | TTCGACAGGTTATCCCGAACCCTAG | gamma_3_10 | CGCGCTAGCTGCGACACCGAAGGGC |
| actino_1_11 | GCCCTGAACTTTCACGACCGACTTG | OP3_1_11 | TTCTCCCCTGCTGACAGGAGTTTAC | gamma_3_11 | TACTTAACCGCCAACGCGCTTTA |
| actino_1_12 | GAGCCCTGAACTTTCACGACCGACT | OP3_1_12 | CCATCCAAGGGTGATAGTCCTTAC | gamma_3_12 | AGCTGCGACACCGAAGGGCAACCCC |
| actino_1_13 | AGCGTCGATAGCGGCCCAGTGAGCT | OP3_1_13 | TGATAGGTCCTTACGGATCCCCATC | gamma_3_13 | CTTACTTAACCGCCAACGCGCTT |
| actino_1_14 | GCGTCGATAGCGGCCCAGTGAGCTG | OP3_1_14 | TCTCCCCTGCTGACAGGAGTTTACA | gamma_3_14 | ATCCGACTTACTTAACCGCCAACGC |
| actino_1_15 | CGTCGATAGCGGCCCAGTGAGCTGC | OP3_1_15 | CGGATCCCCATCTTTCCCTCATGTT | gamma_3_15 | CGACTTACTTAACCGCCAACGCGCG |
| actino_1_16 | CAGCGTCGATAGCGGCCCAGTGAGC | OP3_1_16 | TCCTTGCCGGTTAGGCAACCTACTT | gamma_3_16 | TCCGACTTACTTAACCGCCAACGCG |
| actino_1_17 | CCCTGAACTTTCACGACCGACTTGT | OP3_1_17 | AGTGCGCACCGACCGAAGTCGGTGT | gamma_3_17 | CTTAACGCGCTAGCTGCGACACCGA |
| actino_1_18 | TGAGCCCTGAACTTTCACGACCGAC | OP3_1_18 | CCAGTAATGCGCCTTCGCGACTGGT | gamma_3_18 | ACTTACTTAACCGCCAACGCGCGCT |
| actino_1_19 | ACCTAGATCCGTCATCCCACACGCG | OP3_1_19 | AGAGTGCGCACCGACCGAAGTCGGT | gamma_3_19 | GCGCTAGCTGCGACACCGAAGGGCA |
| actino_1_20 | CTCGGGCTATCCCAGTAACTAAGGT | OP3_1_20 | TCGAAAAGCACAGGACGACTATCCGGT | gamma_3_20 | CCGACTTACTTAACCGCCAACGCGC |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| actino_1_21 | CCTCGGGCTATCCCAGTAACTAAGG | OP3_1_21 | CTGTGCTTCGAAAAGCACAGGACGT | gamma_3_21 | ACTTAACCGCCAACGCGCGCTTTAC |
| actino_1_22 | TCGATAGCGGCCCAGTGAGCTGCCT | OP3_1_22 | CCTTAGAGTGCGACCGACCGAAGT | gamma_3_22 | CATCCGACTTACTTAACCGCCAACG |
| actino_1_23 | GTCGATAGCGGCCCAGTGAGCTGCC | OP3_1_23 | GCCCTCCTTGCCGGTTAGGCAACCT | gamma_3_23 | TCTTCACACGCGGCATTGCTAGA |
| actino_1_24 | CGATAGCGGCCCAGTGAGCTGCCTT | OP3_1_24 | CTCCTTGCCGGTTAGGCAACTACT | gamma_3_24 | AGAACTTAACCGCGCTAGCTGCGACA |
| actino_1_25 | TCCTCGGGCTATCCCAGTAACTAAG | OP3_1_25 | CAGTAATGCGCCTTCGCGACTGGTG | gamma_3_25 | ACTTAACGCGCTAGCTGCGACACCG |
| actino_2_1 | CCGGTTTCCCCAAGTGCAAGCACTT | OP9_1_1 | GGGCAAGATAATGTCAAGTCCCGT | gamma_4_1 | ACACCCGAAAGGCAAACCCTCCCGA |
| actino_2_2 | CAAGCACTTGGTTCGTCCCTCGACT | OP9_1_2 | GCTGGCACATAATTAGCCGGAGCTT | gamma_4_2 | GACACCCGAAAGGCAAACCCTCCGA |
| actino_2_3 | GCCGGTTTCCCCAAGTGCAAGCACT | OP9_1_3 | TGCTGGCACATAATTAGCCGGAGCT | gamma_4_3 | CACCCGAAAGGCAAACCCTCCCGACA |
| actino_2_4 | GCTTCGACACGGAAATCGTGAACTG | OP9_1_4 | CCACTTACCAGGGTAGAGATTACCAC | gamma_4_4 | ACCCGAAAGGCAAACCCTCCCGACAT |
| actino_2_5 | TTCGCCCGGTTTCCCAAGTGCAAGC | OP9_1_5 | CCCCACCATTACAGGGTAGATTACCCA | gamma_4_5 | CGACACCCGAAAGGCAAACCCTCCCG |
| actino_2_6 | CGACACGGAAATCGTGAACTGATCC | OP9_1_6 | CCCCACCATTACAGGGTAGATTACCC | gamma_4_6 | CCGAAAGGCAAACCCTCCCGACATC |
| actino_2_7 | GACACGGAAATCGTGAACTGATCCC | OP9_1_7 | CTGCTAACCTCATCATCCCGAAGGA | gamma_4_7 | GCGACACCCGAAAGGCAAACCCTCCC |
| actino_2_8 | ACACGGAAATCGTGAACTGATCCCC | OP9_1_8 | TCTGCTAACCTCATCATCCCGAAGG | gamma_4_8 | CGAAAGGCAAACCCTCCCGACATCT |
| actino_2_9 | CGCCGGTTTCCCAAGTGCAAGCAC | OP9_1_9 | CTGCTGGCACATAATTAGCCGGAGC | gamma_4_9 | GCTGCGACACCCGAAAGGCAAACCCT |
| actino_2_10 | ACGGAAATCGTGAACTGATCCCCAC | OP9_1_10 | CCACTTACCAGGGTAGATTACCACG | gamma_4_10 | AGCTGCGACACCCGAAAGGCAAACCC |
| actino_2_11 | TCGCCGGTTTCCCAAGTGCAAGCA | OP9_1_11 | GACGGGCAAGATAATGTCAAGTCCC | gamma_4_11 | TTGGCTAGCCATTGCTGGGTTTGCAG |
| actino_2_12 | CACGGAAATCGTGAACTGATCCCCA | OP9_1_12 | TCCCCCACTTACCAGGGTAGATTACC | gamma_4_12 | TGGCTAGCCATTGCTGGTTTGCAGC |
| actino_2_13 | CGGTTTCCCAAGTGCAAGCACTTG | OP9_1_13 | GCAGTCTGCCTAGAGTGCACTTGTA | gamma_4_13 | GGATTGGCTAGCCATTGCTGTGTTTG |
| actino_2_14 | AAGTGCAAGCACTTGGTTCGTCCCT | OP9_1_14 | GCTGCTGGCACATAATTAGCCGGAG | gamma_4_14 | GATTGGCTAGCCATTGCTGGTTTGC |
| actino_2_15 | GTTCGCCGGTTTCCCCAAGTGCAAG | OP9_1_15 | GGGTACCGTCAGGCTTAAGGGTTTA | gamma_4_15 | GGGATTGGCTAGCCATTGCTGTGTTT |
| actino_2_16 | CGGAAATCGTGAACTGATCCCCACA | OP9_1_16 | CACTTACAGGGTAGATTACCACGC | gamma_4_16 | GGCTAGCCATTGCTGGTTTGCAGCC |
| actino_2_17 | GCAAGCACTTGGTTCGTCCCTCGAC | OP9_1_17 | GGCAGTCTGCCTAGAGTGCACTTGT | gamma_4_17 | GAAAGGCAAACCCTCCCGACATCTA |
| actino_2_18 | CGTTCGCCGGTTTCCCCAAGTGCAA | OP9_1_18 | GGTTATCCCCCACTTACCAGGGTAGA | gamma_4_18 | CTGCGACACCCGAAAGGCAAACCCTC |
| actino_2_19 | AAGCACTTGGTTCGTCCCTCGACTT | OP9_1_19 | GAGGGTATCCCCCACTTACAGGGT | gamma_4_19 | TGCCGACACCCGAAAGGCAAACCCTCC |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| actino_2_20 | GGTTTCCCCAAGTGCAAGCACTTGG | OP9_1_20 | GGGTTATCCCCACTTACAGGGTAG | gamma_4_20 | AGGGATTGGCTAGCCATTGCTGGTT |
| actino_2_21 | AGTGCAAGCACTTGGTTCGTCCCTC | OP9_1_21 | GTCAGAGATAGACCAGAAAGCCGCC | gamma_4_21 | AAGGGATTGGCTAGCCATTGCTGGT |
| actino_2_22 | CAAGTGCAAGCACTTGGTTCGTCCC | OP9_1_22 | GGGGTACCGTCAGGCTTAAGGGTTT | gamma_4_22 | TAAGGGATTGGCTAGCCATTGCTGG |
| actino_2_23 | CCGTTCGCCCGGTTTCCCCAAGTGCA | OP9_1_23 | AGGGTTATCCCCACTTACAGGGTA | gamma_4_23 | TAGCTGCGACACCGAAAGGCAAACC |
| actino_2_24 | CCGTAGTTATCCCGGTGTACAGGGC | OP9_1_24 | CGGCAGTCTGCCTAGAGTGCACTTG | gamma_4_24 | TTAGCTGCGACACCGAAAGGCAAAC |
| actino_2_25 | CCTCAAGCCTTGCAGTATCCGACTGC | OP9_1_25 | CTCCGATTATCTGCGGCAGTCTGC | gamma_4_25 | GTTAGCTGCGACACCGAAAGGCAAA |
| bacter_1_1 | GTTTCCGCGACTGTCATTCCACGTT | plancto_1_1 | TGCAACACCTGTGCAGGTCACACCC | gamma_5_1 | CCACTAAGGGACAAATTCCCCCAAC |
| bacter_1_2 | TTCCCGCGACTGTCATTCCACGTTCG | plancto_1_2 | GCAACACCTGTGCAGGTCACACCCG | gamma_5_2 | CGCCACTAAGGGACAAATTCCCCCA |
| bacter_1_3 | ACGTTTCCGCGACTGTCATTCCACG | plancto_1_3 | ATGCAACACCTGTGCAGGTCACACC | gamma_5_3 | GCCACTAAGGGACAAATTCCCCCAA |
| bacter_1_4 | TTTCCGCGACTGTCATTCCACGTTC | plancto_1_4 | AACACCTGTGCAGGTCACACCCGAA | gamma_5_4 | CACTAAGGGACAAATTCCCCCAACG |
| bacter_1_5 | CACGTTTCCGCGACTGTCATTCCAC | plancto_1_5 | CAACACCTGTGCAGGTCACACCCGA | gamma_5_5 | ACTAAGGGACAAATTCCCCCAACGG |
| bacter_1_6 | TCACGTTTCCGCGACTGTCATTCCA | plancto_1_6 | TGTGCAGGTCACACCCGAAGGTAAT | gamma_5_6 | CTAAGGGACAAATTCCCCCAACGGC |
| bacter_1_7 | CGTTTCCGCGACTGTCATTCCACGT | plancto_1_7 | GTGCAGGTCACACCCGAAGGTAATC | gamma_5_7 | GCGCCACTAAGGGACAAATTCCCCC |
| bacter_1_8 | TGTCATTCCACGTTCGAGCCCAGGT | plancto_1_8 | TGCAGGTCACACCCGAAGGTAATCA | gamma_5_8 | GGTACCGTCAAGACGGCATGGATT |
| bacter_1_9 | CTGTCATTCCACGTTCGAGCCCAGG | plancto_1_9 | CTGTGCAGGTCACACCCGAAGGTAA | gamma_5_9 | AGGTACCGTCAAGACGCGCAGTTAT |
| bacter_1_10 | CCGCGACTGTCATTCCACGTTCGAG | plancto_1_10 | CCTGTGCAGGTCACACCCGAAGTA | gamma_5_10 | TAGGTACCGTCAAGACGCGCAGTTA |
| bacter_1_11 | ACTGTCATTCCACGTTCGAGCCCAG | plancto_1_11 | ACACCTGTGCAGGTCACACCCGAAG | gamma_5_11 | TGCGCCACTAAGGGACAAATTCCCC |
| bacter_1_12 | CGCGACTGTCATTCCACGTTCGAGC | plancto_1_12 | ACAGAGTTAGCCAGTGCTTCCTCTC | gamma_5_12 | TAAGGGACAAATTCCCCCAACGGCT |
| bacter_1_13 | GCGACTGTCATTCCACGTTCGAGCC | plancto_1_13 | ACCTGTGCAGGTCACACCCGAAGGT | gamma_5_13 | CTGTAGGTACCGTCAAGACGGCGCAG |
| bacter_1_14 | CGACTGTCATTCCACGTTCGAGCCC | plancto_1_14 | CATGCAACACCTGTGCAGGTCACAC | gamma_5_14 | GTAGGTACCGTCAAGACGCGCAGTT |
| bacter_1_15 | TCCGCGACTGTCATTCCACGTTCGA | plancto_1_15 | CACCTGTGCAGGTCACACCCGAAGG | gamma_5_15 | CTGCGCCACTAAGGGACAAATTCCC |
| bacter_1_16 | GACTGTCATTCCACGTTCGAGCCCA | plancto_1_16 | CACAGAGTTAGCCAGTGCTTCCTCT | gamma_5_16 | TGTAGGTACCGTCAAGACGCGCAGT |
| bacter_1_17 | ATCACGTTTCCGCGACTGTCATTCC | plancto_1_17 | CAGAGTTAGCCAGTGCTTCCTCTCG | gamma_5_17 | TCTGTAGGTACCGTCAAGACGCGCA |
| bacter_1_18 | GTCATTCCACGTTCGAGCCCAGGTA | plancto_1_18 | AGCCAGTGCTTCCTCTCGAGCTTAC | gamma_5_18 | GTCCGCCACTCGACGCCTGAAGAGC |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| bacter_1_19 | ACGGTACCATCAGCACCGATACACG | plancto_1_19 | GCACAGAGTTAGCCAGTGCTTCCTC | gamma_5_19 | GCCACTCGACGCCTGAAGAGCAAGC |
| bacter_1_20 | GTACCATCAGCACCGATACACGACC | plancto_1_20 | GGCCTAGCCCCTGCATGTCAAGCCT | gamma_5_20 | GCTGCGCCACTAAGGGACAAATTCC |
| bacter_1_21 | GGTACCATCAGCACCGATACACGAC | plancto_1_21 | GCAGGTCACACCCGAAGGTAATCAG | gamma_5_21 | CACTCGGTTCCCGAAGGCACCAAAC |
| bacter_1_22 | CGGTACCATCAGCACCGATACACGA | plancto_1_22 | ACCGGCTAGCCCCTGCATGTCAAG | gamma_5_22 | CTTCTGTAGTACCGTCAAGACGCG |
| bacter_1_23 | GATCACGTTTCCGCGACTGTCATTC | plancto_1_23 | CAGGTCACACCCGAAGGTAATCAGC | gamma_5_23 | CACTCGACGCCTGAAGAGCAAGCTC |
| bacter_1_24 | TACGGTACCATCAGCACCGATACAC | plancto_1_24 | CCGGCCTAGCCCCTGCATGTCAAGC | gamma_5_24 | CGCCACTCGACGCCTGAAGAGCAAG |
| bacter_1_25 | CACCGATACACGACCGGTGTTTTT | plancto_1_25 | CGGCCTAGCCCCTGCATGTCAAGCC | gamma_5_25 | GGACAAATTCCCCACGCGGCTAGTT |
| bacter_2_1 | GGATTTCTCCGGGCTACCTTCCGGT | plancto_2_1 | TCTCCGAAGAGCACTCTCCCCTTTC | gamma_6_1 | AGCTGCGCCACCAACCTCTTGAATG |
| bacter_2_2 | CTCCGGGCTACCTTCCGGTAAAGGG | plancto_2_2 | TACGACCGAGAAACTGTGGGAGGTC | gamma_6_2 | CCAACCTCTTGAATGAGGCCGACGG |
| bacter_2_3 | CGGGATTTCTCCGGGCTACCTTCCGG | plancto_2_3 | ACCGGAGAAACTGTGGGAGGTCCCT | gamma_6_3 | TGCGCCACCAACCTCTTGAATGAGG |
| bacter_2_4 | TCTCCGGGCTACCTTCCGGTAAAGG | plancto_2_4 | CGACCGAGAAACTGTGGGAGGTCCC | gamma_6_4 | GCCACCAACCTCTTGAATGAGGCCG |
| bacter_2_5 | TTCTCCGGGCTACCTTCCGGTAAAG | plancto_2_5 | CTCCGAAGAGCACTCTCTCCCTTTCA | gamma_6_5 | ACCAACCTCTTGAATGAGGCCGACG |
| bacter_2_6 | TTTTCTCCGGGCTACCTTCCGGTAA | plancto_2_6 | GCCCCGACCTTCCTCTGAGGTTTGGT | gamma_6_6 | CTGCCCACCAACCTCTTGAATGAG |
| bacter_2_7 | GATTTCTCCGGGCTACCTTCCGGTA | plancto_2_7 | AAACTGTGGGAGGTCCCTCGATCCA | gamma_6_7 | CAACCTCTTGAATGAGGCCGACGGC |
| bacter_2_8 | ATTTCTCCGGGCTACCTTCCGGTAA | plancto_2_8 | TCCGAAGAGCACTCTCCCCTTTCAG | gamma_6_8 | GCGCCACCAACCTCTTGAATGAGGC |
| bacter_2_9 | CCGGATTTCTCCGGGCTACCTTCCG | plancto_2_9 | GACCGAGAAACTGTGGGAGGTCCCT | gamma_6_9 | CGCCACCAACCTCTTGAATGAGGCC |
| bacter_2_10 | TCCGGATTTCTCCGGGCTACCTTCC | plancto_2_10 | ACGACCGAGAAACTGTGGGAGGTCC | gamma_6_10 | CACCAACCTCTTGAATGAGGCCGAC |
| bacter_2_11 | TCCGGGCTACCTTCCGGTAAAGGGT | plancto_2_11 | GAAACTGTGGGAGGTCCCTCGATCC | gamma_6_11 | GCTGCGCCACCAACCTCTTGAATGA |
| bacter_2_12 | ATCCGGATTTCTCCGGGCTACCTTC | plancto_2_12 | CTCTCCGAAGAGCACTCTCCCCTTT | gamma_6_12 | CCAACCTCTTGAATGAGGCCGA |
| bacter_2_13 | CTTTATGGATTAGTCCCCGTCGCT | plancto_2_13 | GCCTGGAGGTAGGTATCACCTGTT | gamma_6_13 | TAGCTGCGCCACCAACCTCTTGAAT |
| bacter_2_14 | ACTTTATGGATTAGTCCCCGTCGC | plancto_2_14 | TCCCGACGCTATTCCCAGCCTGGAG | gamma_6_14 | AACCTCTTGAATGAGGCCGACGGCT |
| bacter_2_15 | CCGGGCTACCTTCCGGTAAAGGGTA | plancto_2_15 | TTGGGCATTACCGCCAGTTTCCCGA | gamma_6_15 | AGAGGTCCACTTTGCCCCGAAGGGC |
| bacter_2_16 | AATCCGGATTTCTCCGGGCTACCTT | plancto_2_16 | CCGAGAAACTGTGGGAGGTCCCTCG | gamma_6_16 | GAGGTCCACTTTGCCCCGAAGGGCG |
| bacter_2_17 | GCTACCTTCCGGTAAAGGGTAGGTT | plancto_2_17 | TGAGCAGACCCATCTCCAGGCCGCC | gamma_6_17 | TCTTCAGGTAACGTCAATACGCGCG |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| bacter_2_18 | GGCTACCTTCCGGTAAAGGGTAGGT | plancto_2_18 | AACTGTGGGAGTCCCTCGATCCAG | gamma_6_18 | TTAGCTGCGCCACCAACCTCTTGAA |
| bacter_2_19 | GGGCTACCTTCCGGTAAAGGGTAGG | plancto_2_19 | CCCGACCTTCCTCTGAGGTTTGGTC | gamma_6_19 | CAGAGGTCCACTTTGCCCCGAAGGG |
| bacter_2_20 | TAATCGGATTTCTCCGGGCTACCT | plancto_2_20 | TGGGCATTACCGCCAGTTTCCCGAC | gamma_6_20 | AGGTCCACTTTGCCCCGAAGGGCGT |
| bacter_2_21 | CTACCTTCCGGTAAAGGGTAGGTTG | plancto_2_21 | CGAGAAACTGTGGGAGTCCCTCGA | gamma_6_21 | ACCTCTTGAATGAGGCCGACGGCTA |
| bacter_2_22 | CGGGCTACCTTCCGGTAAAGGGTAG | plancto_2_22 | GAGAAACTGTGGGAGGTCCCTGAT | gamma_6_22 | CGCGCGGGTATTAACCGCACGCTTT |
| bacter_2_23 | TTAATCCGGATTTCTCCGGGCTACC | plancto_2_23 | CAGCCTGAGGTAGGTATCTACCTG | gamma_6_23 | CTTCAGTAACGTCAATACGCGCGG |
| bacter_2_24 | TTTATGGATTAGCTCCCCGTCGCTG | plancto_2_24 | AGCCCGACCTTCCTCTGAGGTTTGG | gamma_6_24 | TCAGAGGTCCACTTTGCCCCGAAGG |
| bacter_2_25 | TACCTTCCGGTAAAGGGTAGGTTGC | plancto_2_25 | AATAGTGAGCAGACCCATCTCCAGG | gamma_6_25 | ACGCGCGGGTATTAACCGCACGCTT |
| bacter_3_1 | GGCTCCTCGCCGTATCATCGAAATT | plancto_3_1 | CGCAGTGCCTCAGTTAAGCTCAGGC | gamma_7_1 | GTCCTCCGTAGTTAGACTAGCCACT |
| bacter_3_2 | CAACCTTGCCAATCACTCCCCAGGT | plancto_3_2 | GCAGTGCCTCAGTTAAGCTCAGGCA | gamma_7_2 | CGTCCTCCGTAGTTAGACTAGCCAC |
| bacter_3_3 | CTTGCCAATCACTCCCCAGGTGGAT | plancto_3_3 | CAACTCTGAGGGAGTACCCTTCAGAG | gamma_7_3 | ACCGTCCTCCGTAGTTAGACTAGCC |
| bacter_3_4 | CAGGTAAGGCTCCTCGCCGTATCAT | plancto_3_4 | GTCAACTCTGAGGGAGTACCCTCAG | gamma_7_4 | CCGTCCTCCGTAGTTAGACTAGCCA |
| bacter_3_5 | AGGCTCCTCGCCGTATCATCGAAAT | plancto_3_5 | TATGTTTTTCCTACGCCGTTCGCGC | gamma_7_5 | GACCGTCCTCCGTAGTTAGACTAGC |
| bacter_3_6 | AACCTTGCCAATCACTCCCCAGGTG | plancto_3_6 | GCAGAAGGAGAACCTCCTCCCGC | gamma_7_6 | TGACCGTCCTCCGTAGTTAGACTAG |
| bacter_3_7 | ACCTTGCCAATCACTCCCCAGGTGG | plancto_3_7 | AACTCTGAGGGAGTACCCTCAGAGA | gamma_7_7 | CTGCAGGTAACGTCAAGTACTCACC |
| bacter_3_8 | TCAACCTTGCCAATCACTCCCCAGG | plancto_3_8 | TCAACTCTGAGGGAGTACCCTCAGA | gamma_7_8 | TATTAGGGGTAAGCCTTCCTCCCTG |
| bacter_3_9 | GGTAAGGCTCCTCGCCGTATCATCG | plancto_3_9 | CTATGTTTTTCCTACGCCGTTGGCCG | gamma_7_9 | TGCAGTAACGTCAAGTACTCACCC |
| bacter_3_10 | TCCGCTACCCCAACTATACTCTAG | plancto_3_10 | TCCTATGTTTTTCCTACGCCGTTCGC | gamma_7_10 | GCAGGTAACGTCAAGTACTCACCCG |
| bacter_3_11 | TTCAACCTTGCCAATCACTCCCCAG | plancto_3_11 | CCTATGTTTTTCCTACGCCGTTCGCC | gamma_7_11 | TTCCCCGGGTTGTCCCCACTCATG |
| bacter_3_12 | CCCAGGTAAGGCTCCTCTCGCCGTATC | plancto_3_12 | ACTCTGAGGGAGTACCCTCAGAGAT | gamma_7_12 | TCCCCGGGTTGTCCCCACTCATGG |
| bacter_3_13 | AGGTAAGGCTCCTCGCCGTATCATC | plancto_3_13 | ACGCAGTGCCTCAGTTAAGCTCAGG | gamma_7_13 | CCCCGGGTTGTCCCCACTCATGGG |
| bacter_3_14 | CCAATCACTCCCCAGGTGGATTACC | plancto_3_14 | TGTCAACTCTGAGGGAGTACCCTCA | gamma_7_14 | TTTCCCCGGGTTGTCCCCACTCAT |
| bacter_3_15 | CCTTGCCAATCACTCCCCAGGTGGA | plancto_3_15 | ATGTTTTCCTACGCCGTTAAGCTCAG | gamma_7_15 | CCCGGGTTGTCCCCACTCATGGGT |
| bacter_3_16 | GTAAGGCTCCTCGCCGTATCATCGA | plancto_3_16 | AACGCAGTGCCTCAGTTAAGCTCAG | gamma_7_16 | CCGGGTTGTCCCCACTCATGGGTA |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| bacter_3_17 | CCGCCTACCCCAACTATACTCTAGA | plancto_3_17 | CAGTGCCTCAGTTAAGCTCAGGCAT | gamma_7_17 | CTCACCCGTATTAGGGGTAAGCCTT |
| bacter_3_18 | CCAGTAAGGCTCCTCGCCGTATCA | plancto_3_18 | CTGTCAACTCTGAGGGAGTACCCTC | gamma_7_18 | ACCCGTATTAGGGGTAAGCCTTCCT |
| bacter_3_19 | AAGGCTCCTCGCCGTATCATCGAAA | plancto_3_19 | CTCTGAGGGAGTACCCTCAGAGATT | gamma_7_19 | ACTCACCCGTATTAGGGGTAAGCCT |
| bacter_3_20 | GCCAATCACTCCCCAGGTGGATTAC | plancto_3_20 | TCTGTCAACTCTGAGGGAGTACCCT | gamma_7_20 | GTCAAGTACTCACCCGTATTAGGGG |
| bacter_3_21 | TAAGGCTCCTCGCCGTATCATCGAA | plancto_3_21 | GGAGTACCCTCAGAGATTTCATCCC | gamma_7_21 | TCACCCGTATTAGGGGTAAGCCTTC |
| bacter_3_22 | GCCCAGGTAAGGCTCCTCGCCGTAT | plancto_3_22 | CAAACGCAGTGCCTCAGTTAAGCTC | gamma_7_22 | CCCGTATTAGGGGTAAGCCTTCCTC |
| bacter_3_23 | CATTCCGCCTACCCCAACTATACTC | plancto_3_23 | CTCTGTCAACTCTGAGGGAGTACCC | gamma_7_23 | GTACTCACCCGTATTAGGGGTAAGC |
| bacter_3_24 | CAATCACTCCCCAGGTGGATTACCT | plancto_3_24 | ACAGCAGAAGAGAGAAACCTCCTCC | gamma_7_24 | CACCCGTATTAGGGGTAAGCCTTCC |
| bacter_3_25 | CCGCCGGAACTTTGATCATCAAGAG | plancto_3_25 | CTGAGGGAGTACCCTCAGAGATTTC | gamma_7_25 | TACTCACCCGTATTAGGGGTAAGCC |
| flavo_1_1 | CTCAGACACCAAGGTCCAAACAGCT | plancto_4_1 | ACTACCTAATATCGCATCGGCCGCT | gamma_8_1 | CGCGAGCTCATCATCAGCACAAGG |
| flavo_1_2 | CAGAGACACCAAGGTCCAAACAGTC | plancto_4_2 | CAACTACCTAATATCGCATCGGCCG | gamma_8_2 | TCATCATCAGCACAAGGTCCGAAG |
| flavo_1_3 | CACTCAGACACCAAGGTCCAAACAG | plancto_4_3 | AACTACCTAATATCGCATCGGCCGC | gamma_8_3 | CTCATCATCAGCACAAGGTCCGAA |
| flavo_1_4 | GCTTAGCCACTCAGACACCAAGGTC | plancto_4_4 | CCAACTACCTAATATCGCATCGCC | gamma_8_4 | GCTCATCATCAGCACACAAGGTCCGA |
| flavo_1_5 | ACTCAGACACCAAGGTCCAAACAGC | plancto_4_5 | ACGTTCCGATGTATTCCTACCCCGT | gamma_8_5 | ACGGAGCTCATCATCAGCACACAAG |
| flavo_1_6 | CTTAGCCACTCAGACACCAAGGTCC | plancto_4_6 | TACGTTCCGATGTATTCCTACCCCG | gamma_8_6 | CATCATCAGCACAAGGTCCGAAGA |
| flavo_1_7 | TACCGTCAAGCTTGTACACGTACC | plancto_4_7 | GTACGTTCCGATGTATTCCTACCCC | gamma_8_7 | GACGCGAGCTCATCATCAGCACAA |
| flavo_1_8 | GTACCGTCAAGCTTGTACACGTAC | plancto_4_8 | CTACCTAATATCGCATCGGCCGCTC | gamma_8_8 | GCGAGCTCATCATCAGCACAAGGT |
| flavo_1_9 | GCCACTCAGACACCAAGGTCCAAAC | plancto_4_9 | CGTTCCGATGTATTCCTACCCCGTT | gamma_8_9 | TCCATCAGCACAAGGTCCGAGATC |
| flavo_1_10 | TTAGCCACTCAGACACCAAGGTCCA | plancto_4_10 | GTTTCCACCACTAATCCGTGCATG | gamma_8_10 | CGACCGGAGCTCATCATCAGCACA |
| flavo_1_11 | ACCGTCAAGCTTGGTACACGTACCA | plancto_4_11 | TTCCACCCACTAATCCGTGCATGTC | gamma_8_11 | CATCAGCACAAGGTCCGAAGATCC |
| flavo_1_12 | CCACTCAGACACCAAGGTCCAAACA | plancto_4_12 | TCCACCCACTAATCCGTGCATGTCA | gamma_8_12 | CCCTCTAATGGGCAGATTCTCACGT |
| flavo_1_13 | AGCCACTCAGACACCAAGGTCCAAA | plancto_4_13 | CCACCCACTAATCCGTGCATGTCAA | gamma_8_13 | CCGACCGGAGCTCATCATCAGCAC |
| flavo_1_14 | TAGCCACTCAGACACCAAGGTCCAA | plancto_4_14 | GGCAGTAAACCTTTGGTCTCTGAC | gamma_8_14 | CCCCTCTAATGGGCAGATTCTCACG |
| flavo_1_15 | CCGTCAAGCTTGGTACACGTACCAA | plancto_4_15 | GGTACGTTCCGATGTATTCCTACCC | gamma_8_15 | CCCCCTCTAATGGGCAGATTCTCAC |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| flavo_1_16 | CGCTTAGCCACTCAGACACCAAGGT | plancto_4_16 | TGCGAGCGTCATGAATGTTTCCACC | gamma_8_16 | CGAGCTCATCCATCAGCACAAGGTC |
| flavo_1_17 | TCGCTTAGCCACTCAGACACCAAGG | plancto_4_17 | GCGAGCGTCATGAATGTTTCCACCC | gamma_8_17 | CCATCAGCACAAGGTCCGAAGATCC |
| flavo_1_18 | CGTCAAGCTTGGTACACGTACCAAG | plancto_4_18 | GAGCGTCATGAATGTTTCCACCCAC | gamma_8_18 | CCTCTAATGGGCAGATTCTCACGTG |
| flavo_1_19 | CAGTAGTAACCATCGTTTACCGGC | plancto_4_19 | CGAGCGTCATGAATGTTTCCACCCA | gamma_8_19 | CCCAGGTTATCCCCTCTAATGGGC |
| flavo_1_20 | GCCATAGTAGAGACTATGGGGGAT | plancto_4_20 | CAGTTATGCCCCAGTGAATCGCCTT | gamma_8_20 | TCCGACGCGAGCTCATCCATCAGCA |
| flavo_1_21 | TGCCATAGTAGAGACTATGGGGGA | plancto_4_21 | TCAGTTATGCCCCAGTGAATCGCCT | gamma_8_21 | GAGCTCATCCATCAGCACAAGGTCC |
| flavo_1_22 | ATGCCATAGCTAGAGACTATGGGGG | plancto_4_22 | AGTTATGCCCCAGTGAATCGCCTTC | gamma_8_22 | TTCCCCAGGTTATCCCCTCTAATG |
| flavo_1_23 | TTCGCTTAGCCACTCAGACACCAAG | plancto_4_23 | GTCAGTTATGCCCCAGTGAATCGCC | gamma_8_23 | TCCCCAGGTTATCCCCTCTAATGG |
| flavo_1_24 | AGCTAGTAACCATCGTTTACCGGCG | plancto_4_24 | GTTATGCCCCAGTGAATCGCCTTCG | gamma_8_24 | CCCCAGGTTATCCCCTCTAATGGG |
| flavo_1_25 | GTCAAGCTTGGTACACGTACCAAGG | plancto_4_25 | CTCCACTGGATGTTCCATTCACCTC | gamma_8_25 | ATCCCCCTCTAATGGGCAGATTCTC |
| flavo_2_1 | TACAGTACCGTCAGAGCTCTACACG | alpha_1_1 | CCGGCCCCTTGCGGGAAGAAAGCCA | gamma_9_1 | CCTGTCCATCGGTTCCCGAAGGCAC |
| flavo_2_2 | TCTTACAGTACCGTCAGAGCTCTAC | alpha_1_2 | CACCTGTGCACCGGCCCCTTGCGGG | gamma_9_2 | CTGTCCATCGGTTCCCGAAGGCACC |
| flavo_2_3 | TTACAGTACCGTCAGAGCTCTACA | alpha_1_3 | GCACCTGTGCACCGGCCCCTTGCGG | gamma_9_3 | TGTCCATCGGTTCCCGAAGGCACCA |
| flavo_2_4 | GCATACTCATCTCTTACCGCCGAAG | alpha_1_4 | CTGTGCACCGGCCCCTTGCGGGAAG | gamma_9_4 | CAGCACCTGTCATCGGTTCCCGAA |
| flavo_2_5 | CATACTCATCTCTTACCGCCGAAGC | alpha_1_5 | ACCTGTGCACCGGCCCCTTGCGGGA | gamma_9_5 | AGCACCTGTCCATCGGTTCCCGAAG |
| flavo_2_6 | ACAGTACCGTCAGAGCTCTACACGT | alpha_1_6 | CCTGTGCACCGGCCCCTTGCGGGAA | gamma_9_6 | ACCTGTCCATCGGTTCCCGAAGGCA |
| flavo_2_7 | CAGTACCGTCAGAGCTCTACACGTA | alpha_1_7 | AGCACCTGTGCACCGGCCCCTTGCG | gamma_9_7 | GTCCATCGGTTCCCGAAGGCACCAA |
| flavo_2_8 | CTTACAGTACCGTCAGAGCTCTACA | alpha_1_8 | CGGCCCCTTGCGGGAAGAAAGCCAT | gamma_9_8 | CACCTGTCCATCGGTTCCCGAAGGC |
| flavo_2_9 | TACTTCATCTCTTACCGCCGAAGCTT | alpha_1_9 | GCACCGGCCCCTTGCGGGAAGAAAG | gamma_9_9 | CCTCCCTCTCTCGCACTCTAGCCTT |
| flavo_2_10 | ATATCATCTCTTACCGCCGAAGCT | alpha_1_10 | CACCGGCCCCTTGCGGGAAGAAAGC | gamma_9_10 | GCAACCTGTCCATCGGTTCCCGAAGG |
| flavo_2_11 | CTCATCTCTTACCGCCGAAGCTTTA | alpha_1_11 | ACCGGCCCCTTGCGGGAAGAAAGCC | gamma_9_11 | GCAGACCTGTCCATCGGTTCCCGA |
| flavo_2_12 | CGCCCAGTGGCTGCTCTCTGTCTAT | alpha_1_12 | TGTGCACCGGCCCCTTGCGGGAAGA | gamma_9_12 | ACCTCCCTCTCTCGCACTCTAGCCT |
| flavo_2_13 | CCAGTGGCTGCTCTCTGTCTATACC | alpha_1_13 | GTGCACCGGCCCCTTGCGGGAAGAA | gamma_9_13 | CTCCCTCTCTCGCACTCTAGCCTTC |
| flavo_2_14 | CCCAGTGGCTGCTCTCTGTCTATAC | alpha_1_14 | TGCACCGGCCCCTTGCGGGAAGAAA | gamma_9_14 | TCTCTGCACTCTAGCCTTCAGTA |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| flavo_2_15 | TCGCCCAGTGGCTGCTCTGTCTA | alpha_1_15 | CAGCACCTGTGCACCGGCCCCTTGC | gamma_9_15 | TCGCACTCTAGCCTTCCAGTATCGG |
| flavo_2_16 | GCCCAGTGGCTGCTCTCTGTCTATA | alpha_1_16 | TTGCGGGAAGAAAGCCATCTCTGGC | gamma_9_16 | CTCGCACTCTAGCCTTCCAGTATCG |
| flavo_2_17 | GACTTCGATCCGAACTGTGATATAG | alpha_1_17 | GGCCCCTTGCGGGAAGAAAGCCATC | gamma_9_17 | TACCTCCCTCTCTCGCACTCTAGCC |
| flavo_2_18 | AGAACGCATACTCATCTCTTACCGC | alpha_1_18 | CCTTGCGGGAAGAAAGCCATCTCTG | gamma_9_18 | CTCTCGCACTCTAGCCTTCCAGTAT |
| flavo_2_19 | GAACGCATATCATCTCTTACCGCC | alpha_1_19 | GCAGCACCTGTGCACCGGCCCCTTG | gamma_9_19 | CCCTCTCTCGCACTCTAGCCTTCCA |
| flavo_2_20 | CACGTAGAGCGGTTTCTTCCTGTAT | alpha_1_20 | TGCGGGAAGAAAGCCATCTCTGGCG | gamma_9_20 | TGCAGCACCTGTCCATCGGTTCCCG |
| flavo_2_21 | GTCCTGTCACACTACATTTAAGCCC | alpha_1_21 | AAAGCCATCTCTGGCGATCATACCG | gamma_9_21 | ACTCCGTGGTAATCGCCCTCCCGAA |
| flavo_2_22 | ACTCATCTCTTACCGCCGAAGCTTT | alpha_1_22 | GCCCCTTGCGGGAAGAAAGCCATCT | gamma_9_22 | TCCATCGGTTCCCGAAGGCACCAAT |
| flavo_2_23 | CCCTATCTATCGTAGCCATGGTGT | alpha_1_23 | AACAGCAAGCTGCCCAACGGCTAGC | gamma_9_23 | TCACTCCGTGTAATCGCCCTCCCG |
| flavo_2_24 | CCCTATCTATCGTAGCCATGGTGTG | alpha_1_24 | CATGCAGCACCTGTGCACCGGCCCC | gamma_9_24 | TCCCTCTCTCGCACTCTAGCCTTCC |
| flavo_2_25 | CCTATCTATCGTAGCCATGTGTGC | alpha_1_25 | GCAAGCTGCCCAACGGCTAGCATCC | gamma_9_25 | CCTCTCTCGCACTCTAGCCTTCCAG |
| flavo_3_1 | CTGTCACCTAACATTTAAGCCCTGG | alpha_2_1 | GTGACCCAGAAAGTTGCCTTCGCAT | gamma_10_1 | CGCAGGCACATCCGATAGCGAGAGC |
| flavo_3_2 | CCGTCAAGCTTTCTCACGAGAAAGT | alpha_2_2 | GTATTCACCGCGACGCCTGATTCG | gamma_10_2 | ACGCAGGCACATCCGATAGCGAGAG |
| flavo_3_3 | ACCGTCAAGCTTTCTCACGAGAAAG | alpha_2_3 | CGTATTCACCGCGACGGCTGATTC | gamma_10_3 | GCGGCTTCGCGCGCCCTCTGTACTTG |
| flavo_3_4 | CTCTGACTTATTTGTCCACCTACGG | alpha_2_4 | TATTCACCGCGACGCGTGATTCGC | gamma_10_4 | CGGCTTCGCGCGCCCTCTGTACTTGC |
| flavo_3_5 | CCTCTGACTTATTTGTCCACCTACG | alpha_2_5 | ACGTATTCACCGCGACGCGCTGATT | gamma_10_5 | GGCTTCGCGGCCCTCTGTACTTGC |
| flavo_3_6 | GTACCGTCAAGCTTTCTCACGAGAA | alpha_2_6 | GGAACGTATTCACCGCGACGCGCTG | gamma_10_6 | CGCGGCTTCGCGCCCTCTGTACTT |
| flavo_3_7 | GAGGCAGATTGTATACGCGATACTC | alpha_2_7 | CCGGAACGTATTCACCGCGACGCG | gamma_10_7 | GCTTCGCGGCCCTCTGTACTTGCCA |
| flavo_3_8 | TCTATCGTAGCCTAGGTGTGCCGTT | alpha_2_8 | CGGGAACGTATTCACCGCGACGACGC | gamma_10_8 | CACTACTGGGTAGTTTCCTACGCGT |
| flavo_3_9 | CCCCTATCGTAGCCTAGGTGTGT | alpha_2_9 | GGGAACGTATTCACCGCGACGACGCT | gamma_10_9 | CCAACTACTGGGTAGTTTCCTACGCG |
| flavo_3_10 | ATCTATCGTAGCCTAGGTGTGCCGT | alpha_2_10 | AACGTATTCACCGCGACGCGCTGAT | gamma_10_10 | CCCCACTACTGGGTAGTTCCTACG |
| flavo_3_11 | CCCTATCTATCGTAGCCTAGGTGTG | alpha_2_11 | GAACGTATTCACCGCGACGCGCTGA | gamma_10_11 | CCCACTACTGGGTAGTTTCCTACGC |
| flavo_3_12 | TATCTATCGTAGCCTAGGTGTGCCG | alpha_2_12 | CCCGGGAACGTATTCACCGCGACGC | gamma_10_12 | CCCCCACTACTGGGTAGTTCCTAC |
| flavo_3_13 | CCTATCTATCGTAGCCTAGGTGTGC | alpha_2_13 | ATTCACCGCGACGCGCTGATTCGCG | gamma_10_13 | ACTACCGGGTAGTTTCCTACGCGTT |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| flavo_3_14 | CTATCTATCGTAGCCTAGGTGTGCC | alpha_2_14 | CCGCGACGCGCTGATTCGCGATTAC | gamma_10_14 | CACTACCGGGTAGTTTCCTACGCGT |
| flavo_3_15 | CTATCGTAGCCTAGGTGTGCCGTTA | alpha_2_15 | CACCGCGACGCGCTGATTCGCGATT | gamma_10_15 | ACCGGGTAGTTTCCTACGCGTTACT |
| flavo_3_16 | TATCGTAGCCTAGGTGTGCCGTTAC | alpha_2_16 | CGCGACGCGCTGATTCGCGATTACT | gamma_10_16 | CCACTACCGGGTAGTTTCCTACGCG |
| flavo_3_17 | CTTATTGTCCACCTACGGACCCTT | alpha_2_17 | TCACCGCGACGCGCTGATTCGCGAT | gamma_10_17 | CCCCACTACCGGGTAGTTTCCTACG |
| flavo_3_18 | ACTTATTGTCCACCTACGGACCCT | alpha_2_18 | ACCGCGACGCGCTGATTCGCGATTA | gamma_10_18 | CCGGGTAGTTTCCTACGCGTTACTC |
| flavo_3_19 | GACTTATTGTCCACCTACGGACCC | alpha_2_19 | GCGACGCGCTGATTCGCGATTACTA | gamma_10_19 | CCCACTACCGGGTAGTTTCCTACGC |
| flavo_3_20 | TGACTTATTGTCCACCTACGGACC | alpha_2_20 | TTCACCGCGACGCGCTGATTCGCGA | gamma_10_20 | TACCGGGTAGTTTCCTACGCGTTAC |
| flavo_3_21 | CTGACTTATTGTCCACCTACGGAC | alpha_2_21 | TCCTCAGTGTCAGTAGTGACCCAGA | gamma_10_21 | CCCCACTACCGGGTAGTTTCCTAC |
| flavo_3_22 | AGATTGTATACGCGATACTCACCCG | alpha_2_22 | CCCAGAAAGTTGCCTTCGCATTTGG | gamma_10_22 | CTACCGGGTAGTTTCCTACGCGTTA |
| flavo_3_23 | GATTGTATACGCGATACTCACCCGT | alpha_2_23 | AGTGCGGGCTCATCTTTCGGCGTAT | gamma_10_23 | CTGTTGTCCCCCACTACTGGGTAGT |
| flavo_3_24 | TCTTCGGGCTATTCCCTAGTATGAG | alpha_2_24 | AAGTGCGGGCTCATCTTTCGGCGTA | gamma_10_24 | CTAGCTAATCTCACGCAGGCACATC |
| flavo_3_25 | CTTCGGGCTATTCCCTAGTATGAGG | alpha_2_25 | GTGCGGGCTCATCTTTCGGCGTATA | gamma_10_25 | CAACTAGCTAATCTCACGCAGGCAC |
| flavo_4_1 | CAGGAGATATTCCCATACTATGGGG | alpha_3_1 | CACCTGTATCCAATCACCCGAAGT | gamma_11_1 | GCTTTCCCCCGTAGGATATATGCGG |
| flavo_4_2 | TCAAACTCCCACACGTGGGAGTGGT | alpha_3_2 | ACCTGTATCCAATCACCCGAAGTG | gamma_11_2 | CTTTCCCCCGTAGGATATATGCGGT |
| flavo_4_3 | CAAACTCCCACACGTGGGAGTGGTT | alpha_3_3 | CCTGTATCCAATCACCCGAAGTGA | gamma_11_3 | TGCTTTCCCCCGTAGGATATATGCG |
| flavo_4_4 | GTCAAACTCCCACACGTGGGAGTGG | alpha_3_4 | GCACCTGTATCCAATCACCCGAAG | gamma_11_4 | CTGCTTTCCCCCGTAGGATATATGC |
| flavo_4_5 | GGAGATATTCCCATACTATGGGGCA | alpha_3_5 | GGCAGTTCCTTCCAAAGTTCCCACCA | gamma_11_5 | CCTGCTTTCCCCCGTAGGATATATG |
| flavo_4_6 | AGGAGATATTCCCATACTATGGGGC | alpha_3_6 | AGCACCTGTATCCAATCACCCGAA | gamma_11_6 | CCCTGCTTTCCCCCGTAGGATATAT |
| flavo_4_7 | CGTCAAACTCCCACACGTGGGAGTG | alpha_3_7 | CGGCAGTTCCTTCCAAAGTTCCACC | gamma_11_7 | CTCACTCAGGCTCATCAAAATAGCGC |
| flavo_4_8 | AAAACTCCCACACGTGGGAGTGGTTC | alpha_3_8 | CAGCACCTGTATCCAATCACCCGA | gamma_11_8 | CCCCTGCTTTCCCCCGTAGGATATA |
| flavo_4_9 | CTGGGCTATTCCCTCCAAAAGGTA | alpha_3_9 | CCGGCAGTTCCTTCCAAAGTTCCAC | gamma_11_9 | GTGTCAGTATCGAGCCAGTCAGTCG |
| flavo_4_10 | CCGTCAAACTCCCACACGTGGGAGT | alpha_3_10 | GCAGCACCTGTATCCAATCACCCG | gamma_11_10 | TCAGTGTCAGTATCGAGCCAGTCAG |
| flavo_4_11 | CTTAACCACTCAGCCCTTAATCGG | alpha_3_11 | TGCAGCACCTGTATCCAATCACCCC | gamma_11_11 | AGTGTCAGTATCGAGCCAGTCAGTC |
| flavo_4_12 | GTTTCCCTGGGCTATTCCCCTCCAA | alpha_3_12 | TCACCCGGCAGTTCCTTCCAAAGTTCC | gamma_11_12 | TGTCAGTATCGAGCCAGTCAGTCGC |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| flavo_4_13 | GCTTAACCACTCAGCCCTTAATCGG | alpha_3_13 | CTTACAAATCCGCCTACGCTCGCTT | gamma_11_13 | CAGTGTCAGTATCGAGCCAGTCAGT |
| flavo_4_14 | AACTCCCACACGTGGGAGTGGTTCT | alpha_3_14 | ATGCAGCACCTGTATCCAATCCACC | gamma_11_14 | CTCAGTGTCAGTATCGAGCCAGTCA |
| flavo_4_15 | ACCGTCAAACTCCCACACGTGGGAG | alpha_3_15 | CGGGCCCATCCAATAGCGCATAAAG | gamma_11_15 | TCCCCTGCTTTCCCCCGTAGGATAT |
| flavo_4_16 | CCACACGTGGGAGTGGTTCTTCCTC | alpha_3_16 | GGGCCCATCCAATAGCGCATAAAGC | gamma_11_16 | CCCCACCAACTAGCTAATCTCACTC |
| flavo_4_17 | AGTTTCCCTGGGCTATTCCCCTCCA | alpha_3_17 | GCGGGCCCATCCAATAGCGCATAAA | gamma_11_17 | CCTCAGTGTCAGTATCGAGCCAGTC |
| flavo_4_18 | TTAACCACTCAGCCCTTAATCGGGC | alpha_3_18 | ACTTACAAATCCGCCTACGCTCGCT | gamma_11_18 | GTCCCCTGCTTTCCCCCGTAGGATA |
| flavo_4_19 | CACGTGGGAGTGGTTCTTCCTCTGT | alpha_3_19 | CGCGGGCCCATCCAATAGCGCATAA | gamma_11_19 | TCAGTATCGAGCCAGTCAGTCGCCT |
| flavo_4_20 | CACACGTGGGAGTGGTTCTTCCTCT | alpha_3_20 | GGCCCATCCAATAGCGCATAAAGCT | gamma_11_20 | GTATCGAGCCAGTCAGTCAGTCGCCTTCG |
| flavo_4_21 | ACAGTGGGAGTGGTTCTTCCTCTG | alpha_3_21 | CACCGGCAGTTCCTTCAAAGTTCCC | gamma_11_21 | AGTATCGAGCCAGTCAGTCGCCTTC |
| flavo_4_22 | CGCTTAACCACTCAGCCCTTAATCG | alpha_3_22 | ACCGGCAGTTCCTTCAAAGTTCCCA | gamma_11_22 | TATCGAGCCAGTCAGTCGCCTTCGC |
| flavo_4_23 | ACGTGGGAGTGGTTCTTCCTCTGTA | alpha_3_23 | AACTTACAAATCCGCCTACGCTCGC | gamma_11_23 | ATCGAGCCAGTCAGTCGCCTTCGCC |
| flavo_4_24 | TTTCCCTGGGCTATTCCCCTCCAAA | alpha_3_24 | CGATAAAGCTTTTCTCCCGAAGGAC | gamma_11_24 | GTCAGTATCGAGCCAGTCAGTCGCC |
| flavo_4_25 | TTCCCTGGGCTATTCCCCTCCAAAA | alpha_3_25 | CATGCAGCACCTGTATCCAATCCAC | gamma_11_25 | CAGTATCGAGCCAGTCAGTCGCCTT |
| flavo_5_1 | CGTCAACAGTTCACACGTGAACCTT | roseo_1_1 | CTCTGGAATCCGCGACAAGTATGTC | gamma_12_1 | CACTACCTGGTAGATTCCTACGCGT |
| flavo_5_2 | ACAGTACCGTCAACAGTTCACACGT | roseo_1_2 | TGCCCCTATAAATAGTTGGCGCACC | gamma_12_2 | CCACTACCTGGTAGATTCCTACGCG |
| flavo_5_3 | CCGTCAACAGTTCACACGTGAACCT | roseo_1_3 | CCCTATAAATAGTTGGCGCACCACC | gamma_12_3 | CCCACTACCTGGTAGATTCCTACGC |
| flavo_5_4 | CAGTACCGTCAACAGTTCACACGTG | roseo_1_4 | CCCCTATAAATAGTTGGCGCACCAC | gamma_12_4 | AACTGTTGTCCCCACTACCTGGTA |
| flavo_5_5 | TACAGTACCGTCAACAGTTCACACG | roseo_1_5 | GCCCCTATAAATAGTTGGCGCACCA | gamma_12_5 | CAACTGTTGTCCCCACTACCTGGT |
| flavo_5_6 | ACCGTCAACAGTTCACACGTGAACC | roseo_1_6 | CGTGGTTGGCTGCCCCTATAAATAG | gamma_12_6 | CCAACTGTTGTCCCCACTACCTGG |
| flavo_5_7 | CTACAGTACCGTCAACAGTTCACAC | roseo_1_7 | CTGCCCTATAAATAGTTGGCGCAC | gamma_12_7 | CCCCACTACCTGGTAGATTCCTACG |
| flavo_5_8 | TACCGTCAACAGTTCACACGTGAAC | roseo_1_8 | CCGTGGTTGGCTGCCCCTATAAATA | gamma_12_8 | CGGTATTGCAACCCTCGTACGCCC |
| flavo_5_9 | AGTACCGTCAACAGTTCACACGTGA | roseo_1_9 | TGGCTGCCCCTATAAAATAGTTGGCG | gamma_12_9 | ACTGTTGTCCCCACTACCTGGTAG |
| flavo_5_10 | GTACCGTCAACAGTTCACACGTGAA | roseo_1_10 | GGCTGCCCCTATAAATAGTTGGCGC | gamma_12_10 | TCCAACTGTTGTCCCCACTACCTG |
| flavo_5_11 | CCTACAGTACCGTCAACAGTTCACA | roseo_1_11 | GGAATCCGCGACAAGTATGTCAAGG | gamma_12_11 | CCCCACTACCTGGTAGATTCCTAC |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| flavo_5_12 | TCCTACAGTACCGTCAACAGTTCAC | roseo_1_12 | GCTGCCCTATAAATAGTTGGGCCA | gamma_12_12 | GCGGTATTGCAACCCTCTGTACGCC |
| flavo_5_13 | CCGAAGAAAAGATGTTTCCACCCC | roseo_1_13 | ACCGTGGTTGGCTGCCCTATAAAT | gamma_12_13 | GCGGTATCGCAACCCTCTGTACGTT |
| flavo_5_14 | CTCAGACCCGCAATTAGTCCGAACAG | roseo_1_14 | CCATCTCTGGAATCCGCGACAAGTA | gamma_12_14 | TCTATCAGTTTGGGTGCAGTTCCC |
| flavo_5_15 | TAGCCACTCAGACCCGCAATTAGTCC | roseo_1_15 | ATAGTTGGCGCACCACCTTCGGGTA | gamma_12_15 | GTCTATCAGTTTGGGGTGCAGTTCC |
| flavo_5_16 | TTAGCCACTCAGACCCGCAATTAGTC | roseo_1_16 | GGAATCCATCTCTGGAATCCGGCAC | gamma_12_16 | CTGTTGTCCCCACTACCTGGTAGA |
| flavo_5_17 | ACTCAGACCCGCAATTAGTCCGAACA | roseo_1_17 | TACCGTGGTTGGCTGCCCTATAAA | gamma_12_17 | CTATCAGTTTGGGGTGCAGTTCCCA |
| flavo_5_18 | AGATGTTTCCACCCCTGTCAAACTG | roseo_1_18 | GAATCCGCGACAAGTATGTCAAGGG | gamma_12_18 | CTGTTGCTAACGTCACAGCTAAGGG |
| flavo_5_19 | CAGACCGCAATTAGTCCGAACAGCT | roseo_1_19 | TCCATCTCTGGAATCCGCGACAAGT | gamma_12_19 | CAGTTTGGGGTGCAGTTCCCAGGTT |
| flavo_5_20 | GCCACTCAGACCCGCAATTAGTCCGA | roseo_1_20 | ATCCATCTCTGGAATCCGCGGGTAG | gamma_12_20 | AGTTTGGGGTGCAGTTCCCAGGTTG |
| flavo_5_21 | CACTCAGACCCGCAATTAGTCCGAAC | roseo_1_21 | TAGTTGGCGCACCACCTTCGGGTAG | gamma_12_22 | TTCCAACTGTTGTCCCCACTACCT |
| flavo_5_22 | CTTAGCCACTCAGACCGCAATTAGT | roseo_1_22 | CCTACCGTGGTTGGCTGCCCTATA | gamma_12_22 | TATCAGTTTGGGGTGCAGTTCCCAG |
| flavo_5_23 | AGCCACTCAGACCCGCAATTAGTCCG | roseo_1_23 | CTACCGTGGTTGGCTGCCCTATAAA | gamma_12_23 | CGGTATCGCAACCCTCTGTACGTTC |
| flavo_5_24 | TCAGACCGCAATTAGTCCGAACAGC | roseo_1_24 | ACGTCGTCCACACCTTCCTCCGCT | gamma_12_24 | CCCCACCAACTAACTAATCTCACGC |
| flavo_5_25 | ACTTTCGCTTAGCCACTCAGACCGC | roseo_1_25 | GACGTCGTCCACACCTTCCTCCGGC | gamma_12_25 | GTCAGCGACTAGCAAGCTAGTCCTG |
| flavo_6_1 | AGTGCCGGAGTTAAGCCCCTGCATT | roseo_2_1 | GTCACCGGGTCACCGAAGTGAAAAC | gamma_13_1 | CGCCACTGAAAGACATTGTCTCCA |
| flavo_6_2 | GTGCCGGAGTTAAGCCCCTGCATTT | roseo_2_2 | ACCGGGTCACCGAAGTGAAAACCAG | gamma_13_2 | GCGCCACTGAAAGACATTGTCTCCC |
| flavo_6_3 | CAGTGCCGGAGTTAAGCCCCTGCAT | roseo_2_3 | CACCGGGTCACCGAAGTGAAAACCA | gamma_13_3 | TGCGCCACTGAAAGACATTGTCTCC |
| flavo_6_4 | TGCCGGAGTTAAGCCCCTGCATTTC | roseo_2_4 | TCACCGGGTCACCGAAGTGAAAACC | gamma_13_4 | TGTCAGTACAGATCAGGAGGCGC |
| flavo_6_5 | AGTTAAGCCCCTGCATTTCACCACT | roseo_2_5 | TGTCACCGGGTCACCGAAGTGAAAA | gamma_13_5 | GTGTCAGTACAGATCAGGAGGAGGCCG |
| flavo_6_6 | GCAGTGCCGGAGTTAAGCCCCTGCA | roseo_2_6 | CCGGGTCACCGAAGTGAAAACCAGA | gamma_13_6 | CTGCGCCACTGAAAGACATTGTCTC |
| flavo_6_7 | GTTAAGCCCCTGCATTTCACCACTG | roseo_2_7 | AGATCTCTGGCGGTCCCGGGATG | gamma_13_7 | CTTGGCTCCAAAAGGCACACTCTCA |
| flavo_6_8 | GGCAGTGCCGGAGTTAAGCCCCTGC | roseo_2_8 | ACCAGATCTCTGGCGGTCCCGGG | gamma_13_8 | GAGAGCTTCAAGAGAGGCCCTCTTT |
| flavo_6_9 | TGGCAGTGCCGGAGTTAAGCCCCTG | roseo_2_9 | AACCAGATCTCTGGCGGTCCCGG | gamma_13_9 | CGAGAGCTTCAAGAGAGGCCCTCTT |
| flavo_6_10 | GAGTTAAGCCCCTGCATTTCACCAC | roseo_2_10 | AAACCAGATCTCTGGCGGTCCCG | gamma_13_10 | GCGAGAGCTTCAAGAGAGGCCCTCT |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| flavo_6_11 | GCCGGAGTTAAGCCCTGCATTTCA | roseo_2_11 | TCTCTGGCGGTCCCGGGATGTCAAG | gamma_13_11 | TAGCGAGAGCTTCAAGAGAGCCCT |
| flavo_6_12 | ATGGCAGTGCCGGAGTTAAGCCCCT | roseo_2_12 | ATCTCTCTGGCGGTCCCGGGATGTC | gamma_13_12 | AGAGCTTCAAGAGAGCCCTCTTTC |
| flavo_6_13 | TTAAGCCCCTGCATTTCACCACTGA | roseo_2_13 | GATCTCTCTGGCGGTCCCGGGATGT | gamma_13_13 | AGCGAGAGCTTCAAGAGAGCCCTC |
| flavo_6_14 | GGAGTTAAGCCCCTGCATTTCACCA | roseo_2_14 | CAGATCTCTCTGGCGGTCCCGGGAT | gamma_13_14 | GTCAGTACAGATCCAGGAGGCCGC |
| flavo_6_15 | CGGAGTTAAGCCCCTGCATTTCACC | roseo_2_15 | TCTGGCGGTCCCGGGATGTCAAGGG | gamma_13_15 | TCAGTACAGATCCAGGAGGCCGCT |
| flavo_6_16 | CCCTGCATTTCACCACTGACTTATC | roseo_2_16 | CTCTGGCGGTCCCGGGATGTCAAGG | gamma_13_16 | CAGTACAGATCCAGGAGGCCCGCTT |
| flavo_6_17 | CAATGGCAGTGCCGGAGTTAAGCCC | roseo_2_17 | CCAGATCTCTCTGGCGGTCCCGGGA | gamma_13_17 | AGTACAGATCCAGGAGGCCGCCTC |
| flavo_6_18 | TCAATGGCAGTGCCGGAGTTAAGCC | roseo_2_18 | TCTCTCTGGCGGTCCCGGGATGTCA | gamma_13_18 | GCTGCCCACTGAAAGACATTGTCT |
| flavo_6_19 | CCTTACGGTCACCGACTTCAGGCAC | roseo_2_19 | CTCTCTGGCGGTCCCGGGATGTCAA | gamma_13_19 | GAGCTTCAAGAGAGGCCCTCTTTCT |
| flavo_6_20 | CCGGAGTTAAGCCCCTGCATTTCAC | roseo_2_20 | CTGGCGGTCCCGGGATGTCAAGGGT | gamma_13_20 | TCTTGGCTCCAAAAGGCACACTCTC |
| flavo_6_21 | AATGGCAGTGCCGGAGTTAAGCCCC | roseo_2_21 | ACCTGTCACCGGGTCACCGAAGTGA | gamma_13_21 | AGTGTCAGTACAGATCCAGGAGGCC |
| flavo_6_22 | TATCAATGGCAGTGCCGGAGTTAAG | roseo_2_22 | CCTGTCACCGGGTCACCGAAGTGAA | gamma_13_22 | GGCCCTCTTTCTCCCTTAGGAGGTA |
| flavo_6_23 | GTATCAATGGCAGTGCCGGAGTTAA | roseo_2_23 | CTGTCACCGGGTCACCGAAGTGAAA | gamma_13_23 | AGCTTCAAGAGAGGCCCTCTTTCTC |
| flavo_6_24 | CCCCTGCATTTCACCACTGACTTAT | roseo_2_24 | CGGGTCACCGAAGTGAAAACCAGAT | gamma_13_24 | AGCTGCGCCACTGAAAGACATTGTC |
| flavo_6_25 | TAAGCCCCTGCATTTCACCACTGAC | roseo_2_25 | AAAAACCAGATCTCTCTGGCGGTCC | gamma_13_25 | CGAGAGCATCAAGAGAGGCCCTCTT |
| flavo_7_1 | TCTTACAGTACCGTCACCAGACTAC | roseo_3_1 | GCCGCTACACCCGAAGGTGCCGCTC | gamma_14_1 | GGCGGTCAACTTACTACGTTAGCTG |
| flavo_7_2 | CTTACAGTACCGTCACCAGACTACA | roseo_3_2 | CTACACCCGAAGGTGCCGCTCGACT | gamma_14_2 | CCAGGCGGTCAACTTACTACGTTAG |
| flavo_7_3 | CGTCACCAGACTACACGTAGTCCTT | roseo_3_3 | GCTACACCCGAAGGTGCCGCTCGAC | gamma_14_3 | GCGGTCAACTTACTACGTTAGCTGC |
| flavo_7_4 | GTACCGTCACCAGACTACACGTAGT | roseo_3_4 | CCGGCTACACCCGAAGGTGCCGCTCG | gamma_14_4 | CAGGGCGGTCAACTTACTACGTTAGC |
| flavo_7_5 | CCGTCACCAGACTACACGTAGTCCT | roseo_3_5 | CGCTACACCCGAAGGTGCCGCTCGA | gamma_14_5 | CCCAGGCGGTCAACTTACTACGTTA |
| flavo_7_6 | TACCGTCACCAGACTACACGTAGTC | roseo_3_6 | CGCCGCTACACCCGAAGGTGCCGCT | gamma_14_6 | CCGAGGGCACTGCTTCATTACAAAG |
| flavo_7_7 | ACCGTCACCAGACTACACGTAGTCC | roseo_3_7 | CCGCCGCTACACCCGAAGGTGCCGC | gamma_14_7 | CGAGGGCACTGCTTCATTACAAAGC |
| flavo_7_8 | TTACAGTACCGTCACCAGACTACAC | roseo_3_8 | TACACCCGCTACACCCGAAGGTGCCGCTT ? | gamma_14_8 | TCCCGAGGGCACTGCTTCATTACAA |
| flavo_7_9 | GTCACCAGACTACACGTAGTCCTTA | roseo_3_9 | TCCGCCGCTACACCCGAAGGTGCCG | gamma_14_9 | CCCGAGGGCACTGCTTCATTACAAA |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| flavo_7_10 | TACAGTACCGTCACCAGACTACACG | roseo_3_10 | ACACCCGAAGGTGCCGCTCGACTTG | gamma_14_10 | CCCCAGGCGGTCAACTTACTACGTT |
| flavo_7_11 | ACAGTACCGTCACCAGACTACACGT | roseo_3_11 | GTCCGCCGCTACACCCGAAGGTGCC | gamma_14_11 | TCCCCAGGCGGTCAACTTACTACGT |
| flavo_7_12 | AACTTTCACCCCTGACTTAACAGCC | roseo_3_12 | ACCCGAAGGTGCCGCTCGACTTGCA | gamma_14_12 | CTCCCGAGGGCACTGCTTCATTACA |
| flavo_7_13 | CAGTACCGGTCACCAGACTACACGTA | roseo_3_13 | CACCCGCGCTACACCCGAAGGTGC | gamma_14_13 | CTCCCCAGGCGGTCAACTTACTACG |
| flavo_7_14 | CCGGTCGTCAGCAAGAGCAAGCTCC | roseo_3_14 | CGTCCGCGCTACACCCGAAGGTGC | gamma_14_14 | GCTCCCGAGGGCACTGCTTCATTAC |
| flavo_7_15 | ACTTTCACCCCTGACTTAACAGCCC | roseo_3_15 | CACCTGGTCTCTTACGACGAAAACCG | gamma_14_15 | TCTTGGCTCCCGAGGGCACTGCTTC |
| flavo_7_16 | CCCTGACTTAACAGCCCGCCTACG | roseo_3_16 | CCAGGAGTTTTGGAGGCCGTTCCAG | gamma_14_16 | GGCTCCCGAGGGCACTGCTTCATTA |
| flavo_7_17 | TCGCTTGGCCGCTCAGATCGAAATC | roseo_3_47 | ACCTGGTCTCTTACGAGAAAACCGG | gamma_14_47 | TATCTTGGCTCCCGAGGGCACTGCT |
| flavo_7_18 | CGCTTGGCCGCTCAGATCGAAATCG | roseo_3_18 | CCGGATCTCTTCCGGCGGTCCAGGA | gamma_14_18 | ACTCCCCAGGCGGTCAACTTACTAC |
| flavo_7_19 | TTCGCTTGGCCGCTCAGATCGAAAT | roseo_3_19 | CCCGAAGGTGCCCCTCGACTTGCAT | gamma_14_19 | ATCTTGGCTCCCGAGGGCACTGCTT |
| flavo_7_20 | TTTCGCTTGGCCGCTCAGATCGAAA | roseo_3_20 | ACCAGGAGTTTTGGAGGCCGTTCCA | gamma_14_20 | TACTACGTTAGCTGCGCCACTGAGA |
| flavo_7_21 | GCTTGGCCGCTCAGATCGAAATCCA | roseo_3_21 | CAGGAGTTTTGGAGGCCGTTCCAGG | gamma_14_21 | GTATCTTGGCTCCCGAGGGCACTGC |
| flavo_7_22 | CTTGGCCGCTCAGATCGAAATCCAA | roseo_3_22 | CCGAAGGTGCCCCTCGACTTGCATG | gamma_14_22 | CTTGGCTCCCGAGGGCACTGCTTCA |
| flavo_7_23 | TTGGCCGCTCAGATCGAAATCCAAA | roseo_3_23 | CCGTCCGCCGCTACACCCGAAGGTG | gamma_14_23 | TGGCTCCCGAGGGCACTGCTTCATT |
| flavo_7_24 | GGCTATCCCTTAGTGTAAGGCAGCA | roseo_3_24 | AAACCGGATCTCTTCCGGCGCGTCCAG | gamma_14_24 | ACTACGTTAGCTGCCACTGAGAA |
| flavo_7_25 | GGGCTATCCCTTAGTGTAAGGCAGA | roseo_3_25 | CCTGGTCTCTTACGAGAAAACCGGA | gamma_14_25 | TTGGCTCCCGAGGGCACTGCTTCAT |
| flavo_8_1 | GCCGAAATACGGTACTACGGGGCAT | roseo_4_1 | CGTACCATCTCTGGTAGTAGCACAG | gamma_15_1 | TCCGTAGAAGTCCGGCCGTGTCTC |
| flavo_8_2 | GATGCCGAAATACGGTACTACGGGG | roseo_4_2 | CCATCTCTGGTAGTAGCACAGGATG | gamma_15_2 | CCGTAGAAGTCCGGGCCGTGTCTCA |
| flavo_8_3 | ATGCCGAAATACGGTACTACGGGGC | roseo_4_3 | GTACCATCTCTGGTAGTAGCACAGG | gamma_15_3 | CGTAGAAGTCCGGGCCGTGTCTCAG |
| flavo_8_4 | TGCCGAAATACGGTACTACGGGGCA | roseo_4_4 | CTGGTAGTAGCACAGGATGTCAAGG | gamma_15_4 | GTAGAAGTCCGGGCCGTGTCTCAGT |
| flavo_8_5 | ACCGTATAACGATGCCGAAATACGG | roseo_4_5 | TGGTAGTAGCACAGGATGTCAAGGG | gamma_15_5 | TTCCGTAGAAGTCCGGGCCGTGTCT |
| flavo_8_6 | CCGTATAACGATGCCGAAATACGGT | roseo_4_6 | GAAGGGACGTACCATCTCTGGTAG | gamma_15_6 | CTTCCGTAGAAGTCCGGGCCGTGTC |
| flavo_8_7 | CGATGCCGAAATACGGTACTACGGG | roseo_4_7 | CCTTAGAGAAGGGCATATTCCCACG | gamma_15_7 | TAGAAGTCCGGGCCGTGTCTCAGTC |
| flavo_8_8 | CCGAAATACGGTACTACGGGGCATT | roseo_4_8 | GGTAGTAGCACAGGATGTCAAGGGT | gamma_15_8 | ACTGCTGCCTTCCGTAGAAGTCCGG |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| flavo_8_9 | ACGATGCCGAAATACGGTACTACGG | roseo_4_9 | GGGAACGTACCATCTCTGGTAGTAG | gamma_15_9 | CATGCAGTCGAGTTCCAGACTGCAA |
| flavo_8_10 | AACGATGCCGAAATACGGTACTACG | roseo_4_10 | GGAACGTACCATCTCTGGTAGTAGC | gamma_15_10 | CCTCGAGCTATCCCCTCCATTGGG |
| flavo_8_11 | CGAAGGAAAAGTCATCTCTGACCCT | roseo_4_11 | CGAAGGAACGTACCATCTCTGTA | gamma_15_11 | AGAAGTCCGGGCCGTGTCTCAGTCC |
| flavo_8_12 | CGAAATACGGTACTACGGGGCATTA | roseo_4_12 | CCGAAGGAACGTACCATCTCTGGT | gamma_15_12 | TCCTCGAGCTATCCCCTCCATTGG |
| flavo_8_13 | CCGAAGGAAAAGTCATCTCTGACCC | roseo_4_13 | CGTCCCCGAAGGAACGTACCATCT | gamma_15_13 | CTCGAGCTATCCCCTCCATTGGGT |
| flavo_8_14 | GTCATCTCTGACCCTGTCAATATGC | roseo_4_14 | CCCCGAAGGGAACGTACCATCTCTG | gamma_15_14 | TCATGCAGTCGAGTTCCAGACTGCA |
| flavo_8_15 | CCCGAAGGAAAAGTCATCTCTGACC | roseo_4_15 | GTCCCCGAAGGGAACGTACCATCTC | gamma_15_15 | CCTTCCGTAGAAGTCCGGGCCGTGT |
| flavo_8_16 | TACAAGGCAGGTTCCATACGCGGTG | roseo_4_16 | GCGTCCCCGAAGGGAACGTACCATC | gamma_15_16 | GCGCCACTGGATAAATCCAACGGCT |
| flavo_8_17 | GGCTTTAACGGTATAACGATGCCGA | roseo_4_17 | ACTGCGTCCCCGAAGGGAACGTACC | gamma_15_17 | TGCGCCACTGGATAAATCCAACGGC |
| flavo_8_18 | CTGGGCTATTCCCCTGTACAAGGCA | roseo_4_18 | CTGCGTCCCCGAAGGAACGTACCA | gamma_15_18 | TTCCTCGAGCTATCCCCTCCATTG |
| flavo_8_19 | GAAGGAAAAGTCATCTCTGACCCTG | roseo_4_19 | CCCGAAGGAACGTACCATCTCTGG | gamma_15_19 | GTTCCAGACTGCAATTGCAGGACTACG |
| flavo_8_20 | GCCCGAAGGAAAAGTCATCTCTGAC | roseo_4_20 | TGCGTCCCCGAAGGAACGTACCAT | gamma_15_20 | CCAGCTCGCGCTTTGCAACCGTTT |
| flavo_8_21 | GTACAAGGCAGGTTCCATACGCGGT | roseo_4_21 | CTTAGAGAAGGGCATATTCCCACGC | gamma_15_21 | TCGAGCTATCCCCTCCATTGGGTA |
| flavo_8_22 | TGTACAAGGCAGGTTCCATACGCGG | roseo_4_22 | GAAGGGCGCGTCCCGACTTGCATGTA | gamma_15_22 | GCTGCCACTGGATAAATCCAACG |
| flavo_8_23 | CCTGGGCTATTCCCCTGTACAAGGC | roseo_4_23 | CACTGCGTCCCCGAAGGGAACGTAC | gamma_15_23 | CGCCACTGGATAAATCCAACGGCTA |
| flavo_8_24 | ACAAGGCAGGTTCCATACGCGGGTGC | roseo_4_24 | TCACTGCGTCCCCGAAGGGAACGTA | gamma_15_24 | CTGCGCCACTGGATAAATCCAACGG |
| flavo_8_25 | GGCAGGTTCCATACGCGGTGCGCAC | roseo_4_25 | TCCCCGAAGGAACGTACCATCTCT | gamma_15_25 | TTTCCTCGAGCTATCCCCTCCATT |
| flavo_9_1 | ATTCCGCCTACTTCAATACAACTCA | roseo_5_1 | GTCACTATGTCCCGAAGGAAAGCCT | gamma_16_1 | TTTAAGGGTTTGGCTCCAGCTCGCG |
| flavo_9_2 | TTCCGCCTACTTCAATACAACTCAA | roseo_5_2 | CCGAAGGAAAGCCTGATCTCTCAGG | gamma_16_2 | TTTTAAGGGTTTGGCTCCAGCTCGC |
| flavo_9_3 | TATTCCGCCTACTTCAATACAACTC | roseo_5_3 | TGTCACTATGTCCGAAGGAAAGCC | gamma_16_3 | TTAAGGGTTTGGCTCCAGCTCGCGC |
| flavo_9_4 | TCCGCCTACTTCAATACAACTCAAG | roseo_5_4 | TCCGAAGGAAAGCCTGATCTCTCA | gamma_16_4 | GTTTTAAGGGTTTGGCTCCAGCTCG |
| flavo_9_5 | CATATTCCGCCTACTTCAATACAAC | roseo_5_5 | TCACTATGTCCCGAAGGAAAGCCTG | gamma_16_5 | CACGCGGTATACCTGGATCAGGGTT |
| flavo_9_6 | CCGCCTACTTCAATACAACTCAAGA | roseo_5_6 | CCCGAAGGAAAGCCTGATCTCTCAG | gamma_16_6 | ACACGCGGTATACCTGGATCAGGGT |
| flavo_9_7 | CGCCTACTTCAATACAACTCAAGAT | roseo_5_7 | CTGTCACTATGTCCCGAAGGAAAGC | gamma_16_7 | CTTCCTCCGGGTTTCACCCGGCAGT |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| flavo_9_8 | GAACTCAAGGTCCCGAACAGCTAGT | roseo_5_8 | GTCCCGAAGGAAAGCCTGATCTCTC | gamma_16_8 | TCCTCCGGGTTTCACCCGGCAGTCT |
| flavo_9_9 | TCAGAACTCAAGGTCCCGAACAGCT | roseo_5_9 | GCCTGATCTCTCAGGTTGTCATAGG | gamma_16_9 | CTTCACACACGCGGTATACCTGGAT |
| flavo_9_10 | ACTCAAGGTCCCGAACAGCTAGTAT | roseo_5_10 | TGACTGACTAATCCGCCTACGTACG | gamma_16_10 | CACACACGCGGTATACCTGGATCAGG |
| flavo_9_11 | GATGCCTATCAATAATACCATGAGG | roseo_5_11 | CTGACTGACTAATCCGCCTACGTAC | gamma_16_11 | ACACACGCGGTATACCTGGATCAGG |
| flavo_9_12 | AGAACTCAAGGTCCCGAACAGCTAG | roseo_5_12 | CGAAGGAAAGCCTGATCTCTCAGGT | gamma_16_12 | CACACACGCGGTATACCTGGATCAG |
| flavo_9_13 | CTCAAGGTCCCGAACAGCTAGTATC | roseo_5_13 | CACTATGTCCCGAAGGAAAGCCTGA | gamma_16_13 | CCTTCCTCCGGGTTTCACCCGGCAG |
| flavo_9_14 | AACTCAAGGTCCCGAACAGCTAGTA | roseo_5_14 | GCACCTGTCACTATGTCCCGAAGGA | gamma_16_14 | TTCCTCCGGGTTTCACCCGGCAGTC |
| flavo_9_15 | CAGAACTCAAGGTCCCGAACAGCTA | roseo_5_15 | CCTGTCACTATGTCCCGAAGGAAAG | gamma_16_15 | CCTCCGGGTTTCACCCGGCAGTCTC |
| flavo_9_16 | CTCAGAACTCAAGGTCCCGAACAGC | roseo_5_16 | CTATGTCCCGAAGGAAAGCCTGATC | gamma_16_16 | TTCACACACGCGGTATACCTGGATC |
| flavo_9_17 | TCAAGGTCCCGAACAGCTAGTATCC | roseo_5_17 | ATGTCCCGAAGGAAAGCCTGATCTC | gamma_16_17 | CGCCTTCCTCCGGGTTTCACCCGGC |
| flavo_9_18 | GCTCAGAACTCAAGGTCCCGAACAG | roseo_5_18 | AGCACCTGTCACTATGTCCCGAAGG | gamma_16_18 | CTCCGGGTTTCACCCGGCAGTCTCC |
| flavo_9_19 | CTACATATTCCGCCTACTTCAATAC | roseo_5_19 | CAGCACCTGTCACTATGTCCCGAAG | gamma_16_19 | GCGGTATACCTGGATCAGGGTTGCC |
| flavo_9_20 | GCCTACTTCAATACAACTCAAGATG | roseo_5_20 | CCTCCGAAGAGGTTAGCGCACCGCC | gamma_16_20 | CGGTATACCTGGATCAGGGTTGCCC |
| flavo_9_21 | TACACGTAAGGCTTATTCTTCCTGT | roseo_5_21 | TCCGCTGCCTCCTCCGAAGAGGTTA | gamma_16_21 | GGTATACCTGGATCAGGGTTGCCCC |
| flavo_9_22 | CACGTAAGGCTTATTCTTCCTGTAT | roseo_5_22 | CCGGCTGCCTCCTCCGAAGAGGTTAG | gamma_16_22 | TCTTCACACACGCGGTATACCTGGA |
| flavo_9_23 | ACACGTAAGGCTTATTCTTCCTGTA | roseo_5_23 | TGTCCCGAAGGAAAGCCTGATCTCT | gamma_16_23 | TCACACACGCGGTATACCTGATCA |
| flavo_9_24 | CTTAGCCGTCAGAACTCAAGGTCC | roseo_5_24 | CACCTGTCACTATGTCCCGAAGGAA | gamma_16_24 | GCCTTCCTCCGGGTTTCACCCGGCA |
| flavo_9_25 | CGCTCAGAACTCAAGGTCCCGAACA | roseo_5_25 | GCAGCACCTGTCACTATGTCCCGAA | gamma_16_25 | CGCGGTATACCTGGATCAGGGTTGC |
| flavo_10_1 | CGCTTAGCCACTCATCTAACCAATG | roseo_6_1 | CGATAAAACCTAGTCTCCTAGGCGG | gamma_17_1 | GGCTCCTCCAATAGTGACCGGTCCG |
| flavo_10_2 | CTTTCGCTTAGCCACTCATCTAACC | roseo_6_2 | CCGAGGCTATTCCGAAGCAAAAGGT | gamma_17_2 | AGGCTCCTCCAATAGTGACCGGTCC |
| flavo_10_3 | ACACGTCGGAGTGTTTCTTCCTGTA | roseo_6_3 | CCCGAGGCTATTCCGAAGCAAAAGG | gamma_17_3 | CAGGCTCCTCCAATAGTGACCGGTC |
| flavo_10_4 | CCCGTGCGCCACTCGTCATCTGGTG | roseo_6_4 | AAAACCTAGTCTCCTAGGCGGTCAG | gamma_17_4 | CATGTATTAGGCCTGCCGCCAACGT |
| flavo_10_5 | ACCCGTGCGCCACTCGTCATCTGGT | roseo_6_5 | AAACCTAGTCTCCTAGGCGGTCAGA | gamma_17_5 | GCTCCTCCAATAGTGACCGGTCCGA |
| flavo_10_6 | CACCCGTGCGCCACTCGTCATCTGG | roseo_6_6 | TCCCGAGGCTATTCCGAAGCAAAAG | gamma_17_6 | GCAGGCTCCTCCAATAGTGACCGGT |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
| --- | --- | --- | --- | --- | --- |
| flavo_10_7 | TACAACCCGTAGGGCTTTCATCCTG | roseo_6_7 | CTAGTCTCCTAGGCGGTCAGAGGAT | gamma_17_7 | CGCCTGAGAGCAAGCTCCCATCGTT |
| flavo_10_8 | ACAACCCGTAGGGCTTTCATCCTGC | roseo_6_8 | AACCTAGTCTCCTAGGCGGTCAGAG | gamma_17_8 | ACGCCTGAGAGCAAGCTCCCATCGT |
| flavo_10_9 | AACCCGTAGGGCTTTCATCCTGCAC | roseo_6_9 | CCTAGTCTCCTAGGCGGTCAGAGGA | gamma_17_9 | GCCTGAGAGCAAGCTCCCATCGTTT |
| flavo_10_10 | CAGTTTACAACCCGTAGGGCTTTCA | roseo_6_10 | TAGTCTCCTAGGCGGTCAGAGGATG | gamma_17_10 | GACGCCTGAGAGCAAGCTCCCATCG |
| flavo_10_11 | CAACCCGTAGGGCTTTCATCCTGCA | roseo_6_11 | CCTCTCAAACCAGCTACTGATCGCA | gamma_17_11 | AATCCTACGCAGGCTCCTCCAATAG |
| flavo_10_12 | TTACAACCCGTAGGGCTTTCATCCT | roseo_6_12 | TCCTCTCAAACCAGCTACTGATCGC | gamma_17_12 | GCATGTATTAGGCCTGCCGCCAACG |
| flavo_10_13 | AGCAGTTTACAACCCGTAGGGCTTT | roseo_6_13 | CTCTCAAACCAGCTACTGATCGCAG | gamma_17_13 | CTAATCCTACGCAGGCTCCTCCAAT |
| flavo_10_14 | GCAGTTTACAACCCGTAGGGCTTTC | roseo_6_14 | CTCAAACCAGCTACTGATCGCAGAC | gamma_17_14 | GCTAATCCTACGCAGGCTCCTCCAA |
| flavo_10_15 | AAGCAGTTTACAACCCGTAGGGCTT | roseo_6_15 | CAGCTACTGATCGCAGACTTGGTAG | gamma_17_15 | CGAGAGCAAGCTCCCATCGTTTCC |
| flavo_10_16 | CACGTTCGGAGTGTTCTTCCTGTAT | roseo_6_16 | CCAGCTACTGATCGCAGACTTGGTA | gamma_17_16 | CCTGAGAGCAAGCTCCCATCGTTTC |
| flavo_10_17 | TGCGCCCACTCGTCATCTGGTGCAA | roseo_6_17 | CCATGCAGCACCTGTCACTCTGTAT | gamma_17_17 | CTCCTCCAATAGTGACCGGTCCGAA |
| flavo_10_18 | CCGTGCGCCACTCGTCATCTGGTGC | roseo_6_18 | CATGCAGCACCTGTCACTCTGTATC | gamma_17_18 | ATCCTACGCAGGCTCCTCCAATAGT |
| flavo_10_19 | GCGCGCCACTCGTCATCTGGTGCAA | roseo_6_19 | AACCAGTACTGATCGCAGACTTGG | gamma_17_19 | CGCAGGCTCCTCCAATAGTGACCGG |
| flavo_10_20 | CGTGCGCCACTCGTCATCTGGTGCA | roseo_6_20 | ACCAGCTACTGATCGCAGACTTGGT | gamma_17_20 | AGCTAATCCTACGCAGGCTCCTCCA |
| flavo_10_21 | GTGCGCCACTCGTCATCTGGTGCAA | roseo_6_21 | GCCATGCAGCACCTGTCACTCTGTA | gamma_17_21 | TCGAGCCCTGAGAGCAAGCTCCCAT |
| flavo_10_22 | GTTTACAACCCGTAGGGCTTTCATC | roseo_6_22 | AGTTTCCCGAGGCTATTCCGAAGCA | gamma_17_22 | CTGAGAGCAAGCTCCCATCGTTTCC |
| flavo_10_23 | TTTACAACCCGTAGGGCTTTCATCC | roseo_6_23 | GTTTCCCGAGGCTATTCCGAAGCAA | gamma_17_23 | TGTATTAGGCCTGCCGCCAACGTTC |
| flavo_10_24 | GCACCCGTGCGCCACTCGTCATCTG | roseo_6_24 | GGCGGTCAGAGGATGTCAAGGGTTG | gamma_17_24 | TGCATGTATTAGGCCTGCCGCCAAC |
| flavo_10_25 | GCGAAGTGGCTGCTCTGTCATCTGGTGCA | roseo_6_25 | AGGCGGTCAGAGGATGTCAAGGGTT | gamma_17_25 | CGCCACCGGTATTCCTCAGAATATC |
| flavo_11_1 | GTACAAGTACTTTATGCTGCCCCTC | alpha_4_1 | CGACAGGACATGCCTGCCACAACTA | gamma_19_1 | GAGGTTGCGACCCTTTGTCTTCCC |
| flavo_11_2 | CCGCCGGAGCTTTTCTTAAAAACTC | alpha_4_2 | CCGACAGGACATGCCTGCCACAACT | gamma_19_2 | GCGAGGTTGCGACCCTTTGTCTTC |
| flavo_11_3 | CGGTCGCCATCAAAGTACAAGTACT | alpha_4_3 | ACCGACAGGACATGCCTGCCACAAC | gamma_19_3 | CGAAACCTTTCAAGAAGAGGGCTCC |
| flavo_11_4 | CCGGTCGCCATCAAAGTACAAGTAC | alpha_4_4 | GACAGGACATGCCTGCCAACAACTAG | gamma_19_4 | AAAGTGGTGAGCGCCCAGATAAGCT |
| flavo_11_5 | CGTCCCTCAGCGTCAGTTAATTGTT | alpha_4_5 | CCGTCTGCCACTATATCGTTCGACT | gamma_19_5 | TGAGCGCCCAGATAAGCTACCCACT |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| flavo_11_6 | TACAAGTACTTTATGCTGCCCCTCG | alpha_4_6 | CACCGACAGGCATGCCTGCCAACAA | gamma_19_6 | CAAAGTGGTGAGCGCCCAGATAAGC |
| flavo_11_7 | CACGCGGCATCGCTGGATCAGAGTT | alpha_4_7 | CCCGTCTGCCACTATATCGTTCGAC | gamma_19_7 | GTGGTGAGCGCCCAGATAAGCTACC |
| flavo_11_8 | TCGTCCCTCAGCGTCAGTTAATTGT | alpha_4_8 | CAGGCATGCCTGCCAACAACTAGCT | gamma_19_8 | AGTGGTGAGCGCCCAGATAAGCTAC |
| flavo_11_9 | TCACCGCGGCTCATCGCTGGATCAGAGT | alpha_4_9 | ACAGGCATGCCTGCCAACAACTAGC | gamma_19_9 | GTGAGCGCCCAGATAAGCTACCCAC |
| flavo_11_10 | TGCCAGTATCAAAGGCAGTTCTACC | alpha_4_10 | TCACCGACAGGCATGCCTGCCAACA | gamma_19_10 | GGTGAGCGCCCAGATAAGCTACCCA |
| flavo_11_11 | ACAAGTACTTTATGCTGCCCCTCGA | alpha_4_11 | GCATGCCTGCCAACAACTAGCTCTC | gamma_19_11 | TGGTGAGCGCCCAGATAAGCTACCC |
| flavo_11_12 | GTACATCGAACAGCTAGTGACCATC | alpha_4_12 | GGCATGCCTGCCAACAACTAGCTCT | gamma_19_12 | AAGTGGTGAGCGCCCAGATAAGCTA |
| flavo_11_13 | GCCAGTATCAAAGGCAGTTCTACCG | alpha_4_13 | CACCCGTCTGCCACTATATCGTTCG | gamma_19_13 | CGCCCAGATAAGCTACCCACTTCTT |
| flavo_11_14 | TTCGTCCCTCAGCGTCAGTTAATTG | alpha_4_14 | ACCCGTCTGCCACTATATCGTTCGA | gamma_19_14 | GCGCCCAGATAAGCTACCCACTTCT |
| flavo_11_15 | CAAGTACTTTATGCTGCCCCTCGAC | alpha_4_15 | GTCACCGACAGGCATGCCTGCCAAC | gamma_19_15 | GCGAAACCTTTCAAGAGAGAGGCTC |
| flavo_11_16 | CGCCGGTCGCCATCAAAGTACAAGT | alpha_4_16 | AGGCATGCCTGCCAACAACTAGCTC | gamma_19_16 | AGCGCCCAGATAAGCTACCCACTTC |
| flavo_11_17 | TCGCCGGTCGCCATCAAAGTACAAG | alpha_4_17 | CTCACCCGTCTGCCACTATATCGTT | gamma_19_17 | ACAAAGTGGTGAGCGCCCAGATAAG |
| flavo_11_18 | GCCCGGTCGCCATCAAAGTACAAGTA | alpha_4_18 | TCACCCGTCTGCCACTATATCGTTC | gamma_19_18 | CACAAAGTGGTGAGCGCCCAGATAA |
| flavo_11_19 | TTCGCCGGTCGCCATCAAAGTACAA | alpha_4_19 | CATGCCTGCCAACAACTAGCTCTCA | gamma_19_19 | CGAGGTTGCGACCCTTTGTCCTTCC |
| flavo_11_20 | CGTTCGCCGGTCGCCATCAAAGTAC | alpha_4_20 | CCTGCCAACAACTAGCTCTCATCGT | gamma_19_20 | GAGCGCCCAGATAAGCTACCCACTT |
| flavo_11_21 | GTTCGCCGGTCGCCATCAAAGTACA | alpha_4_21 | CGTCACCGACAGGCATGCCTGCCAA | gamma_19_21 | CGCGAGGTTGCGACCCTTTGTCCTT |
| flavo_11_22 | TACTTATCGGAGCTTAGGTGAGCCG | alpha_4_22 | CTCGGTATTCCGCTAACCTCTCTG | gamma_19_22 | GACGCTAAGAGCAAGCTCTTATCG |
| flavo_11_23 | TATCGGAGCTTAGGTGAGCCGTTAC | alpha_4_23 | ACTCACCCGTCTGCCACTATATCGT | gamma_19_23 | TCACAAAGTGGTGAGCGCCCAGATA |
| flavo_11_24 | CCCTGACTTAACAAACAGCCTGCGG | alpha_4_24 | GCGTCACCGACAGGCATGCCTGCCA | gamma_19_24 | GCAGGCTCATCTGATAGCGAAACCT |
| flavo_11_25 | ACCGTTGAGCGGTAGGATTTCACCC | alpha_4_25 | TACTCACCCGTCTGCCACTATATCG | gamma_19_25 | CGAGCCTAAGGAGCAAGCTCTTATC |
| flavo_12_1 | CGTCTTCCTGCACGCTGCATGGCTG | wolbach_1_1 | GCCAGGACTTCTTCTGTGAGTACCG | gamma_20_1 | CCACTAAGGGACAAATTCCCCAAC |
| flavo_12_2 | CCGTCTTCCTGCACGCTGCATGGCT | wolbach_1_2 | AGCCAGGACTTCTTCTGTGAGTACC | gamma_20_2 | CGCCACTAAGGGACAAATTCCCCA |
| flavo_12_3 | GTCTTCCTGCACGCTGCATGGCTGG | wolbach_1_3 | CCAAGGACTTCTTCTGTGAGTACCGT | gamma_20_3 | GCCACTAAGGGACAAATTCCCCAA |
| flavo_12_4 | CTTCCTGCACGCTGCATGGCTGGAT | wolbach_1_4 | CGGAGTTAGCACCAGGACTTCTTCTGT | gamma_20_4 | CACTAAGGGACAAATTCCCCAACG |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| flavo_12_5 | TTCCTGCACGCTGCATGGCTGGATC | wolbach_1_5 | CCGGCCGAACCGACCCTATCCCTTC | gamma_20_5 | ACTAAGGGACAAATTCCCCCAACGG |
| flavo_12_6 | GCCGTCTTCCTGCACGCTGCATGGC | wolbach_1_6 | ACGGAGTTAGCCAGGACTTCTTCTG | gamma_20_6 | CTAAGGGACAAATTCCCCCAACGGC |
| flavo_12_7 | TCTTCCTGCACGCTGCATGGCrGGA | wolbach_1_7 | GGAGTTAGCCAGGACTTCTTCTGTG | gamma_20_7 | GCGCCACTAAGGGACAAATTCCCCC |
| flavo_12_8 | CACGCTGCATGGCTGGATCAGAGTT | wolbach_1_8 | CAGGACTTCTTCTGTGAGTACCGTC | gamma_20_8 | GGTACCGTCAAGACGCGCAGTTATT |
| flavo_12_9 | GGCCGTCTTCCTGCACGCTGCATGG | wolbach_1_9 | GGCACGGAGTTAGCCAGGACTTCTT | gamma_20_9 | AGGTACCGTCAAGACGCGCAGTTAT |
| flavo_12_10 | TGCCCACCTTTTACCACCGGAGTTT | wolbach_1_10 | CACGGAGTTAGCCAGGACTTCTTCT | gamma_20_10 | TAGGTACCGTCAAGACGCGCAGTTA |
| flavo_12_11 | ATGCCCACCTTTTACCACCGGAGTT | wolbach_1_11 | TGGCACGGAGTTAGCCAGGACTTCT | gamma_20_11 | TGCGCCACTAAGGGACAAATTCCCC |
| flavo_12_12 | CACACGTGGACAGATTTCTTCCTGT | wolbach_1_12 | GCACGGAGTTAGCCAGGACTTCTTC | gamma_20_12 | TAAGGGACAAATTCCCCCAACGGCT |
| flavo_12_13 | GAAGACTCGCTCTTCCTCGCGGAGT | wolbach_1_13 | CGCCTCAGCGTCAGATTTGAACCAG | gamma_20_13 | CTGTAGGTACCGTCAAGACGCGCAG |
| flavo_12_14 | CATGCCCACCTTTTACCACCGGAGT | wolbach_1_14 | GCGCCTCAGCGTCAGATTTGAACCA | gamma_20_14 | GTAGGTACCGTCAAGACGCGCAGTT |
| flavo_12_15 | CCGGCTTTGAAGACTCGCTCTTCCT | wolbach_1_15 | CTGGCACGGAGTTAGCCAGGACTTC | gamma_20_15 | CTGCGCCACTAAGGGACAAATTCCC |
| flavo_12_16 | CCACACGTGGACAGATTTCTTCCTG | wolbach_1_16 | CTGCTGGCACGGAGTTAGCCAGGAC | gamma_20_16 | TGTAGGTACCGTCAAGACGCGCAGT |
| flavo_12_17 | TTTGAAGACTCGCTCTTCCTCGCGG | wolbach_1_17 | GTTGGCACGGAGTTAGCCAGGACTT | gamma_20_17 | TCTGTAGGTACCGTCAAGACGCGCA |
| flavo_12_18 | GGCTTTGAAGACTCGCTCTTCCTCG | wolbach_1_18 | TGCTGGCACGGAGTTAGCCAGGACT | gamma_20_18 | GCTGCCCACTAAGGGACAAATTCC |
| flavo_12_19 | CTTTGAAGACTCGCTCTTCCTCGCG | wolbach_1_19 | CCCGCCTCAGCGTCAGATTTGAACC | gamma_20_19 | CTTCTGTAGGTACCGTCAAGACGCG |
| flavo_12_20 | TGAAGACTCGCTCTTCCTCGCGGAG | wolbach_1_20 | GCCTTCGCGCCTCAGCGTCAGATTT | gamma_20_20 | TCTTCTGTAGGTACCGTCAAGACGC |
| flavo_12_21 | GACCGGCTTTGAAGACTCGCTCTTC | wolbach_1_21 | GCCTCAGCGTCAGATTTGAACCAGA | gamma_20_21 | GGACAAATTCCCCCAACGGCTAGTT |
| flavo_12_22 | CGGCTTTGAAGACTCGCTCTTCCTC | wolbach_1_22 | TCGCGCCTCAGCGTCAGATTTGAAC | gamma_20_22 | GACAAATTCCCCCAACGGCTAGTTG |
| flavo_12_23 | GCTTTGAAGACTCGCTCTTCCTCGC | wolbach_1_23 | CATGCAACACCTGTGTGAAACCCGG | gamma_20_23 | AGCTGCGCCACTAAGGGACAAATTC |
| flavo_12_24 | ACCGGCTTTGAAGACTCGCTCTTCC | wolbach_1_24 | GACTTTGCAGCCCATTGTAGCCACC | gamma_20_24 | CGTTACGCACCCGTCCGCCACTCGA |
| flavo_12_25 | TCGTACAGTACCGTCAACTACCCAC | wolbach_1_25 | CGACTTTGCAGCCCATTGTAGCCAC | gamma_20_25 | TCGCGTTAGCTGCGCCACTAAGGGA |
| flavo_13_1 | CGCCGGTCGTCAGCATAGCAAGCTA | rickett_1_1 | TCTCTGCGATCCGCGACCACCATGT | gamma_21_1 | TCGTCAGCGCGAGAGCAAGCTCCGC |
| flavo_13_2 | AGGTCGCTCCTCACGGTAACGAACT | rickett_1_2 | AtCTCTGCGATCCGCGACCACCATG | gamma_21_2 | CTCGTCAGCGCCAGAGCAAGCTCCG |
| flavo_13_3 | GGTGCTCCTCACGGTAACGAACTT | rickett_1_3 | GTCAGTTGTAGCCCAGATGACCGCC | gamma_21_3 | ACTCGTCAGCGCCAGAGCAAGCTCCG |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| flavo_13_4 | TAGGTCGCTCCTCACGGTAACGAAC | rickett_1_4 | CAGTTGTAGCCCAGATGACCGCTT | gamma_21_4 | AGCAAGCTCCGCCTGTTACCGTTCG |
| flavo_13_5 | AGGACGCATAGTCATCTTGTACCCA | rickett_1_5 | TCAGTTGTAGCCCAGATGACCGCCT | gamma_21_5 | GTCAGCGCAGAGCAAGCTCCGCCTG |
| flavo_13_6 | CCTCACGGTAACGAACTTCAGGCAC | rickett_1_6 | CGTCAGTTGTAGCCCAGATGACCGC | gamma_21_6 | GAGCAAGCTCCGCCTGTTACCGTTC |
| flavo_13_7 | TCGCCCAGTGGCTGCTCATTGTCCA | rickett_1_7 | GTTGTAGCCCAGATGACCGCCTTCG | gamma_21_7 | CAAGCTCCGCCTGTTACCGTTCGAC |
| flavo_13_8 | CGTTCGCCGTCGTCAGCATAGCAA | rickett_1_8 | AGTTGTAGCCCAGATGACCGCCTTC | gamma_21_8 | GCTCCGCCTGTTACCGTTCGACTTG |
| flavo_13_9 | GTCGCTCCTCACGGTAACGAACTTC | rickett_1_9 | CATCTCTGCGATCCGCGACCACCAT | gamma_21_9 | CTGGGCTTTCACATCCGACTGACCG |
| flavo_13_10 | GTCGCCCAGTGGCTGCTCATTGTCC | rickett_1_10 | GCGTCAGTTGTAGCCCAGATGACCG | gamma_21_10 | CTTTTGCAAGCCACTCCCATGGTGT |
| flavo_13_11 | TAGGACGCATAGTCATCTTGTACCC | rickett_1_11 | AGCATCTCTGCGATCCGCGACCACC | gamma_21_11 | TCTTTTGCAAGCCACTCCCATGGTG |
| flavo_13_12 | ACCAGTATCAAAGGCAGTTCCATCG | rickett_1_12 | GCATCTCTGCGATCCGCGACCACCA | gamma_21_12 | CTTCTTTTGCAAGCCACTCCCATGG |
| flavo_13_13 | TCCTCACGGTAACGAACTTCAGGCA | rickett_1_13 | TTGTAGCCCAGATGACCGCCTTCG | gamma_21_13 | TTTTGCAAGCCACTCCCATGGTGTG |
| flavo_13_14 | CTAGTTCGCTCCTCACGGTAACGAA | rickett_1_14 | AGCGTCAGTTGTAGCCCAGATGACC | gamma_21_14 | TTTGCAAGCCACTCCCATGGTGTGA |
| flavo_13_15 | CTCCTCACGGTAACGAACTTCAGGC | rickett_1_15 | CCACTAACTAATTGGAGCAAGCCCC | gamma_21_15 | CCTCAGCGTCAGTATTGCTCCAGAA |
| flavo_13_16 | CCGTTCGCCGGTCGTCAGCATAGCA | rickett_1_16 | GCCACTAACTAATTGGAGCAAGCCC | gamma_21_16 | GGGGCTTTCACATCCGACTGACCGTG |
| flavo_13_17 | GTTCGCCGGTCGTCAGCATAGCAAG | rickett_1_17 | CAAGCCCCAATTAGTCCGTTCGACT | gamma_21_17 | CTTTCACATCCGACTGACCGTGCCG |
| flavo_13_18 | CTCACGGTAACGAACTTCAGGCACT | rickett_1_18 | CCGTTCTGCTTCCCTCTGTAAACAC | gamma_21_18 | GGCTTTCACATCCGACTGACCGTGC |
| flavo_13_19 | TCGCTCCTCACGGTAACGAACTTCA | rickett_1_19 | CCGTCTGCCACTAACTAATTGGAGC | gamma_21_19 | CACTCGTCAGCGCAGAGCAAGCTCC |
| flavo_13_20 | GGTCGCCCAGTGGCTGCTCATTGTC | rickett_1_20 | CTCTGCGATCCGCGACCACCATGTC | gamma_21_20 | GCTTTCACATCCGACTGACCGTGCC |
| flavo_13_21 | CGGCATAGTGGTTCAGAGTTGCCT | rickett_1_21 | GCAAGCCCCAATTAGTCCGTTCGAC | gamma_21_21 | TCAGCGCAGAGCAAGCTCCGCCTGT |
| flavo_13_22 | GGCATAGTGGTTCAGAGTTGCCTC | rickett_1_22 | AGCAAGCCCCAATTAGTCCGTTCGA | gamma_21_22 | CGTCAGCGCAGAGCAAGCTCCGCCT |
| flavo_13_23 | CGCGGCATAGTGGTTCAGAGTTGC | rickett_1_23 | TGTAGCCCAGATGACCGCCTTCGCC | gamma_21_23 | AGAGCAAGCTCCGCCTGTTACCGTT |
| flavo_13_24 | GCGGCATAGTGGTTCAGAGTTGCC | rickett_1_24 | GAGCAAGCCCCAATTAGTCCGTTCG | gamma_21_24 | AGCTCCGCCTGTTACCGTTCGACTT |
| flavo_13_25 | GCATAGTGGTTCAGAGTTGCCTCC | rickett_1_25 | GAAGAAAAGCCATCTCTGCGATCCGC | gamma_21_25 | CAGAGCAAGCTCCGCCTGTTACCGT |
| flavo_14_1 | GTGCAAGCACTCCTGTTACCCCCTCG | alpha_5_1 | ACCAAAGCCCTGTGGGCCCTAGCAG | verru_1_1 | CCCGAGATTTCACACCTCACACAT |
| flavo_14_2 | AGTGCAAGCACTCCTGTTACCCCTC | alpha_5_2 | CACCAAAGCCCTGTGGGCCCTAGCA | verru_1_2 | CCCGAGATTTCACACCTCACACATC |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| flavo_14_3 | GCAAGCACTCCTGTTACCCCTCGAC | alpha_5_3 | CCAAAGCCCTGTGGGCCCTAGCAGC | verru_1_3 | TCACACCTCACACATCTATCCGCCT |
| flavo_14_4 | TGCAAGCACTCCTGTTACCCCTCGA | alpha_5_4 | ACCCTATGGTAGATCCCCACGCGTT | verru_1_4 | CACCCTCACACATCTATCCGCTACG |
| flavo_14_5 | CAAGCACTCCTGTTACCCCTTCGACT | alpha_5_5 | CACCCTATGGTAGATCCCCACGCGT | verru_1_5 | TTCACACCTCACACATCTATCCGCC |
| flavo_14_6 | AAGCACTCCTGTTACCCCTCGACTT | alpha_5_6 | GCACCCTATGGTAGATCCCCACGCG | verru_1_6 | ACACCTCACACATCTATCCGCCTAC |
| flavo_14_7 | AGCACTCCTGTTACCCCTCGACTTG | alpha_5_7 | CCGCACCCTATGGTAGATCCCCACG | verru_1_7 | CACACCTCACACATCTATCCGCCTA |
| flavo_14_8 | GCACTCCTGTTACCCCTCGACTTGC | alpha_5_8 | CGCACCCTATGGTAGATCCCCACGC | verru_1_8 | GCCCCGAGATTTCACACCTCACACA |
| flavo_14_9 | TGCTACACGTAGCAGTGTTTCTTCC | alpha_5_9 | TATTCCGCACCCTATGGTAGATCCC | verru_1_9 | ACCTCACACATCTATCCGCCTACGC |
| flavo_14_10 | CCCGTGCGCCGGTCGTCAGCGAGTG | alpha_5_10 | ATTCCGCACCCTATGGTAGATCCCC | verru_1_10 | AGCCCCGAGATTTCACACCTCACAC |
| flavo_14_11 | TCGTCAGCGAGTGCAAGCACTCCTG | alpha_5_11 | TCCGCACCCTATGGTAGATCCCCAC | verru_1_11 | CTCCCGAAGGATAGCTCACGTACTT |
| flavo_14_12 | TGCGCCGGTCGTCAGCGAGTGCAAG | alpha_5_12 | CGCACCAGCTTCGGGTTGATCCAAC | verru_1_12 | CTGCCTCCCGAAGGATAGCTCACGT |
| flavo_14_13 | CGGTCGTCAGCGAGTGCAAGCACTC | alpha_5_13 | TTCCGCACCCTATGGTAGATCCCCA | verru_1_13 | GGCTATGAACCTCCTTGTTGCTCCT |
| flavo_14_14 | CCGTGCGCCGGTCGTCAGCGAGTGC | alpha_5_14 | CCACCAAAGCCCTGTGGGCCCTAGC | verru_1_14 | CCTCCCGAAGGATAGCTCACGTACT |
| flavo_14_15 | GCGCCGGTCGTCAGCGAGTGCAAGC | alpha_5_15 | CCCTATGGTAGATCCCCACGCGTTA | verru_1_15 | CCCGAAGGATAGCTCACGTACTTCG |
| flavo_14_16 | GGTCGTCAGCGAGTGCAAGCACTCC | alpha_5_16 | CCTATGGTAGATCCCCACGCGTTAC | verru_1_16 | TCCCGAAGGATAGCTCACGTACTTC |
| flavo_14_17 | GCCGGTCGTCAGCGAGTGCAAGCAC | alpha_5_17 | GCGCACCAGCTTCGGGTTGATCCAA | verru_1_17 | GAGGGTATGAACCTCCTTGTTGCTC |
| flavo_14_18 | GTCAGCGAGTGCAAGCACTCCTGTT | alpha_5_18 | GCACCAGCTTCGGGTTGATCCAACT | verru_1_18 | GACGCTGCCTCCCGAAGGATAGCTC |
| flavo_14_19 | CCGGTCGTCAGCGAGTGCAAGCACT | alpha_5_19 | AGCGCACCAGCTTCGGGTTGATCCA | verru_1_19 | AGGCTATGAACCTCCTTGTTGCTCC |
| flavo_14_20 | TCAGCGAGTGCAAGCACTCCTGTTA | alpha_5_20 | CTATGGTAGATCCCCACGCGTTACG | verru_1_20 | GCCTCCCGAAGGATAGCTCACGTAC |
| flavo_14_21 | CGTGCGCCGGTCGTCAGCGAGTGCA | alpha_5_21 | GCCACCAAAGCCCTGTGGGCCCTAG | verru_1_21 | CGCTGCCTCCCGAAGGATAGCTCAC |
| flavo_14_22 | CGCCGGTCGTCAGCGAGTGCAAGCA | alpha_5_22 | CACCAGCTTCGGGTTGATCCAACTC | verru_1_22 | TGCCTCCCGAAGGATAGCTCACGTA |
| flavo_14_23 | GTGCCGGTCGTCAGCGAGTGCAAGC | alpha_5_23 | TAGCGCACCAGCTTCGGGTTGATCC | verru_1_23 | ACGCTGCCTCCCGAAGGATAGCTCA |
| flavo_14_24 | CGTCAGCGAGTGCAAGCACTCCTGT | alpha_5_24 | CAAAGCCCTGTGGGCCCTAGCAGCT | verru_1_24 | GCTGCCTCCCGAAGGATAGCTCACG |
| flavo_14_25 | GTCGTCAGCGAGTGCAAGCACTCCT | alpha_5_25 | CGCCACCAAAGCCCTGTGGGCCCTA | verru_1_25 | AGGACGCTGCCTCCCGAAGGATAGC |
| flavo_15_1 | GGCGTACTCCCCAGTGCATCACTT | alpha_6_1 | GCGCCACTAACCCGAAGCTTCGTT | verru_2_1 | CGTCGCATGTTCACACTTTCGTGCA |

TABLE 1-continued list of probes specific for laboratory bacterial strains
and San Francisco Bay natural community

| SEQUENCE_ID | PROBE_SEQUENCE | SEQUENCE_ID | PROBE_SEQUENCE | SEQUENCE_ID | PROBE_SEQUENCE |
|---|---|---|---|---|---|
| flavo_15_2 | CTCCCCAGGTGCATCACTTAATACT | alpha_6_2 | CTTCTTGCGAGTAGCTGCCCACTGT | verru_2_2 | CTACCCTAACTTTCGTCCATGAGCG |
| flavo_15_3 | GCGTACTCCCCAGGTGCATCACTTA | alpha_6_3 | CCCAGCTTGTTGGGCCATGAGGACT | verru_2_3 | ACCCTAACTTTCGTCCATGAGCGTC |
| flavo_15_4 | CGGGCTACTCCCCAGGTGCATCACT | alpha_6_4 | ATCTTCTTGCGAGTAGCTGCCCACT | verru_2_4 | GCGTCGCATGTTCACACTTTCGTGC |
| flavo_15_5 | ACTCCCCAGGTGCATCACTTAATAC | alpha_6_5 | TCTTCTTGCGAGTAGCTGCCCACTG | verru_2_5 | CAAGTGTTCCCTTCTCCCCTTCCAGT |
| flavo_15_6 | CGTACTCCCCAGGTGCATCACTTAA | alpha_6_6 | TAGCCCCAGCTTGTTGGGCCATGAGG | verru_2_6 | TACACCAAGTGTTCCCTTCTCCCCT |
| flavo_15_7 | CCGGCGTACTCCCCAGGTGCATCAC | alpha_6_7 | GCCACTAACCCCGAAGCTTCGTTCG | verru_2_7 | CCAAGTGTTCCCTTCTCCCCTCCAG |
| flavo_15_8 | GTACTCCCCAGGTGCATCACTTAAT | alpha_6_8 | GTAGCCCAGCTTGTTGGGCCATGAG | verru_2_8 | ACACCAAGTGTTCCCTTCTCCCCTC |
| flavo_15_9 | GCCGGCGTACTCCCCAGGTGCATCA | alpha_6_9 | CGCCACTAACCCCGAAGCTTCGTTC | verru_2_9 | CGCTACACCAAGTGTTCCCTTCTCC |
| flavo_15_10 | GAAGAGAAGGCCTGTTTCCAAGCCG | alpha_6_10 | TTCTTGCGAGTAGCTGCCCACTGTC | verru_2_10 | CACCAAGTGTTCCCTTCTCCCCTCC |
| flavo_15_11 | CAACAGCGAGTGATGATCGTTTACG | alpha_6_11 | TAGCATCTTCTTGCGAGTAGCTGCC | verru_2_11 | GCTACACCAAGTGTTCCCTTCTCCC |
| flavo_15_12 | GCATGCCCATCTCATACCGAAAAAC | alpha_6_12 | AGCATCTTCTTGCGAGTAGCTGCCC | verru_2_12 | CTACACCAAGTGTTCCCTTCTCCCC |
| flavo_15_13 | TTGTAATCTGCTCCGAAGAGAAGGC | alpha_6_13 | GCCCAGCTTGTTGGGCCATGAGGAC | verru_2_13 | AGTGTTCCCTTCTCCCCTCCAGTAC |
| flavo_15_14 | CGCCGGTCGTCAGCAAAAGCAAGCT | alpha_6_14 | CACTAACCCCGAAGCTTCGTTCGAC | verru_2_14 | AAGTGTTCCCTTCTCCCCTCCAGTA |
| flavo_15_15 | AAGAGAAGGCCTGTTTCCAAGCCGG | alpha_6_15 | CATCTTCTTGCGAGTAGCTGCCCAC | verru_2_15 | ACCAAGTGTTCCCTTCTCCCCTCCA |
| flavo_15_16 | GCCGGTCGTCAGCAAAAGCAAGCTT | alpha_6_16 | TGTAGCCCAGCTTGTTGGGCCATGA | verru_2_16 | GCTACCCTAACTTTCGTCCATGAGC |
| flavo_15_17 | TGCCGGTCGTCAGCAAAAGCAAGCTGCATC | alpha_6_17 | AGCCCAGCTTGTTGGGCCATGAGGA | verru_2_17 | GTTCCCTTCTCCCCTCCAGTACTCT |
| flavo_15_18 | GCGCCGGTCGTCAGCAAAAGCAAGC | alpha_6_18 | CCACTAACCCCGAAGCTTCGTTCGA | verru_2_18 | GTGTTCCCTTCTCCCCTCCAGTACT |
| flavo_15_19 | CGAAGAGAAGGCCTGTTTCCAAGCC | alpha_6_19 | GCATCTTCTTGCGAGTAGCTGCCCA | verru_2_19 | TGTTCCCTTCTCCCCTCCAGTACTC |
| flavo_15_20 | CCAACAGCGAGTGATGATCGTTTAC | alpha_6_20 | GTGTAGCCCAGCTTGTTGGGCCATG | verru_2_20 | CCGTACACCAAGTGTTCCCTTCTC |
| flavo_15_21 | GGAGTATTAATCCCCGTTTCCAGGG | alpha_6_21 | TGCGCCACTAACCCCGAAGCTTCGT | verru_2_21 | TTCCCTTCTCCCCTCCAGTACTCTA |
| flavo_15_22 | TGGAGTATTAATCCCCGTTTCCAGG | alpha_6_22 | CTCAAGACCAAGTGCCGAACAGC | verru_2_22 | GGCGTCGCATGTTCACACTTTCGTG |
| flavo_15_23 | TCCCCGTTTCCAGGGGCTATCCTCC | alpha_6_23 | CCAGCTTGTTGGGCCATGAGGACTT | verru_2_23 | CGCTACCCTAACTTTCGTCCATGAG |
| flavo_15_24 | TGCGCCGGTCGTCAGCAAAAGCAAG | alpha_6_24 | ACTAACCCCGAAGCTTCGTTCGACT | verru_2_24 | CCCTAACTTTCGTCCATGAGCGTCA |
| flavo_15_25 | AACAGCGAGTGATGATCGTTTACGG | alpha_6_25 | TCTTGCGAGTAGCTGCCCACTGTCA | verru_2_25 | ACCGTACACCAAGTGTTCCCTTCT |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08906610B2). An electronic copy of the "Sequence Listing" will also be available from the USPTO upon request and payment of the fee set forth in 37 CFR 1.19(b)(3).

What is claimed is:

1. A method for determination of stable isotope incorporation in a community of organisms comprising the steps of:
   a) supplying said community of organisms with at least two substrates simultaneously for a defined period of time, wherein each of the at least two substrates is labeled with a different stable isotope;
   b) extracting RNA from the organisms;
   c) fragmenting said RNA to provide fragmented RNA;
   d) labeling a fraction of the fragmented RNA with a detectable label to provide labeled fragmented RNA;
   e) hybridizing the labeled fragmented RNA to a set of oligonucleotide probes, wherein the set of oligonucleotide probes is an array of oligonucleotide probes attached to a substrate;
   f) detecting hybridization signal strength of labeled fragmented RNA hybridized to the oligonucleotide probes to determine the community organism composition;
   g) identifying a responsive set of oligonucleotide probes based on the hybridization signal strength in step f);
   h) hybridizing a fraction of unlabeled fragmented RNA to a second array of oligonucleotide probes, wherein the second array comprises the responsive set of oligonucleotide probes attached to a conductive substrate;
   i) detecting the unlabeled fragmented RNA hybridized to the responsive set of probes to determine the stable isotope incorporation into the community of organisms using imaging mass spectrometry or spectroscopy.

2. The method of claim 1, wherein said organism is a bacterium, archaea, virus, fungus, plant, arthropod, nematode, or other eukaryote.

3. The method of claim 2, wherein said organism is a bacterium.

4. The method of claim 1, wherein the stable isotopes are selected from the group consisting of $^3H$, $^{13}C$, $^{15}N$, and $^{18}O$.

5. The method of claim 1, wherein in step b) the extracting step is carried out by physical or chemical cell lysis followed by affinity column purification.

6. The method of claim 1, wherein in step c) the fragmenting step is carried out by using enzymes, chemicals, or heat, or a combination of these.

7. The method of claim 1, wherein in step d) the RNA is labeled with a fluorescent molecule or a non-fluorescent molecule.

8. The method of claim 1, wherein steps c) and d) are carried out concurrently.

9. The method of claim 1, wherein step e) further comprises the steps of adding said labeled fragmented RNA to a hybridization solution and contacting said hybridization solution with the array of oligonucleotide probes.

10. The method of claim 1, wherein the set of oligonucleotide probes comprises 16S rRNA phylogenetic oligonucleotide probes.

11. The method of claim 10, wherein said set of 16S rRNA phylogenetic probes further comprises probes from the 16S rRNA gene, 23S rRNA gene, 5S rRNA gene, 5.8S rRNA gene, 12S rRNA gene, 18S rRNA gene, 28S rRNA gene, gyrB gene, rpoB gene, fusA gene, recA gene, cox1 gene, nif13 gene, or a combination thereof.

12. The method of claim 7, wherein the RNA is labeled with a fluorescent molecule.

13. The method of claim 7, wherein the RNA is labeled with a non-fluorescent molecule.

14. The method of claim 1, wherein in step f) the hybridized labeled RNA is imaged with a fluorescence scanner and fluorescence intensity is measured for each probe feature.

15. The method of claim 1, wherein in step f) the detection of hybridization signal strength provides a determination of genes present in the community of organisms.

16. The method of claim 1, wherein in step f) the detection of hybridization signal strength is used for normalization of the isotope signals detected in step i).

17. The method of claim 1, wherein in step i) the hybridized unlabeled fragmented RNA are imaged with a secondary ion mass spectrometer and isotope ratios are measured for each probe feature.

18. The method of claim 1, wherein in step i) the hybridized unlabeled fragmented RNA are imaged with a nano-scale secondary ion mass spectrometer device and isotope ratios are measured for each probe feature.

19. The method of claim 1, wherein in step e) the substrate is a solid planar substrate, a microarray slide, spheres or beads, wherein the substrate is comprised of silicon, glass, metals, semiconductor materials, polymers or plastics.

20. The method of claim 18, wherein in step h) the responsive probe substrate is a solid planar substrate, a microarray slide, spheres or beads, wherein the responsive probe substrate is comprised of silicon, glass, metals, semiconductor materials, polymers or plastics.

21. The method of claim 20, wherein the responsive probe substrate is a solid planar substrate coated with indium tin oxide (ITO).

22. The method of claim 1, wherein in step e) the set of oligonucleotide probes is identified and selected from unique sequence regions of the fragmented RNA.

23. A method for determination of stable isotope incorporation in a community of organisms comprising the steps of:
   a) supplying said community of organisms with at least two substrates simultaneously for a defined period of time, wherein each of the at least two substrates is labeled with a different stable isotope;
   b) extracting RNA from the organisms;
   c) fragmenting said RNA to provide fragmented RNA, generating cDNAs from a fraction of said fragmented RNA and sequencing said cDNAs;

d) designing a first set of oligonucleotide probes based on unique sequence regions of said sequenced cDNAs generated from the fragmented RNA;

e) labeling a fraction of the fragmented RNA with a detectable label to provide labeled fragmented RNA;

f) hybridizing the labeled fragmented RNA to the first set of oligonucleotide probes, wherein the first set of oligonucleotide probes is an array of oligonucleotide probes attached to a substrate, and detecting hybridization signal strength of the labeled fragmented RNA hybridized to the first set of oligonucleotide probes to determine the community organism composition;

g) identifying a responsive set of oligonucleotide probes based on the hybridization signal strength in step f);

h) hybridizing a fraction of unlabeled fragmented RNA to a second array of oligonucleotide probes, wherein the second array comprises the responsive set of oligonucleotide probes attached to a conductive substrate;

i) detecting the unlabeled fragmented RNA hybridized to the responsive set of probes to determine the stable isotope incorporation into the community of organisms using imaging mass spectrometry or spectroscopy.

24. The method of claim 23, wherein said organism is a bacterium, archaea, virus, fungus, plant, arthropod, nematode, or other eukaryote.

25. The method of claim 24, wherein said organism is a bacterium.

26. The method of claim 23, wherein the stable isotopes are selected from the group consisting of $^3H$, $^{13}C$, $^{15}N$, and $^{18}O$.

27. The method of claim 23, wherein in step b) the extracting step is carried out by physical or chemical cell lysis followed by affinity column purification.

28. The method of claim 23, wherein in step c) the fragmenting step is carried out by using enzymes, chemicals, or heat, or a combination of these.

29. The method of claim 23, wherein in step e) the RNA is labeled with a fluorescent molecule or a non-fluorescent molecule.

30. The method of claim 23, wherein steps c) and e) are carried out concurrently.

31. The method of claim 23, wherein step f) further comprises the steps of adding said labeled fragmented RNA to a hybridization solution and contacting said hybridization solution with the array of oligonucleotide probes.

32. The method of claim 23, wherein the set of oligonucleotide probes comprises 16S rRNA phylogenetic oligonucleotide probes.

33. The method of claim 32, wherein said set of 16S rRNA phylogenetic probes further comprises probes from the 16S rRNA gene, 23S rRNA gene, 5S rRNA gene, 5.8S rRNA gene, 12S rRNA gene, 18S rRNA gene, 28S rRNA gene, gyrB gene, rpoB gene, fusA gene, recA gene, cox1 gene, nif13 gene, or a combination thereof.

34. The method of claim 29, wherein the RNA is labeled with a fluorescent molecule.

35. The method of claim 29, wherein the RNA is labeled with a non-fluorescent molecule.

36. The method of claim 23, wherein in step f) the hybridized labeled RNA is imaged with a fluorescence scanner and fluorescence intensity is measured for each probe feature.

37. The method of claim 23, wherein in step f) the detection of hybridization signal strength provides a determination of genes present in the community of organisms.

38. The method of claim 23, wherein in step f) the detection of hybridization signal strength is used for normalization of isotope signals detected in step i).

39. The method of claim 23, wherein in step i) the hybridized unlabeled fragmented RNA are imaged with a secondary ion mass spectrometer and isotope ratios are measured for each probe feature.

40. The method of claim 23, wherein in step i) the hybridized unlabeled fragmented RNA are imaged with a nanoscale secondary ion mass spectrometer device and isotope ratios are measured for each probe feature.

41. The method of claim 23, wherein in step f) the substrate is a solid planar substrate, a microarray slide, spheres or beads, wherein the substrate is comprised of silicon, glass, metals, semiconductor materials, polymers or plastics.

42. The method of claim 23, wherein in step h) the responsive probe substrate is a solid planar substrate, a microarray slide, spheres or beads, wherein the responsive probe substrate is comprised of silicon, glass, metals, semiconductor materials, polymers or plastics.

43. The method of claim 25, wherein the responsive probe substrate is a solid planar substrate coated with indium tin oxide (ITO).

* * * * *